US010246688B2

(12) United States Patent
King et al.

(10) Patent No.: US 10,246,688 B2
(45) Date of Patent: Apr. 2, 2019

(54) DITERPENOID SYNTHESIS

(71) Applicant: The University of York, York (GB)

(72) Inventors: Andrew King, York (GB); Ian Graham, York (GB)

(73) Assignee: The University of York, York (GB)

( * ) Notice: Subject to any disclaimer, the term of this patent is extended or adjusted under 35 U.S.C. 154(b) by 45 days.

(21) Appl. No.: 15/105,502

(22) PCT Filed: Jan. 9, 2015

(86) PCT No.: PCT/GB2015/050035
§ 371 (c)(1),
(2) Date: Jun. 16, 2016

(87) PCT Pub. No.: WO2015/104553
PCT Pub. Date: Jul. 16, 2015

(65) Prior Publication Data

US 2016/0319250 A1 Nov. 3, 2016

(30) Foreign Application Priority Data

Jan. 13, 2014 (GB) .................................. 1400512.8

(51) Int. Cl.

| | |
|---|---|
| ***C12N 15/82*** | (2006.01) |
| ***C12P 7/02*** | (2006.01) |
| ***C12N 9/00*** | (2006.01) |
| ***C12N 9/02*** | (2006.01) |
| ***C12N 15/52*** | (2006.01) |
| ***C12P 7/26*** | (2006.01) |

(52) U.S. Cl.
CPC ........... *C12N 9/0071* (2013.01); *C12N 15/52* (2013.01); *C12N 15/8243* (2013.01); *C12P 7/02* (2013.01); *C12P 7/26* (2013.01)

(58) Field of Classification Search
None
See application file for complete search history.

(56) References Cited

U.S. PATENT DOCUMENTS

2008/0281135 A1 11/2008 Tissier et al.

OTHER PUBLICATIONS

Zerbe et al., 2013, Plant Physiol. 162: 1073-109, published Jun. 2013.*
Coon, 2005, Annu. Rev. Pharmacol. Toxicol. 45: 1-25.*
Keskin et al., 2004, Protein Science 13: 1043-1055.*
Thornton et al., 2000, Nature Structural Biology, structural genomic supplement, Nov. 2000: 991-994.*
Guo et al., 2004, Proceedings of the National Academy of Sciences USA 101: 9205-9210.*
Devappa et al., 2011, J. Am. Oil. Chem. Soc. 88: 301-322.*
Chan et al., 2010, Nature Biotechnology 28: 951-956, including online methods.*
Sequence of Ricinus communis cytochrome P450, NCBI/GenBank accession No. XM_002513296.1, published Aug. 6, 2009.*
Sato et al., 2011, DNA Research 18: 65-76, with supplementary data.*
Sequence of Ricinus communis premnaspirodiene oxygenase (LOC8259983), NCBI/GenBank accession No. NM_001323698.1, published Jan. 4, 2017.*
Sequence of Jatropha curcas premnaspirodiene oxygenase-like (CYP726A20), NCBI/GenBank accession No. NM_001308746.1, published Oct. 30, 2016.*
Brückner and Tissier, 2013, Plant Methods 9:46, pp. 1-10.*
Mizutani, 2012, Biol. Pharm. Bull. 35: 824-832.*
Kirby et al., 2010, Phytochemistry 71: 1466-1473.*
Accession No. B9RHX3, retrieved from EBI Accession No. UNIPROT:B9RHX3 on Mar. 24, 2009.
Accession No. JL056356, retrieved from EBI Accession No. EM_TSA:JL056356 on May 12, 2012.
Brückner and Tissier, "High-Level Diterpene Production by Transient Expression in *Nicotiana benthamiana,*" *Plant Methods* 9:46, 2013.
Cahoon et al., "Transgenic Production of Epoxy Fatty Acids by Expression of a Cytochrome P450 Enzyme from *Euphorbia lagascae* Seed," *Plant Physiol.* 128:615-624, 2002.
Chan et al., "Draft Genome Sequence of the Oilseed Species *Ricinus communis,*" *Nature Biotechol.* 28:951-959, 2010.
King et al., "Production of Bioactive Diterpenoids in the Euphorbiaceae Depends on Evolutionarily Conserved Gene Clusters," *Plant Cell* 26:3286-3298, 2014.
Kirby et al., "Cloning of Casbene and Neocembrene Synthases from Euphorbiaceae Plants and Expression in *Saccharomyces cerevisiae,*" *Phytochem.* 71:1466-1473, 2010.
Zerbe et al., "Gene Discovery of Modular Diterpene Metabolism in Nonmodel Systems," *Plant Physiol.* 162:1073-1091, 2013.
Great Britain Application No. GB1400512.8 Search Report dated Sep. 18, 2014 (5 pages).
PCT/GB2015/050035 Search Report and Written Opinion dated Apr. 2, 2015 (13 pages).

* cited by examiner

*Primary Examiner* — Bratislav Stankovic
(74) *Attorney, Agent, or Firm* — Klarquist Sparkman, LLP

(57) ABSTRACT

The present disclosure relates to nucleic acids that encode polypeptides with cytochrome P450 activity involved in the biosynthesis of plant derived diterpenoids or diterpenes.

9 Claims, 22 Drawing Sheets

Specification includes a Sequence Listing.

Casbene synthase
Casbene synthase + CYP726A14
Casbene synthase + CYP726A14 & CYP726A16
23.05
27.08
27.19
28.93
Relative abundance
Retention time (min)

Casbene
RT 23.05
Relative Abundance
m/z

Casbene oxidation product
RT 27.08
Relative Abundance
m/z

Casbene oxidation product
RT 27.19
Relative Abundance
m/z

Casbene oxidation product
RT 28.93
Relative Abundance
m/z

Fig. 5 cDNA sequences

CYTOCHROME P450

From *Ricinus communis*

SEQ ID NO: 1

>CYP726A18
ATGTCATCACAACCAGCAGTTTTACAATCCAACTTCCTTAACAGAAACGTCCAGCCATTTCTAACCATTCCCTCTGCTT
CTACCAAGTATAGTGGCACCGCTTGTTTCTCTTCCTTTCCCTCAGTTAAATTAAATGCTAGACCACCGCAAGCATGCTT
CTCCTTGAATAAAAACAACGATCACTCTACCCCCACCTCCATCCTTCCTCCAGGACCTTGGCAGTTACCTCTGATAGGT
AACATACACCAGCTCGTCGGCCATTTACCCCATAGCCGCCTGAGAGACTTGGGAAAAATTTATGGACCTGTGATGAGTG
TTCAACTCGGAGAAGTTTCTGCTGTGGTGGTATCATCAGTAGAAGCAGCCAAAGAAGTGCTGAGGATCCAGGATGTCAT
CTTCGCTGAAAGACCTCCTGTCCTCATGGCAGAAATTGTGCTCTACAATCGTCATGATATTGTTTTTGGGTCTTATGGA
GATCACTGGAGACAACTTAGAAAGATTTGCACATTGGAGTTGCTTAGTCTTAAGCGCGTGCAATCTTTCAAATCAGTCA
GGGAAGACGAGTTTTCAAATTTTATCAAATACCTTTCTTCCAAAGCCGGAACTCCAGTCAATCTTACTCACGACTTGTT
TTCTTTAACAAATTCTGTTATGTTAAGAACCTCCATAGGCAAGAAATGCAAAAACCAAGAAGCAATTTTAAGAATCATC
GACAGTGTTGTTGCGGCAGGAGGAGGTTTCAGTGTTGCTGATGTGTTTCCTTCCTTCAAATTGCTCCATATGATTAGCG
GAGACAGGTCAAGTCTTGAGGCCTTACGTCGAGACACAGACGAGATACTTGACGAAATCATTAATGAACACAAAGCCGG
CAGGAAGGCTGGTGATGATCACGACGAAGCTGAAAATCTTCTGGATGTTCTTTTGGATCTTCAGGAAAATGGAGACCTG
GAAGTCCCTTTAACCAACGACAGCATCAAAGCAACAATTCTGGATATGTTTGGGGCTGGTAGCGACACGTCCTCAAAAA
CAGCAGAATGGGCGTTGTCGGAGTTGATGAGACACCCAGAAATAATGAAAAAGGCACAGGAGGAAGTGAGGGGAGTCTT
TGGTGATAGCGGAGAAGTCGATGAAACACGCCTTCATGAATTAAAATACTTGAAGTTAGTGATCAAAGAAACATTGAGA
TTACATCCTGCCATTCCATTAATTCCAAGAGAATGCAGGGAAAGGACTAAGATTAATGGATATGACGTATATCCCAAAA
CCAAGGTCCTTGTCAATATTTGGGCAATCTCAAGAGATCCAAATATATGGAGCGAAGCAGATAAATTCAAACCAGAAAG
ATTCTTGAACAGTTCACTTGATTACAAGGGTAATTATCTGGAATTCGCTCCGTTTGGTTCTGGGAAAAGGGTATGTCCT
GGTATGACATTAGGTATAACTAATCTAGAGCTCATCCTTGCAAAATTACTATATCATTTTGACTGGAAACTTCCTGATG
GAATAACGCCTGAGACGCTTGACATGACTGAATCTGTTGGTGGCGCAATTAAAAGAAGAACAGACCTTAACTTGATTCC
TGTTCTATATCCTACACATTGA

SEQ ID NO: 2

>CYP726A14
ATGGAGCAGCAATTGCTATCGTTTCCAGCCCTTTTGAGCTTTCTCCTTTTAATCTTCGTGGTACTAAGGATCTGGAAGC
AATACACATACAAAGGAAAATCCACCCCACCCCCTGGACCATGGAGATTACCTCTCCTAGGCAACTTTCACCAGCTAGT
TGGTGCTCTACCCCACCACCGCCTAACCGAATTGGCCAAAATTTATGGACCAGTTATGGGTATTCAACTTGGTCAGATT
TCTGTTGTCATCATTTCCTCAGTAGAAACAGCCAAAGAAGTGCTTAAAACCCAGGGTGAGCAGTTCGCTGATAGAACCC
TTGTCCTCGCAGCAAAAATGGTACTTTATAATCGCAACGACATTGTGTTTGGATTATACGGAGACCACTGGAGACAACT
GAGAAAATTATGCACATTGGAGCTGCTTAGTGCAAAACGTGTCCAATCATTCAAGTCCGTCAGAGAAGAAGAGCTCTCA
AATTTTGTAAAGTTCCTTCATTCCAAAGCAGGAATGCCCGTCAATCTTACTCACACGTTGTTTGCTTTGACAAACAATA
TTATGGCAAGAACATCTGTAGGTAAAAAATGCAAGAACCAGGAAGCCCTCTTAAGTATTATAGATGGCATCATTGATGC
ATCAGGAGGTTTTACTATTGCGGATGTGTTTCCTTCCGTTCCCTTCCTCCACAACATATCTAATATGAAATCGAGATTG
GAGAAGTTGCATCAACAAGCGGACGATATTCTTGAAGACATCATAAATGAACACAGAGCCACCAGGAATCGTGATGATC
TGGAAGAAGCTGAAAATCTCCTTGATGTTCTTTTGGATCTTCAGGAAAATGGAAACCTTGAAGTCCCTTTGACCAATGA
CAGCATCAAGGGAGCCATTCTGGATATGTTTGGAGCTGGTAGCGACACATCCTCAAAAACAGCCGAATGGGCATTGTCG
GAGTTGATGAGGCACCCAGAAGAAATGAAAAAGGCACAAGAAGAGGTGAGGCGAATTTTTGGTGAAGATGGAAGAATTG
ATGAAGCTCGATTTCAAGAATTGAAGTTCTTGAATTTAGTTATCAAAGAAACTCTGAGATTACATCCTCCAGTAGCACT
GATTCCAAGAGAATGTAGGGAAAAAACTAAGGTTAATGGATACGATATCTATCCTAAAACTAGAACACTCATTAATGTT
TGGTCTATGGGAAGGGATCCCAGTGTTTGGACTGAAGCTGAGAAGTTCTACCCGGAAAGGTTTCTGGATGGCACAATTG
ATTATAGAGGTACTAATTTTGAACTAATTCCATTTGGTGCAGGAAAAAGGATATGTCCTGGTATGACATTAGGGATAGT
TAACCTTGAGCTTTTCCTTGCGCACCTATTGTATCATTTTGACTGGAAGCTTGTTGATGGAGTGGCTCCTGACACTCTT
GACATGAGTGAAGGTTTTGGCGGTGCACTTAAAAGGAAAATGGACCTTAACTTGGTTCCCATTCCATTCACTACTTTGC
CATAG

Fig. 6

SEQ ID NO: 3

>CYP726A17
ATGGAGAAACAAATCCTATCATTTCCAGTCTTATTAAGCTTTGTCCTTTTTATCTTAATGATCTTAAGGATATGGAAGA
AAAGCAACCCACCTCCAGGACCATGGAAATTACCTCTGTTAGGCAACATTCACCAGCTGGCTGGTGGTGCTCTGCCCCA
TCACCGCCTAAGGGACTTGGCAAAAACTTATGGACCAGTTATGAGTATTCAACTCGGCCAGATTTCTGCTGTCGTAATT
TCTTCAGTACAAGGAGCCAAAGAAGTGCTGAAGACTCAGGGTGAGGTGTTCGCTGAAAGACCCCTCATCATCGCAGCTA
AAATTGTGCTTTATAATCGTAAGGATATTGTATTTGGTTCCTACGGAGATCACTGGAGACAAATGAGAAAGATCTGCAC
CTTAGAGCTACTGAGTGCCAAACGCGTCCAGTCCTTTAGATCCGTCAGGGAAGAAGAGGTCTCAGAATTTGTGAGATTT
CTTCAATCCAAAGCAGGAACGCCAGTCAATCTTACCAAGACCCTGTTTGCTTTAACAAATTCTATCATGGCAAGAACAT
CCATAGGTAAAAAATGTGAAAAACAAGAAACGTTTTCAAGTGTTATAGACGGTGTCACTGAGGTATCAGGAGGTTTTAC
TGTTGCTGATGTGTTTCCTTCTTTGGGATTCCTTCACGTCATCACTGGTATGAAGTCTAGACTAGAGAGGTTGCACCGA
GTAGCAGATCAGATATTTGAAGATATAATAGCTGAACACAAAGCCACCAGGGCACTCTCCAAGAACGATGATCCGAAAG
AAGCAGCTAATCTTCTAGATGTTCTTTTGGATCTTCAGGAACACGGAAATCTTCAGGTCCCTTTAACCAACGACAGCAT
CAAAGCAGCCATTCTGGAAATGTTTGGTGCTGGGAGCGACACATCCTCAAAAACCACAGAATGGGCCATGTCAGAGTTG
ATGAGGAACCCAACAGAAATGAGAAAAGCACAAGAAGAAGTGAGGCGAGTGTTTGGTGAAACAGGGAAGGTTGATGAAA
CACGCCTTCATGAATTAAAGTTTTTGAAGTTGGTTGTCAAAGAAACTYTGAGATTACATCCTGCCATAGCATTAATTCC
AAGAGAATGCAGGGAGAGGACTAAGGTTGACGGGTATGACATAAAACCCACAGCTAGAGTCCTCGTCAATGTATGGGCG
ATTGGAAGGGATCCTAATGTTTGGAGTGAACCTGAAAGGTTTCACCCAGAAAGGTTTGTCAATAGTTCAGTTGATTTCA
AGGGTACTGATTTCGAACTACTTCCATTTGGTGCAGGAAAGAGAATATGCCCTGGTATTTTAGTGGGTATAACTAATTT
AGAGCTTGTTTTAGCTCACCTATTATATCATTTTGATTGGAAATTTGTTGATGGAGTGACGAGTGATAGTTTTGATATG
AGAGAAGGTTTTGGTGGGGCACTTCATAGAAAATCAGACCTTATCTTGATTCCCATTCCATTTACTCCTTAG

SEQ ID NO: 4

>CYP726A19
ATGGCAACACTTCAACATTCAATGCAAGCAAATTTACAGAAACAAAATCTTCATCCATTGTTAAACAAATCCTTTGGTA
CTCCGAATCGTCCTTCCTTCGTCTATTCCTCGAAATCTGCATCCCGAAGAACAATCCAAGCATGTTTATCTTCAAATTC
ACAGCCTGGAGGAGTTTGCCCCATGGCTAATCGCTTTGCTTCCTCAACTACTAATCAATCTGTTACTGAGTCCAGTTCA
AAACCAGATGAAGAGGATGAAAATTCTCCGGTTAAACTTCCTCCGGGACCGTGGAAATTACCTTTGCTCGGTAATATTC
TCCAGCTCGTTGGAGACCTACCGCATAGTCGCCTACGAGATTTAGCGACAGAATACGGACCTGTTATGAGTGTTCAACT
CGGTGAAGTTTACGCTGTGGTAATTTCATCTGTTGAAGCAGCTAGAGAAATTCTCAGAAATCAGGATGTAAATTTTGCT
GATAGACCGCCGGTCTTAGTATCCGAAATTGTTCTTTACAATCGTCAGGATATCGTTTTCGGTGCCTACGGAGTTCATT
GGCGACAAATGAGAAGACTATGCACGACGGAATTGCTTAGTATAAAACGTGTTCAGTCATTCAAATTAGTCCGTGAAGA
AGAGGTTTCGAATTTCATCAAATCGCTTTACTCGAAAGCAGGAAAGCCCGTTAATCTTACCGAGGGTTTGTTCACGTTG
ACGAATTCGATAATGTTGAGGACGTCGATCGGTAAGAAATGCAGGGATCAAGATACACTTTTGAGAGTAATTGAAGGAG
TTGTGGCGGCCGGAGGAGGTTTTAGCATCGCGGATGTGTTTCCTTCTGCCGTGTTCCTTCACGATATCAATGGAGACAA
GTCGGGCCTCCAGAGTTTGCGGCGAGATGCTGATTTGATACTCGACGAGATCATTGGTGAACATAGAGCTATTAGAGGT
ACTGGTGGGGATCAAGGTGAAGCTGATAATCTTTTAGATGTTCTTCTGGATCTTCAGGAAAATGGAAATCTTGAAGTCC
CTTTGAATGATGATAGCATCAAAGGGGCAATTCTGGACATGTTTGGGGCAGGAAGTGACACCTCATCAAAATCAACAGA
ATGGGCGTTATCAGAATTACTACGACACCCAGAAGAAATGAAAAAAGCACAAGACGAAGTAAGACGAGTTTTTGCAAAG
AAAGGAAATGTAGAAGAATCACAACTTGACCAATTAAAATACCTGAAATTAGTCATCAAAGAAACTCTGAGACTACACC
CAGCAGTCCCTTTAATCCCAAGAGAATGCAGAGAAAAAACCAAGGTCAATGGATATGATATTCTCCCAAAAACTAAGGC
ACTTGTGAATATTTGGGCAATCTCTAGGGACCCCAAAATTTGGCCTGAAGCAGATAAATTTATACCTGAAAGATTCGAA
AATAGTTCAATTGATTTTAAGGGAAATAACTTGGAATTCGCTCCGTTTGGTTCAGGAAAAAGAATATGTCCAGGCATGG
CCTTGGGGATAACTAATTTGGAGCTTTTTCTGGCACAACTTTTGTATCATTTCGATTGGAAACTTGCCGACGGGAAAGA
CGGTAGGGATCTTGACATGGGTGAAGTTGTTGGTGGTGCTATTAAAAGAAAAGTAGACCTCAATTTGATTCCTATTCCA
TTCCATACTTCACCTGCAAACTGA

Fig. 7

SEQ ID NO: 5, *Euphorbia fischeriana*

>Efi003329
ATGTCAACACTTCAACCTTTTCTGCAAGCAAATTTTCAGAAGCAAAATTCTCATCCATTGTTAAGCAAACCTTTAGGTA
CTACCAATCATCCTTCCTTCATTTCTTCGTCTAAATCAACAAAAAGATCAACTATTCAAGCATGTTTATCTTCAAATTC
GCAGCCTGGTGGAGTTTGCCCCATGGCTAATCGCTTTGCTTCTTCTTCAACTACTAATCAATCTGTTACTCAGTCCAGT
TCAAACCCAGATGAAAAGGACGGAAATTCACAGGTTCAGCTTCCTCCGGGGCCGTGGAAATTACCTTTCATCGGTAATA
TTCTCCAGCTCGTCGGAGATCTACCCCATCGTCGCCTAAGAGATTTGGCGACAGTGTACGGACCTGTTATGAGTGTTCA
ACTTGGGGAAGTTTACGCTGTGATAATTTCATCAGTTGAAGCAGCTAAAGAAGTTCTCAGAACACAGGATGTGAATTTC
GCTGATAGACCGCCCGTCCTAGTATCCGAAATCGTTCTCTACAATCGTCAGGATATCGTATTTGGTTCCTACGGAGATC
ATTGGCGACAGATGAGAAGAATCTGCACAATGGAATTGCTTAGTATAAAACGTGTTCAATCATTCAAATCTGTCCGGGA
AGAAGAGGTTTCGAATTTTATCAAATTGCTTTATTCGGAAGCAGGACAGCCGGTCAATCTTACGGAGAAGTTGTTTGCT
TTGACGAATTCGATTATGTTGAGGACTTCAATTGGTAAGAAATGCAAAGATCAAGAGACCCTTTTGAGAGTAATTGAAG
GAGTTGTGGCGGCCGGAGGAGGTTTCAGTGTTGCTGATGTGTTTCCTTCCGCCGTGTTCCTTCATGATATCACCGGAGA
CAAGTCTGGCCTTGAGAGTTTGCGCCGAGATGCAGATTTGGTACTTGATGAGATCATCGGAGAACATAGAGCTAATAGA
TCAGGTAATGGTGGTGATGAAGGCGAAGCTGAAAATCTTTTGGATGTTCTTTTGGATCTTCAGGAAAATGGAAATCTTG
AAGTCCCTTTAAACGATGACAGCATCAAAGCTACAATTCTGGATATGTTTGGGGCAGGAAGTGACACATCCTCCAAATC
TACAGAATGGGCATTATCAGAGTTACTAAGACACCCAGTAGCAATGAAGAAAGCACAAGATGAAGTAAGGAAAGTTTTC
AGTGAAAATGGAAATGTAGAAGAAGAAGGACTTAACCAATTAAAATACTTGAAATTAGTCATCAAGGAAACTCTCAGAT
TACACCCAGCAATCCCTTTAATTCCAAGAGAATGCAGAGAAAAGACTAAAGTCAATGGATATGACATTCTTCCAAAAAC
TAAGGCACTTGTGAATATTTGGGCAATTTCCAGAGATCCAACAATATGGCCAGAAGCAGACAAATTCATCCCAGAAAGA
TTTGAAAATAGTTCAATGGATTTCAAAGGAAATCACTGTGAATTTGCTCCATTTGGTTCAGGAAAAAGGATATGCCCAG
GCATGGCTTTGGGGATAACTAATCTTGAACTTTTCCTTGCACAACTGTTATATCATTTTGACTGGAAACTTACCGACGG
AAAAGACCCTCGAAATCTTGACATGAGTGAAGTAGTAGGTGGTGCAATTAAAAGAAAAATAGATCTCAATTTGATTCCT
ATTCCATTCCATCCTTAA

SEQ ID NO: 6, *Jatropha curcas*

>Jcu2819
ATGTCGCTGCAACCAGCAATTTTACAGGGAAATACCTGTAAACAGTATTTTCATCCATTATCAAGCATATCCTCTACCA
GATGGGTTGGCAATTGCAACCGTTTCGCTTTTCTTTCTCCGGCTAAGCCAACTGCAAACAGAGCACCGCAAGCGTCTTT
ATCATCAAAACTGCAGCCAGTAGTTCGTCTGCTGACTAAATTCCCTGCTTCTGGTTTCTTGGCCATGAATCAATCTGTT
GATCAATTTGCTTCAACTACCACAAGTCTTACCAAAATATTCAACAAAATAGGAAAACCTATCCAATCATCTCCATTTC
TTGTAAGCGTTCTTCTTTTGATGTTTATGGCATCAAAAATACAGAACCAACAAGAAGAAGATGATAACTCCATAAATCT
TCCTCCAGGACCATGGAGATTACCTTTCATAGGTAACATTCACCAACTTGCTGGCCCCGGTCTACCCCATCACCGTCTA
ACAGACTTAGCCAAAACTTACGGACCTGTAATGGGTGTTCACCTTGGCGAAGTTTACGCTGTTGTTGTTTCCTCCGCAG
AAACATCCAAAGAAGTATTAAGAACGCAGGATACAAATTTCGCTGAAAGACCTTTAGTTAATGCAGCGAAAATGGTCCT
ATATAACAGAAACGACATTGTTTTTGGGTCGTTTGGAGATCAATGGCGACAAATGAGAAAAATCTGCACATTAGAATTA
CTTAGTGTAAAACGTGTGCAGTCATTCAAATCAGTAAGAGAAGAAGAGATGTCAAGTTTTATTAAATTTCTTTCTTCGA
AATCTGGTTCGCCGGTAAATCTTACCCATCATCTGTTTGTTTTGACAAACTATATTATTGCAAGAACTTCCATTGGTAA
GAAATGTAAGAATCAAGAAGCGCTTCTTAGAATTATAGACGACGTCGTTGAGGCGGGAGCTGGATTTAGTGTTACTGAT
GTCTTTCCATCGTTTGAAGCGCTTCATGTGATTAGTGGAGATAAGCATAAATTTGATAAATTGCATAGAGAAACTGATA
AGATACTTGAAGATATCATAAGTGAACATAAAGCCGACAGGGCAGTATCTTCCAAGAAAAGTGATGGTGAAGTTGAGAA
TCTTCTTGATGTTCTTTTGGATCTTCAAGAAAATGGAAACCTTCAATTTCCCTTAACAAATGATGCCATCAAAGGAGCC
ATTCTGGATACATTTGGCGCAGGCAGCGACACATCCTCAAAAACAGCAGAATGGACATTATCGGAGCTGATCAGGAACC
CAGAAGCAATGAGAAAAGCACAAGCAGAAATAAGGAGAGTTTTCGATGAAACAGGATATGTTGATGAAGACAAATTTGA
GGAATTAAAATACCTGAAACTAGTTGTGAAGGAAACTTTGAGATTACATCCTGCTGTGCCATTAATTCCAAGAGAATGC
AGAGGAAAAACTAAGATTAATGGGTATGACATTTTCCCCAAGACCAAGGTATTGGTGAACGTCTGGGCAATTTCAAGAG
ATCCTGCAATTTGGCCAGAGCCTGAAAAGTTCAATCCAGAAAGATTCATCGATAATCCGATTGATTATAAGAGTATTAA
CTGCGAGCTAACACCTTTTGGTGCGGGAAAGAGAATTTGCCCTGGAATGACATTAGGGATAACAAATCTTGAACTTTTC
CTGGCAAATTTGCTATATCATTTTGATTGGAAACTTCCTGACGGGAAGATGCCAGAGGATCTTGATATGAGTGAATCAT
TTGGTGGAGCAATTAAAAGAAAAACAGATCTGAAGTTGATTCCTGTTCTGGCGCGCCCTTTGACTCCAAGAAACGCCAA
CAGTGGCAACACTTTCACTACAACAGACGCCGACTCTCCTGCATCAATGTGCCCACACTTAAAAGCATTATGA

Fig. 8

SEQ ID NO: 7, *Jatropha gossypifolia*

>Jgo02184
ATGTCACTGCAACCAGCAGTTTTACAGGCAAATACCTGTAAACAGTATTTTCATCCATTATCAAGCATATCCT
CTACCAGATGGGTTGGCAATTGCAACCGTTTCGCTTTCCTTTCTCCGGCTAAGCCAACTGCTAACAGAGCACC
GCAAGCTTCTTTATCATCAAAACTGCAGCCAGTAGTTCGTCTGCTGACTAGATTCCCTGCTTCTGGTTTCTTG
GCTATGAATCAATCTGTCAATCAATTTGCTTCAACTACAACAAGTCTTGCCAAAATATTCGACAAAATAGGAA
AACCTATCCAATCATCTCCATTTCTTCTAAGTGTTCTTCTTTTGATGTTTATGGCATCAAAAATACAGAACCA
ACAAGAAGAAGATAATAACTCCATAAATCTTCCTCCAGGACCATGGAGATTACCTTTCATAGGTAACATTCAC
CAACTTGCTGGCCCCGGTCTACCCCATCACCGTCTAACAGACTTGGCCAAAACTTATGGACCTGTAATGGGTG
TTCACCTTGGCGAAGTTTACGCTGTTGTTGTTTCCTCCGCAGAAACATCTAAAGAAGTATTAAGAACACAGGA
TACAAATTTCGCTGAAAGACCTTTGGTTAATGCAGCGAAAATGGTCCTATATAACAGAAACGACATTGTTTTT
GGGTCGTATGGAGATCAATGGCGACAAATGAGAAAAATCTGCACATTGGAATTACTTAGTTTAAAACGTGTGC
AGTCATTCAAATCAGTAAGAGAAGAAGAGATGTCAAGTTTTATTAAATTTCTTTGTTCGAAATCTGGTTCGCC
GGTAAATCTTACCCATCATCTGTTTGTTTTGACAAACTATATTATTGCAAGAACTTCCATTGGTAAGAAATGT
AAGAATCAAGAAGCGCTTCTTAGAGTTATAGACGACGTCGTTGAGGCAGGAGCTGGATTTAGTGTTACTGATG
TCTTTCCATCGTTTGAAGCCCTTCATGTGATTAGTGGAGATAAGCATAAATTTGATAAATTGCATAGAGAAAC
TGATAAGATACTTGAAGATATCATAAGTGAACATAAGGCCGACAGGGCAGTATCTTCCAAGAAAAGTGATGGT
GAAGCTGAGAATCTTCTTGATGTTCTTTTGGATCTTCAAGAAAATGGAAATCTTCAATTTCCCTTAACAAATG
ATGCCATCAAAGGAGCCATTCTGGATACGTTTGGCGCAGGCAGCGACACATCCTCAAAAACAGCAGAATGGAC
GTTATCAGAGTTGATCAGGAACCCAGGAGCAATGAGAAAAGCACAAGAAGAAATAAGGAGAGTTTTCGATGAA
ACAGGATATGTTGATGAAGACAAATTTGAGGAATTAAAATACCTGAAACTAGTTGTGAAGGAAACTTTGAGAT
TACATCCTGCTGTGCCATTAATTCCAAGAGAATGCAGAGGAAAAACTAAGATTAATGGGTATGACATTTTCCC
CAAGACTAAGGTCTTGGTGAACGTCTGGGCAATTTCAAGAGATCCTGCAATTTGGCCAGAGCCTGAAAAGTTC
AATCCAGAAAGATTCATCGATAATCCGATTGATTATAAGAGTATTAATTGCGAGCTAACACCTTTTGGTGCAG
GAAAGAGAGTTTGCCCTGGAATGACATTAGGGATAACAAATCTTGAACTTTTCCTGGCAAATTTGCTATATCA
TTTTGATTGGAAACTTCCTGACGGAAAGATGCCAGAAGATCTTGATATGAGTGAATCATTTGGTGGAGCAATT
AAAAGAAAAACAGATCTGAAGTTGATTCCTGTTCTGGCTCGTCCTTTCAATCCAACTAACGCCAACAATGGCA
ACACTTTCACTACAACAGACGCCAACTCTCCTTCATCAATGTGCCCACACTTAAAAGCATTATGA

SEQ ID NO: 8

>CYP726A4
ATGGAGCTTCAATTTCAAATCCCCTCTTATCCAGTCCTTTTCTCCTTCTTCATCTTCATCTTTATACTAATCAAAATAG
TAAAAAAACAAACTCAAAACTCTATCTCCCCTCCGGGACCATGGAAATATCCTATTTTGGGAAACATTCCACAATTAGC
TGCCGGCGGAAAGCTTCCTCATCACCGGTTAAGAGATTTAGCAAAAATCCATGGTCCGGTGATGAACATTCAACTCGGG
CAAGTCAAGTCCATTGTCATTTCCTCCCCGGAAACTGCCAAAGAGGTGTTGAAAACTCAGGATATCCAGTTCGCCAATA
GGCCTCTTCTTCTCGCTGGAGAAATGGTTCTTTACAACCGGAAAGATATCTTGTACGGTCTTTACGGGGATCAATGGCG
ACAAATGAGGAAAATATGCACTTTGGAGTTACTAAGTGCTAAGCGAATTCAATCATTCAAGTCAGTGAGAGAACAAGAA
GTCGAGAGCTTCATTCGGTTGCTCCGATCAAAGGCGGGGTCCCCAGTGAATCTCACGACAGCGGTGTTTGAGTTGACGA
ATACTATTATGATGATCACGACGATTGGTGAGAAATGCAAGAATCAAGAGGCGGTGATGAGTGTGATTGATCGAGTGAG
TGAGGCTGCAGCGGGGTTTAGTGTTGCCGACGTATTTCCATCGCTAAAATTTCTTCATTATCTGAGTGGAGAAAAGGGG
AAGTTGCAGAAGTTGCATAAGGAGACTGATGAGATACTTGAAGAGATTATAAGTGAACATAAAGCTAATGCTAAGATTG
GAAGCCAAGCTGATAATCTTTTGGATGTTTTGTTGGATCTTCAGAAAAATGGGAATCTTCAAGTTCCATTGACTAATGA
TAATATCAAAGCTGCCACTCTGGAAATGTTCGGAGCTGGTAGCGACACATCCTCCAAAACTACAGACTGGGCAATGGCG
CAACTAATGAGGAAGCCATCAGCAATGAAAAAGGCACAAGAAGAGGTCAGGCGCGTCTTTAGCGACACGGGAAAGGTAG
AGGAATCAAGAATCCAAGAACTAAAATACTTGAAATTAATCGTTAAAGAAACATTGAGATTACATCCTGCCGTGGCATT
GATTCCTAGAGAATGCCGAGAGAAAACTAAAATCGAGGGATTTGATGTTTATCCTAAAACAAAAATTCTTGTGAATCCT
TGGGCGATTGGAAGAGATCCGAAAGTTTGGAGTGACCCCGAAAGTTTCAACCCAGAAAGATTTGAAGATAGTTCAATAG
ACTATAAGGGTACAAATTTCGAACTAATTCCGTTTGGTGCAGGAAAAAGAATATGTCCAGGAATGACTTTGGGCATAGT
GAATTTAGAGCTTTTCCTTGCAAATTTGTTATATCATTTTGATTGGAAATTCCCAAATGGAGTCACAGCTGAGAATCTT
GATATGACTGAAGCCATTGGTGGTGCTATCAAGAGAAAACTAGACCTTGAGTTGATTCCTATTCCATACACATTAAGTT
AA

Fig. 9

SEQ ID NO: 9, *Ricinus communis*

>CYP726A15
ATGTCATTGCAACCTGCACCTGTTTCACAATCCAACTTTCTTTACAAAAAGTTCCACCAATATTACGTGCACCCACTA
CCAAGTCTAGTGGTAGCAGTCGTTCCTCTTTCTTTTCCTCATCAGTTAAGTTAGCTGCTAGACCACCGCAACCGCAAGC
TTGCTTATCGTTGAACAAAAACGATGACTCCAATACCTCCGCCTCCAGTCTTCCTCCAGGACCATGGAAGTTGCCTCTG
CTAGGTAACATTCACCAGCTAGTCGGAGCTCTTCCCCATCACCGCCTAAGAGACTTGGCTAAAGCTTACGGGCCTGTCA
TGTCTGTTAAACTCGGAGAAGTTTCTGCTGTCGTAATTTCATCAGTAGATGCTGCCAAAGAGGTACTCAGGACTCAGGA
TGTCAACTTCGCAGATAGACCCCTTGTCCTGGCAGCAGAAATTGTGCTATATAATCGTCAGGACATTGTATTTGGGTCA
TATGGAGAGCAATGGAGACAAATGAGAAAGATTTGCACACTGGAGTTGCTTAGTATTAAGCGCGTTCAATCTTTCAAAT
CGGTCAGGGAAGAAGAGCTTTCTAATTTTATCAGATACCTTCACTCAAAAGCTGGAACTCCTGTTAACCTTACTCATCA
CTTGTTTTCTTTAACAAATTCCATTATGTTTAGAATTTCCATTGGTAAGAAATACAAAAATCAAGATGCACTTTTGAGA
GTCATCGATGGCGTCATTGAAGCTGGAGGAGGTTTCAGTACTGCTGATGTGTTTCCTTCCTTTAAATTCCTTCACCACA
TTAGCGGAGAGAAGTCTAGCCTTGAGGACTTGCACCGAGAAGCAGACTATATACTAGAAGATATCATAAATGAACGCAG
AGCCTCCAAGATTAATGGTGATGATCGAAACCAAGCTGATAATCTCTTAGATGTTCTTTTAGATCTTCAGGAAAACGGA
AATCTCGAAATCGCTCTAACCAATGACAGCATCAAAGCAGCCATTCTGGAAATGTTTGGTGCTGGCAGCGACACATCCT
CAAAAACCGCTGAATGGGCACTGTCAGAGTTGATGAGGCACCCAGAAGAAATGGAAAAGGCACAAACAGAAGTAAGGCA
AGTCTTTGGTAAAGATGGAAATTTGGATGAAACTCGACTTCATGAATTAAAATTCTTGAAGTTAGTTATCAAAGAAACC
TTAAGATTGCATCCTCCAGTAGCATTGATTCCAAGAGAATGCAGGCAAAGGACTAAGGTTAATGGATATGACATAGATC
CCAAAACTAAGGTTCTCGTCAATGTTTGGGCAATTTCAAGGGATCCAAATATATGGACTGAAGCAGAGAAATTCTACCC
GGAAAGATTTCTTCACAGTTCCATTGATTACAAGGGCAATCATTGTGAATTTGCTCCATTTGGATCTGGAAAAAGAATA
TGCCCTGGTATGAACTTAGGTTTAACTAATCTTGAACTCTTCCTTGCCCAATTACTGTATCACTTTAACTGGGAATTTC
CTGATGGAATAACACCTAAGACTCTTGATATGACAGAATCTGTTGGTGCTGCAATTAAAAGAAAGATAGATCTTAAATT
GATTCCTGTTCTATTTCATCCTTAA

SEQ ID NO: 10, *Ricinus communis* 5-keto-casbene 7,8-epoxidase

>CYP726A16
ATGGAAAGTGCTGCTCACCAATCCTACTTCCATATGTTCCTGGCTATGGAGCAGCAAATCCTTTCATTTCCAGTCCTTT
TAAGCTTTCTTCTTTTCATTTTCATGGTATTAAAGGTGTGGAAGAAAAACAAGGACAATCCAAACTCGCCTCCGGGGCC
AAGGAAGTTGCCTATCATAGGCAACATGCACCAGCTAGCTGGTAGTGATCTGCCCCATCACCCTGTAACAGAATTGTCA
AAAACTTACGGACCAATAATGAGCATTCAACTTGGCCAAATATCGGCCATCGTTATTTCTTCAGTAGAAGGAGCCAAAG
AAGTGCTGAAGACCCAAGGTGAGCTGTTCGCTGAAAGACCTCTTCTCTTGGCAGCAGAGGCAGTGCTTTATAATCGTAT
GGACATTATATTCGGTGCATACGGTGATCATTGGAGGCAATTGAGAAAATTGTGCACCTTAGAGGTGCTTAGTGCAAAA
CGAATCCAATCATTCAGTTCACTCAGACAAGAAGAACTTTCACATTTTGTCCGCTTCGTTCATTCCAAAGCAGGAAGCC
CAATCAATCTTTCCAAGGTGCTGTTTGCTTTAACAAATTCTATCATTGCAAGAATCGCCACAGGTAAGAAATGCAAAAA
CCAAGATGCCCTCTTAGATCTTATCGAAGACGTTATTGAGGTATCTGGAGGTTTCAGCATTGCCGATTTATTTCCTTCG
TTGAAATTCATTCACGTCATCACTGGTATGAAGTCTAGACTGGAAAAATTGCATCGGATAACAGATCAGGTACTTGAAG
ACATCGTCAATGAACATAAAGCCACCAGGGCAGCCTCCAAGAATGGTGGTGGTGACGATGATAAAAAAGAAGCCAAAAA
TCTTCTAGATGTTCTTTTGGATCTTCAAGAAGATGGAAGCCTTCTTCAAGTTCCTTTAACCGACGATAGCATCAAAGCA
GCCATTCTGGAAATGCTTGGCGGTGGAAGTGACACATCTGCAAAAACCACAGAATGGGCAATGTCCGAGATGATGAGGT
ACCCAGAAACAATGAAAAAAGCACAAGAAGAAGTGAGGCAAGCGTTCGGTAACGCGGGAAAGATTGATGAAGCACGCAT
CCATGAGTTGAAATACTTGAGGGCAGTTTTCAAAGAGACTTTGAGATTACATCCCCCGCTAGCGATGATACCGAGAGAA
TGCAGGCAAAAGACTAAGATTAATGGATATGATATCTATCCCAAAACTAAAACGTTGATCAATGTATATGCAATCGGAA
GGGATCCCAATGTTTGGAGTGAACCTGAGAAGTTCTATCCGGAAAGACATCTTGATAGTCCAATCGACTTCAGAGGCAG
TAACTTTGAACTAATTCCATTCGGTGCAGGGAAAAGAATATGTCCTGGCATGACATTAGCTATAACTACTGTGGAGCTG
TTTCTCGCTCATCTTCTATACTATTTTGACTGGAAGTTTGTTGATGGAATGACGGCTGATACTCTTGATATGACTGAAT
CCTTCGGAGCTTCAATTAAAAGAAAAATAGATCTCGCCCTGGTTCCCATTCCCGTCAGTCCTTTACCATAA

Fig. 10

SEQ ID NO: 11, *Ricinus communis*

>CYP726A13
ATGGACAAGCAAATCCTATCATATCCAGTGCTCCTGCTGAGCTTCCTCCTTTTTATCTTAATGGTGTTAAGGATATGGA
AGAAAAGCAAGGGCAGCTTCAACTCACCTCCGGGACCATGGAAGTTACCTCTCATAGGCAACATGCACCAACTCATTAC
TCCTCTGCCCCATCACCGCCTGAGAGAATTGGCCAAAACTCATGGGCCAGTTATGAGTATTCAACTTGGCCAAGTTTCG
GCCGTCGTCATTTCCTCAGTAGAAGCAGCTAAGCAAGTGCTCAAAACCCAAGGTGAATTGTTCGCTGAAAGACCCAGCA
TCCTGGCATCAAAAATAGTGCTTTATAATGGTATGGACATAATATTTGGGTCATACGGTGACCACTGGAGACAAATGAG
GAAAATTTGCACCTTCGAGCTGCTCAGTCCAAAACGCGTCCAGTCCTTCAGTTCGGTCAGGCAAGAAGAACTTTCCAAT
TATGTCAGGTTCCTCCATTCCAATGCCGGAAGCCCAGTCAATCTGTCCAAGACCTTGTTTGCTTTAACAAATTCTGTTA
TCGCAAAAATCGCAGTAGGTAAGGAATGCAAAAACCAGGAAGCCCTCTTAAATCTTATCGAAGAAGTCCTTGTGGCAGC
AGGAGGTTTCACTGTTGCTGATTCATTTCCATCCTATAATTTCCTTCACGTCATCACTGGTATGAAGTCTAACCTGGAG
AGATTGCACCGGATAACAGATAAGATCCTTGAAGACATCATAACTGAACATAAAGCCCCCAGGGCACTCTTCAAGCGTG
GTGGCGATGAGGATAAAAAAGAAGCCGAAAATCTTTTAGATGTTCTTTTGGGTCTTCAGGAACATGGAAACCTTAAAGT
CCCTTTAACCAATGAGAGTGTCAAGTCAGCCATTCTGGAAATGCTTTCCGGCGGGAGCGACACATCTGCAAAAACAATA
GAATGGGCAATGTCAGAGTTGATGAGGAGTCCAGAAGCAATGGAAAAGGCACAAGAAGAAGTGAGAAGAGTGTTTGGTG
AATTGGGAAAGATCGAGGAATCACGCCTCCATGAATTAAAGTACTTGAAATTAGTTATCAAAGAGACGTTGAGATTACA
TCCCGCACTAGCCTTGATTCCAAGAGAATGCATGAAAAGAACTAAGATTGATGGATATGATATTTCTCCCAAAACTAAA
GCCTTGGTCAATGTATGGGCAATCGGAAGAGATCCCAGCGTTTGGAATGAACCTGAAAAGTTTTTCCCGGAAAGGTTTG
TCGACAGTTCGATTGATTTCAGAGGTAATAATTTTGAACTACTTCCATTTGGTTCAGGAAAGAGGATATGTCCTGGTAT
GACATTGGGTTTAGCCACTGTAGAGCTTTTCCTCTCCTACCTGCTGTATTATTTTGATTGGAAGCTTGTCGGTGGAGTG
CCTCTTGACATGACCGAAGCTTTTGCTGCTTCACTTAAAAGAAAAATAGACCTCGTTTTAATTCCCATTTCAGTCGGCC
CTTCACCAACAACGGACTGA

SEQ ID NO: 12

>CYP726A10
ATGGAGCTGCAAATCTTTTCTTTTCCAGTTCTTCTGAGCTTCTTCCTTTTTATTTTCATGGTCTTGAGGA
TATGGAAGAATTCCAACAAAAAATTGAACCCCCCTCCAGGACCCTGGAAGCTACCTCTTCTAGGAAATAT
TCATCAACTAGCCACCCCATTACCCCATCAACGCCTCAGAGATTTGGCCAAAAGTTTTGGCCCAGTGATG
AGCATCAAACTTGGGGAAATTTCAGCTGTGATAATTTCATCAGCAGAAGCAGCTCAAGAAGTACTAAAAT
CTCAGGATGTCACCTTTGCTGAAAGGCCTGCATCTCTTGCTTCGAAATTAGTACTTTACAATCGCAACGA
TATTGTCTTTGGGGCTTATGGACCACAATGGAGACAAACGAGAAAACTGTGCGTGCTGGAGCTGCTAAGT
GCCAAACGCATTCAATCATTCAAATCTGTAAGGGAAGAAGAGGTAGACGAGTTTGCCAAGTTCGTTTATT
CGAAAGGTGGGACGCCAGTCAACCTTACTGATAAGCTGTTTGCTTTAACAAATACTATCATGGCAAGGAC
CACCATAGGTAAGAAATGCAGAAGTGAAAAAGATCTCTTGAGATGTATTGATGGCATCTTTGAAGAAGCA
GGGGTTTTCAATCTTGCCGATGCGTTTCCTTCCTTTACTTTGCTTCCTGTAATCACTGGAGCCAAGTTTA
GACTTGAGAAATTGCATAGAGAGACAGACAAGATACTTGAAGACATCTTACGTGAACACATAGCTTCCAA
GGCTGCTTCAGACAAAGATACCCGGAATCTTTTACATGTTCTTTTGGATCTTCAGGAAAGTGGAAACCTT
GAAGTCCCTATTACCAACGACAGCATCAAAGCTACTATTCTGGATATATTTATCGCAGGGAGCGACACAT
CTGCAAAAACTGTAGAGTGGGCAATGTCAGAGTTGATGCGAAACCCAAAATTAATGAAAAGAGCACAAGA
AGAAGTGAGGCAAGTCTTTGGTGAGAAGGGGTTTGTTGATGAAGCAGGGCTTCAGGATTTAAAATTCATG
AAGTTGATTGTTAAAGAAACTTTGAGATTGCATCCTGTCTTTGCAATGTTTCCAAGAGAATGTAGGGAAA
AGACAAAAGTCAATGGATATGACATTTCTCCTAAGACTACAATGCTCATCAATGTGTGGGCAATTGGAAG
GGATCCTAATGTCTGGCCTGATGCAGAGAAGTTCAACCCAGAAAGATTTCTTGATAGTTCAATTGATTAC
AAAGGTAATAATGCTGAAATGATTCCATTTGGTGCAGGAAAAAGGATATGTCTTGGGATGACATTAGGTA
CACTTATTCTAGAGCATTTCCTTGCAAAACTACTCTATCATTTTGATTGGAAATTTCCTGATGGAGTAAC
CCCTGAGAATTTCGACATGACAGAACATTATAGTGCTTCGATGAGAAGGGAAACCGACCTTATCTTAATT
CCTATTCCAGTCCATCCTTTGCCTACACACTAA

Fig. 11

SEQ ID NO: 13

>CYP726A11
ATGGAGCAGCAGATCCTCTCATTTTCTGTCCTTTCATGTCTCATTCTTTTTCTCTTAATGGTCATTAATA
TTTTGAAAAATTACAGTAAAGATTTTACCCCTCCTCCAGGACCATGGAAGCTACCCTTTCTTGGTAATAT
TCACCAGCTAGCTACCGCACTACCTCATCGTCGCCTACGAGATTTGGCCAAAACTTATGGTCCTGTAATG
AGCATTAAGCTTGGAGAAATTTCTTCTATCGTAATCTCATCAGCAGAAGCAGCTCAAGAAGTACTGAAAA
CTCAGGATGTCATATTTGCAGAAAGACCAATAGCTCTTGCAGCCAAAATGGTGCTTTACAATCGTGATGG
CATTGTCTTTGGTTCCTATGGCGAGCAACTCAGGCAGTCAAGGAAAATTTGCATATTGGAGCTGTTAAGT
GCGAAACGCATTCAGTCATTCAAATCAGTAAGGGAAGAAGAGGTATCTAACTTTATCAGTTTCCTTAATT
CGAAAGCGGGGACGCCTGTCAACCTTACTGACAAGCTGTTTGCATTAACTAATTCTATCATGGCAAGAAC
CTCAATTGGTAAGAAATGCAAGAATCAAGAAGATCTCTTAAGATGTATTGATAACATTTTTGAGGAAGCA
ACAGTTTTCAGCCCTGCCGATGCGTTTCCTTCCTTTACTTTGCTTCATGTAATCACCGGAGTCAAGTCTA
GACTTGAGAGATTGCATCAACAAACAGACAAGATACTTGAAGACATTGTAAGTGAACACAAAGCTACTAT
GGCTGCTACCGAGAATGGAGACCGGAATCTCTTGCATGTTCTTTTGGATCTTCAGAAAAATGGAAATCTT
CAAGTTCCTTTAACCAACAACATCATCAAAGCAATTATTCTGACTATATTTATCGGAGGGAGTGACACAT
CGGCAAAAACTGTAGAATGGGTAATGTCAGAGTTGATGCATAACCCTGAACTGATGAAAAAAGCACAAGA
AGAAGTGAGGCAAGTCTTTGGTGAAAAGGGATTTGTTGATGAAACAGGGCTGCATGAATTAAAATTTCTC
AAGTCAGTTGTTAAGGAGACTCTGAGGTTGCATCCTGTTTTCCCATTAGTTCCTAGAGAGTGTAGGGAAG
TAACTAAGGTGAATGGATACGACATTTATCCTAAAACTAAGGTGCTCATCAACGTGTGGGCTATTGGAAG
GGATCCTGATATCTGGTCCGACGCAGAAAAGTTCAATCCTGAAAGATTTCTTGAAAGTTCGATTGACTAC
AAAGATACTTCTTCTGAAATGATCCCATTTGGTGCAGGAAAGAGGGTATGTCCTGGCATGTCATTAGGCC
TACTAATTCTTGAGCTTTTTCTTGCACAGCTACTCTATCATTTTGACTGGAAACTTCCTGATAGAGTTAC
TCCGGAGAATTTTGACATGAGCGAATATTATAGTTCTTCATTGAGAAGAAAACATGACCTTATCTTGATT
CCCATTCCTGTCCTTCCTTTGCCTATAGAATAA

SEQ ID NO: 14

>CYP726A12
ATGGAGCAGCAAATTCTCTCATTTCCAGTCCTTCTAAGCTTCTTCCTTTTTATCTTCATGGTCTTGAAAA
TACGGAAGAAATACAACAAGAATATCAGCCCTCCTCCAGGACCATGGAAGCTACCTATCCTAGGTAACAT
TCACCAGCTAATTAGCCCACTACCCCATCATCGCCTAAGAGACTTGGCCAAAATTTATGGGCCTGTGATG
AGTATTAAACTTGGCGAGGTTTCTGCTGTGGTAATTTCTTCCGCGGAAGCAGCAAAAGAAGTACTAAGAA
CCCAGGATGTCAGTTTCGCTGATAGACCCCTTGGCCTCTCAGCGAAAATGGTGCTTTATAATGGTAACGA
TGTTGTTTTTGGTTCTTATGGAGAACAATGGAGACAACTGAGAAAAATTTGCATATTGGAGCTGCTTAGT
GCAAAACGTGTTCAGTCTTTCAAATCGTTAAGGGAAGCAGAGGTATCAAATTTTATTCGTTTTCTTTATT
CGAAAGCAGGGAAGCCTGTCAACCTTACTCGCAAGCTGTTTGCTTTAACAAATACTATTATGGCGAGAAC
CTCCGTAGGTAAACAATGTGAAAATCAAGAAGTTCTCTTAACAGTTATAGATAGGATTTTTGAAGTATCA
GGAGGTTTCACTGTTGCTGATGTTTTTCCTTCATTTACTTTGCTTCATTTAATTACTGGGATCAAGTCTC
GACTTGAGAGGTTGCATCAAGACACAGATCAGATTCTTGAAGACATCATAAATGAGCATAGAGCTTGTAA
GGCCGTATCCAAGAATGGTGATCAGAATGAAGCTGACAATCTTTTAGATGTTCTTTTGGATCTTCAGGAA
GATGGAAACCTTCGAGTCCCTTTAACCAATGACAGCATCAAAGGAACAATTCTGGATATGTTCGCTGGTG
GGAGTGATACAACTTCAAAAACTGCAGAATGGGCAGTGTCAGAATTGATGTTCAACCCAAAAGCAATGAA
AAAAGCACAAGAAGAAGTGAGGCGAGTCTTTGGCCAAAAAGGGATTGTTGATGAATCAGGATTTCATGAA
TTGAAATTCTTGAAGCTGGTTATTAAAGAAACTCTGAGATTGCATCCAGCATTGCCCTTAATTCCAAGAG
AGTGTATGAACAAGTCTAAGATCAATGGATACAACATTGATCCAAAAACCAAGGTTCTGATCAATGTGTG
GGCAATTGGAAGAGATTCTAATATCTGGCCTGAAGCAGAGAAATTCTATCCAGAAAGATTTCTGGATAGT
TCAATAGATTATAAGGGCACTAGTTATGAGTTCATTCCATTTGGTGCAGGAAAGAGGATATGTCCTGGCA
TGATGTTGGGTACAACTAATCTTGAGCTTTTTCTTGCCCAACTACTATATCATTTTGACTGGCAATTCCC
TGATGGAGTGACACCTGAGACTTTTGACATGACAGAGGCTTTTAGCGGTTCAATTAACAGAAAATATGAT
CTTAATTTAATTCCCATTCCGTTCCATCCCTTGCGTGTAGAATAG

Fig. 12

*SEQ ID NO: 15, Euphorbia peplus*

>CYP726A3
ATGGATCTTGAAATGCCCTCTTTTCTCATCCTCTTTAGCTTTCTCATTTTAACATGGATCATATGGAAGAAGATGAATT
CCAACTCAGTTCCTCCTCCGGGGCCTTGGAAGTTGCCTCTTCTAGGCAACATTCTTCAATTACGCGGCGGTCCAGCCAA
TCACCGCCTCTGCGATTTGGCTAAAGTGTACGGTCCGGTGATGAGCATTCAACTAGGCCAGAATCCTGCGGTTGTGCTT
TCTTCACCTGAAGCAGCCGAACAAGTCTTCAAAATTCAGGGCGACCTATTTAACAACCGTCCACCAGCCCTCTCAGGTA
AAATTTTGTTTTACAATAACAGCGACATGACATTCACGCCATACGGAGATCATTGGCGACAAATTAGAAAAATTACCGT
GATGGAATTCCTTAGTCCGAAACGAGTTTTATCGTTTCGATCAATACGTGAAGAACAAGTATCAAATTTCATCAAATTC
CTTCGTACGAAAGGCGGATCTGCGATCAATTTCCCGAAAGCCCTCTCCGAGTTGACAAGTAGGATTATGCTAATAACCT
TACTTGGTAACAAAGATGAAAATGAGGAAATTGTATTACCAGCGATAGAAAGAGTGATAGAGACTGCAAATAAAGGTGC
TGCTTCGGATACCTTTCCGACGTTAAAATTCTTCCTCGACTTTCTCACCGGAGACAAGTCAAGAATGGAAAAAGTGTTA
CAAGAGACGGATATCATACTTGAAGCCATCATAAATGAACACAAAAAAAAAGGTACCTCAGAACACAATTATTTAGATT
TTCTGCTGGATAAACAGAAAAAGGGAGACCTCCAATTGCCATTAACAAACGAAGCCATCAAAGCAAATCTTATGGCTAT
GTATGCGGGCGGGAGTGAGACATCATCTAAACTCATAGAATGGACATTCGCGGAGATGATGAAGAACCCTGAAACGATG
CGAAAAGCGCAAGAGGAGGTGAGAAGAGTTTTTGGTGACAAAGGAAAAGTTGAGGAATCAAGAATTCAAGAATTGAAAT
ACTTGAAATTAGTTCTTAAAGAATCTTTCAGAATACATCCTCCGTCGACCTTGATTACAAGAGTATGCCAAGAAAGAAC
AAAAATCAACGGTTACGACATTCATCCCAAAACTACAATTCTTATCAATGTGTGGACGATGGGAAGAGATCCGAATCTT
TGGAAAGAACCCGAAAAGTTCCATCCAGAAAGATTTGAAGATAGTAAAATTGATTTCAGAGGAGCAAATATGGAATTAA
CACCATTTGGTGTAGGAAAAAGAATGTGTCCTGGAATTACTCTATCTACAACTTATGTGGAGTTTCTGCTGGCAAATTT
ATTGTATCATTTTGATTGGAAACTTCCTGACGGAGTCACACCGGCCACTCTCGATATGACTGAAACTCTGCGTGGCACG
CTCAAAAAAGTACAAGATCTTATTTTGATTCCCATTCCATTCTCCCCCCATCAAATTGCTTGA

SEQ ID NO: 16

>CYP726A5
ATGGAGTTCACTTTATCACTTAAAAAAATGGAGCTTCAAATCCTATCTTTTCCAATCCTCTTCCCCTTTCTCCTTTTCA
TCCTTACCTTCCTCACAATTATACGCCGGAAAAAGCAGAATCAAGACTGCAATTTTCCTCCGGGACCATGGCAGTTTCC
GATCATCGGAAACATTCCACAGTTGCTCGGAGGTCTCTTCCACCACCGTCTTTCCGATCTAGCCAAAATTCACGGCCCG
ATAATGAGCATTCAACAAGGACAAATCCCAGCTGTTGTAATCACTTCAGTTGAACTAGCCAAAGAAGTTCTCAAAACCC
AAGGTGAAATATTCGCCGGAAGGCCTCAAGCCCCGGCCGGAGATGTTTTGTATTACGATTGCAAGGATATCGTGTTCGC
CCCGTACGGGGATCACTGGAGACAGATGAGAAAGATCTGCACACTGGAGTTTCTCAGTCTGAAAAGAGTTCAGTCTTTC
AGATCCTTGAGGGAAGAAAACGTTTCAGGTTTTATTAAATTCCTCAGTACTAAAGCAAATTCGTCGGTAAATCTGACGA
AATCCGTCGGTAATTTGACAAGTTCAATTATGCTTATTAAAACTTATGGAAAATGTGATGAAAAATTGTTGGCTATGTT
GGAGAAAGTGAAACAAGCAGTTTTAGAGACGAGTAGTGGTACGGATCTGTTTCCGTCGCTGAAATTTATTCAATATATT
AATGGTGAGAAGTCAAGAATGGCAAGGGTGCAAAAGGAAATGGATAAAATGCTTGAACAGATTATTAAAGAACATAAAG
TTCAATATAAGTTTGGAGATAATAATCTTTTGCAGGTTTTGTTGGATCAACAGCAAAATGGAGATCTTGAACTTCCATT
GACAAATGAAATCATCAAAGCCAACATTATGGAAATATTTTTTGGTGGAAGCCATACTTCTTCTAAAACTGTGGAGTGG
GCAATGTCGGAGCTAATGAAGAACCCAGAATCAATGACAAAAGCACAAGCAGAGGTGAGACAAGTCTTCGGTGAGACGG
GAAATGTTGAGGAATCAAGAATGCAAGAAGTGAAATACCTCAAGTCAGTTATCAAAGAAACTCTAAGATTGCACCCTCC
GGCGACCTTTGTCACAAGAGAATGCAGACAAAAAACAAAAGTCAATGGTTATGATATTTACCCGAAGACAGTTGTTCAT
GTCAATACATATGCAATCTGTAGAGATCCTGATGTTTGGGTTGAACCTGAAAAGTTTTATCCTGAAAGGTTTGAAGAAA
ATCAAATAGATTATAAGGGTGCACATATGGAACTAATACCGTTTGGTGCAGGGAAAAGAATATGTCCAGGAATCTCATT
AGCCACAACATACGTTGAGGTTCTCCTTGCAAACTTGTTATATCATTTTGACTGGAAACTTCCATATGGAATGACTCCT
GCCAATCTTGACATGACGGAAATGCATTGCGGTGCCCTGGCTAGAAAACATGACCTTTGCTTGATTCCAATTCCGTTTT
CTAAAATTTGA

SEQ ID NO: 17

>CYP726A6
ATGAAAATGCTTGAGCAAATTCCCTCTCTTCCAATCATCTTTCCCTTGATCCTCTTCATTTTCATGCTCATAAAGTTAT
GGCAGAAAAAAAATCACAACTCAATCCGTCCACCCGGTCCAAGAAAATATCCATTCATAGGCAATCTTCCTCAATTACT
TGGTGCTCCAGTTCATCAAAGACTAGCAGATTTAGCCAAAACCTACGGCCCGGTAATGAGCATTCAACAAGGCCAGATC
CCGTCCGTCGTGCTTTCATCAGTCGAAACGGCCAAAGAAGTCCTCAAAATCCAGGGCGAAGAGTTTGCTGGAAGACCCT
CCACTATGGCTCTTGATATAACTTTTTACgACGCCCAAGATATTGCCTATACTGAATACGGTGATTATTGGAGACAAAT
GAAGAAAATTTCGACGCTAGAGTTTCTAAGCGCGAAACGAGTTCATTCTTTCAAACCAGTCCGGGAAGAACGAATTTCG
ATATTCCTCGATTCCCTTCGTTCAAAAGGCAGATCTCCGGTGAACCTGACGAGGACAATTTACGGGTTAACGAATTCGA
TCATTCAAATAACGGCGTTTGGGAAGAACTGTAAAACGAGAGAGAAATTGAATCTTGATAAGATTCGAGAGGCAGTTGT
GGATGGAACTATTGCTGATTTGTTTCCGAGATTTAAATTTATTGCGAGTTTGAGTGGAGCTAAATCAAGAATGATGAGG
GCTCATAAGGAGATTGATGTGGTTCTTGATGAAATCTTGGAAGAACATAAGGCTAATAAAAGCACCATTGGAAATAATC
TTATGCAAGTTCTTTTGGATTTTCAGAAAAATGGTGGCCTTCAAGTTCCATTGACAACTGATCAGATTAAAGCTAACAT
GCTGGAAATGTTTCTTTCAGGGAGCCATACGTCGTCAAAAATTACAGAGTGGACAATGGCGGAGCTAATGCGAGCACCA
GAAACAATGAGAAAAGCACAAGAAGAGGTGAGGCGAGTCTTCAGCGAAATTGGAAGAGTCGACGAATCAAGAATCCATG
AATGTAAATACGTGAAAAATGTCCTTAAGGAAGCTTTTAGATTACATCCTCCGGGGCCAATGGTTGTAAGGCAATGCAG
AGAAATAACTAAAGTCAATGGTTACGAGATTCTTCCTGGCACTACAGTTTTCATCAATGTCTGGGCAATAGGAAGAGAT
CCGGAGGTTTGGACTGAACCCGAAAAGTTCAACCCTGACAGATTCGAAGACAGTGAAATTGATTACAGAGGCGCACATA
TGGAACTAATACCATTTGGTGCAGGGAAAAGGATATGCCCTGGCTTGACGTTAGCCGTAGTTTACGTTGAGCTTTTGCT
TGCCAACTTATTATATCATTTCGATTGGGAATTTCCAGATGGAGTCACACAAAAGACTCTTGATATGACCGAATTTTTC
CGTGGTACACTCAACCGAAAAGAAGACCTTTACTTGATTCCCGTTCCATCTTCTTCATTGCCAAAGAATTAA

Fig. 13

SEQ ID NO: 18, *Jatropha curcas*

>CYP726A20
ATGGAACACCAAATCCTCTCATTTCCAGTTCTTTTCAGTTTGCTTCTTTTTATTCTCGTCTTACTAAAAGTATCCAAGA
AATTATACAAACATGACTCTAAACCTCCGCCTGGACCATGGAAATTACCTTTCATAGGTAACCTTATCCAGCTCGTCGG
TGACACACCTCATCGCCGGTTAACAGCCTTGGCCAAAACTTACGGACCTGTAATGGGTGTTCAACTTGGGCAAGTTCCT
TTCCTTGTCGTGTCCTCGCCGGAAACAGCTAAAGAAGTAATGAAAATACAAGATCCCGTTTTTGCAGAACGACCGCTTG
TCCTTGCAGGAGAAATAGTGCTTTATAACCGAAATGACATCGTTTTTGGGTCGTACGGAGATCAGTGGAGGCAAATGAG
AAAATTTTGCACGTTGGAATTACTTAGCACAAAACGAGTACAGTCGTTCCGACCCGTGAGAGAAGAAGAAGTTGCATCT
TTTGTAAAACTTATGCGTACAAAGAAAGGAACTCCTGTTAATCTTACTCATGCTTTATTTGCTTTAACAAATTCTATAG
TTGCAAGAAATGCTGTTGGTCATAAAAGCAAAAACCAAGAGGCGTTGTTAGAAGTTATTGATGACATAGTTGTATCAGG
AGGAGGTGTTAGTATAGTTGATATCTTTCCTTCCCTACAATGGCTTCCTACTGCCAAGAGGGAAAGATCAAGAATTTGG
AAATTGCACCAAAATACAGATGAGATTCTCGAAGATATCTTACAAGAGCATAGAGCTAAAAGACAGGCGACAGCTTCCA
AGAATTGGGATAGGAGCGAAGCTGATAATCTTCTTGATGTTCTTTTGGATCTTCAACAGAGCGGAAATCTTGATGTTCC
TTTAACTGATGTCGCCATCAAAGCAGCAATTATTGATATGTTTGGTGCTGGAAGCGACACATCCTCAAAAACTGCAGAA
TGGGCAATGGCTGAGTTGATGAGGAATCCAGAAGTAATGAAGAAAGCACAAGAAGAATTGCGGAATTTCTTTGGTGAAA
ATGGAAAGGTTGAGGAAGCAAAACTTCACGAATTAAAATGGATAAAGTTAATTATTAAAGAAACATTGAGATTACATCC
TGCAGTGGCTGTAATTCCAAGGGTTTGTAGGGAAAAGACTAAAGTTTATGGATATGACGTTGAGCCTGGCACTCGGGTT
TTCATTAACGTGTGGTCAATCGGAAGAGATCCTAAAGTTTGGAGTGAAGCTGAGAGATTCAAGCCGGAGAGATTTATTG
ATAGCGCAATTGATTACAGGGGTCTTAATTTTGAACTGATTCCATTTGGAGCAGGAAAAAGAATATGCCCTGGAATGAC
CTTAGGAATGGCTAATCTGGAGATTTTCCTTGCAAACTTGCTATATCATTTTGACTGGAAATTTCCTAAAGGAGTAACT
GCAGAAAATCTTGACATGAATGAAGCTTTTGGAGGAGCTGTCAAAAGAAAAGTAGACCTTGAATTGATCCCCATTCCAT
TCCGTCCCTAA

SEQ ID NO: 19

>CYP726A21
ATGGAACAACAAATCCTCTCTTTTCCAGTTCTTTTCAGTTTCCTTCTTTTTCTTCTGGTCCTATTAAAAGTATCTAAGA
AATTATCCAAACATGATTCCAACTCTCCTCCAGGACCATGGAAATTACCTTTCTTAGGTAATATTCTCCAGCTCGCTGG
TGATCTCCCTCACCGCCGAATAACGGAGTTGGCCAAAAAATACGGACCGGTAATGAGTATTAAACTTGGTCAGCATCCT
TATCTTGTTGTTTCTTCGCCGGAAACAGCCAAAGAAGTAATGAGAACCCAAGATCCCATTTTCGCTGATCGACCGCTTG
TCCTTGCGGGAGAATTAGTGCTTTACAACCGAAATGACATAGGTTTTGGGCTGTACGGAGATCAATGGAGACAAATGAG
AAAATTTTGCGCATTGGAATTACTTAGCACAAAACGAGTACAGTCGTTTCGATCCGTAAGAGAAGAAGAAATTGCAGAG
TTTGTAAAATCTCTGCGATCAAAAGAAGGAAGTTCTGTTAATCTGAGTCATACTTTATTTGCTTTAACAAACTCTATAA
TTGCAAGAAATACTGTCGGCCATAAAAGCAAAAATCAAGAAGCGTTGCTGAAAATTATTGATGATATAGTTGAGTCACT
GGGAGGTCTCAGTACAGTTGATATCTTTCCTTCCTTAAAATGGCTACCTTCAGTCAAAAGGGAAAGGTCAAGAATTTGG
AAATTGCATTGTGAAACAGATGAGATTCTTGAAGGTATCTTAGAAGAGCATAAAGCGAACAGGCAGGCCGCAGCTTTCA
AGAACGACGATGGGAGCCAAGCTGATAATCTTCTTGATGTTCTTTTGGATCTTCAGCAAAATGGAAATCTTGAAGTTCC
TTTAACTGACGTCAACATCAAAGCAGTAATCCTTGGTATGTTTGGCGCTGGAAGCGACACATCCTCCAAAACAACAGAA
TGGGCAATGGCGGAGTTGATGAAAAATCCGGAAATAATGAAAAAGGCACAAGAAGAATTGCGGAGTTTGTTTGGTGAAA
GTGGATACGTTGATGAAGCAAAACTTCACGAAATAAAATGGTTGAAGTTAATTATTAATGAAACATTGAGATTACATCC
TGCAGTTACATTAATTCCAAGGCTTTGCAGGGAAAAGACCAAAGTTAGTGGATATGACGTTTATCCTAATACTAGGGTT
TTCATAAATACATGGGCAATCGGAAGAGATCCTACAATTTGGAGTGAACCTGAGAAATTCGTTCCGGAGAGATTTATTG
ATAGTTCAATTGATTATAGGGGCAACCATTTTGAATATACTCCATTTGGTGCAGGAAGAAGAATATGCCCTGGAATGGC
ATTCGGTATGGTTAATCTAGAGATTTTCCTTGCAAATTTGCTATATCATTTTGACTGGAAACTTCCTAAAGGAATAACT
TCGGAGAATCTTGACATGACTGAGAATTTTGGAGGAGTTATCAAAAGAAAACAAGACCTTGAATTGATTCCCGCACCAT
TCCGTCCTTAA

Fig. 14

SEQ ID NO: 20

>CYP726A22
ATGGAACAGCAAATCCTCTCAGTTTCAGTTCTTTCCAGTTTCGTTCTTTTTCTTTTCGTCTTATTAAAAGTATCCAAGA
AATTATACAAACATGATTCTAACCCTCCGCCAGGACCATGGAAATTACCTTTCTTAGGTAATATCCTCCAGCTCGCCGG
CGACGCACCTCATCACCGGTTTGCGGAGTTGGCCAGAACTTATGGACCGGTAATGGGTATTAAACTCGGTGAAATTCCC
TTTCTTGTTGTTTCCTCGCCGGAAGCAGCCAAAGAAGTGATGAAAATACAAGATCCCATCTTTGCAGAACGAGCGCTTG
TCTTTGCAAATGATGTGTTGAACTATAACCGTAACGTTATGGTTTTTGGGTCATACGGATATCAATGGAGGCAATTGAG
AAAATTTTGTACGTTGGCATTACTGAGCGCAAAACGAGTACAGTCGTTTCAATCAGTAAGAAAAGAAGAAATGGCTGAT
TTTGTAAACTTTCTGCGTTCCAAAGAAGGAAGTTCTGTTAATCTTACTCATACTATATTTGCTTTTACAAATTCTATAA
TTGCAAGAAATGCTGTTGGTCATAAAACCAAAAATCAAGAAACGTTGTTAACATGTATTGATGGTATTATTTATACTGG
AGGAGTAAATATAGCTGACGTGTTTCCTTCCTTAAAATGGCTTCCTTCAGTCAAGAGGGAAAAATCTAGAGTTATGAAA
TTGCATTATGAAACAGATAAGATCCTGGAAGATATCTTACAAGAGCATAAAGCAAACAAGCAGGCGTGGGTTTCCGAGG
ATGGCGATGGGAGGAAAGCTGGCAATTTCGTTGATGTTCTTCTGGACCTTCAACAAAGTGGAAATCTTGATTTTCCCTT
AACTGATGTCACCATTAAAGCATCAACCATCGATGCTTTTGTGGGTGGAAGTGACACATCCTCAAAAACTACAGAATGG
GCAATGGCAGAGTTGATGAGGAAACCGGAAATAATGAAAAAAGCGCAAGAAGAATTGCGGAGTGTCTTTGGTGAAAAAG
GGTACATTGAGGAAGCAAAACTCCAGGAATTAAAATGGTTGAAGTTAATTATTAAAGAAACAATGAGATTACATCCTGT
ACTTTCACTACTTCCAAGGGTTTGTAAGCAAAAGACTAAAGTTAGTGGATATGATGTTTATCCTGGTACTCAAGTTCTG
GTTAATGTATGGGCACTCGGAAGAGATCCTAAACATTGGAGTGAACCTGAAAAATTCAATCCCGAGAGATTTATTGATA
GTTCAATCGATTATCTGGGAAATCATTTTGAATATCTTCCATTTGGTGCAGGAAAAAGAGTATGCCCTGGAATTGCATT
AGGTATGGTTCATATGGAAAATTTCCTCGCAAATTTGCTCTTTCATTTTGACTGGAAATTTCCTAAAGGAATTACTGCA
GAGAATCTTGACATGACCGATGCTTTTGGAGGAGTTATGAAGAGAAAAGTAGACCTTGAACTGATTCCCATTCCATACC
ATCCTTAA

SEQ ID NO: 21

>CYP726A23
ATGGAACATCAAATCCTCTCATTTCCAGCTCTTTTCAGTTTCCTTCTTTTTCTTCTGGTCTTATTAAAAGTATCCAAGA
AATTATACAAACATGATTCTAACCCTCCACCCGGACCATGGAAATTACCTTTCTTAGGTAACATTCTCCAGCTTGCCGG
CGACACATTTCATAGACGGTTAACAGAGTTGGCTAAAACTCATGGCCCGGTAATGAGTATTAATGTCGGTCAGATTCCT
TATGTTGTCGTTTCTTCCCCGGAAACAGCCAAAGAAGTAATGAAAATTCAAGATCCAGTTTTCGCCGACCATCCGGTTG
TCCTTGCAGCAGAAGTAATTCTTTATAGCCCATACGACATCTTTTTTGCGCCCTACGGAGATCACTTGAAACAAATGAG
AAAATTTTGCACGGTCGAATTACTTAGCACAAAACGAGTACAGTCGTTTCGATCTGTGAGAGAAGAAGAAGTTGCAGAT
TTTGTAAAATTTCTGCGTTCAAAAGAGGGAAGTTCTGTTAATCTTACTCATACTTTATTTGCTTTGACAAATTCTATAG
TTGCAAGAACTGCTGTTGGTCATAGAAGCAAAAATCAAGAAGGATTGTTAAAAGTTATTGATGAAGCAGTTTTAGCTTC
ATCAGGTGTTAATATAGCTGATATCTTTCCTTCCTTACAATGGCTTCCTTCAGTCAAAAGGGAAAGGTCTAGAATTTGG
AAAACGCATCGTGAAACAGATAAGATTCTCGAAGATGTTTTGCAAGAGCATAGAGCTAACAGGAAGGCGGCAGTTCCCA
AGAATGGAGATCAGAGCCAAGCTGATAATCTTCTTGATGTTCTTTTGGATCTTCAAGAAAGTGGAAATCTTGATGTTCC
CTTACCTGATGCCGCCATCAAAGGAACAATCATGGAAATGTTTGGGGCTGGCAGCGACACGTCCTCAAAAACAGTAGAA
TGGGCAATGGCAGAGTTGATGAGGAATCCAGAAGTAATGAGAAAAGCACAAGAAGAATTGCGGAGTTTCTTTGGTGAAA
ATGGAGAGGTTGAGGATGCAAAAATTCAGGAATTAAAATGTTTAAAGTTAATTATTAAAGAAACATTGAGATTACATCC
TCCAGGTGCAGTAATTCCAAGGCTTTGTAGGGAAAGAACTAAAGTCGCTGGATACGACATTTATCCTAATACTAAGATT
TTCGTTAATACATGGGCAATTGGAAGAGATCCTGAAATTTGGAGTGAAGCTGAGAAATTCAATCCCGACAGATTTATTG
ACAGTTCAATTGATTATAAGGGTAACAATTTTGAACTGATTCCATTTGGTGCAGGAAGAAGAATATGCCCCGGAATTAC
ATTAGCTTCAGCTAATATGGAACTTTTCCTTGCAAACTTGCTATATCATTTTGACTGGAAATTTCCTCAAGGAATAACA
GCAGAGAATCTCGACATGAATGAATGTTTTGGAGGAGCTGTCAAAAGAAAAGTAGACCTTGAACTCATTCCTATTCCAT
TCCGTACTTAA

SEQ ID NO: 22

>CYP726A24
ATGCTCTCATTTCCAGTTATTTTCAGTTTCCTTCTTTTCCTTCTCGTCTTATTAAAAGTATCCAAAAAATTATGCAAAG
ATAATTCTATCCCTCCGCCGGGACCATGGCAATTACCTTTCTTGGGTAACATTTTCCAGCTCGCAGGCTACCAATTTCA
TATCCGGTTAAGCGAGTTGGGCCAAACTTATGGACCAGTAATGGGTATTAAAGTCGGTCAAGTTCCTTTTCTTATCGTT
TCTTCGCCGGAAATGGCCAAAGAAGTGTTGAAAGTCCAAGATCCCACTTTCGTCGACCGACCGGTTGTCCTTGCAGCAG
AATTGGTGATGTATGGGGGCCACGACATCGTTTATGCGCCATACGGAGATCAATGGAGACAAATGAGAAAATTTTGCAC
GTTAGAGTTACTTAGCACAAAACGAGTGCAATCCTTTCGATCCGTAAGAGAAGAAGAAGCTGGAGAGTTTGTAAAATTT
CTACTTTCAAAAGAGGGAAGTTCTGTTAACCTTACTCATGCTTTATATGCTTTATCAAATTCTATGGTTGCAAGAAGTA
CTGTTGGTCATAAAACCAAAAATCAAGAAGCGTTATTAAACGTTATTGATGATACAGTTTCAACAGCGGCAGGTACTAA
TATAGCCGATATCTTTCCGTCCTTAAAATGGCTTCCTACAGTCAAACGGCAGATGTCTAGAATTTGGAAATCTCATTGT
CAAACAGATGAGATTCTTGAAGGTATCTTAAGAGAGCATAGAGCTAAAAGGCAGACGGCAGCTTCCAAGAACGGTGATC
GGGCTGAAGCCGATAATCTTCTTGATGTTCTTTTGGATCTTCAACAGAGAGGAGATCTTGATGTTCCCTTAACTGATAT
CAACATCAAAGGAGCAATCCTGGAAATGTTTGGCGCTGGAAGCGACACATCTACAAAAACTTTAGAATGGGCAATGTCA
GAATTGATGAGGAACCCAAAAATGATGAAAAAAGTACAACAAGAATTGCGGAGTTTCTTTGGTGAAAATGGAAAAGTTG
AGGAAGCAAAACTTCAGGAATTAAAATGGTTAAAGTTAATTATTAAAGAAACATTGAGATTACATCCTCCAATTGCAGT
AATTCCAAGGCTTTGTAGGGAGAGGACTAAAGTTTGTGGATATGACGTTTATCCTAATACCAGGGTTTTCGTTAATGTC
TGGGCAATGGGAAGAGATCCTAAAATTTGGAATGAAGCTGAAAAATTCAATCCTGAGAGATTTATTGATAGTTCAATTG
ATTATAGGGGTAATAATTTTGAACTGATTCCATTTGGTGCAGGAAAAAGAATATGCCCTGGAATTACATTAGCTATTGT
TCATGTAGAAACTGTCCTTGCAAACTTGCTATATCACTTTGACTGGAAATTTCCTGAAGGAGTAACTGCAGAGAATTTT
GATATGAATGAAACTTTTGCAGGAATTATCCGAAGAAAAGTAGACCTTGAACTGATCCCTGTTGCATTCCGTCCTTAA

Fig. 15

SEQ ID NO: 23

>CYP726A25
ATGGACCACCGAATTCTCTCATTCCCATTCCTAATGCTAAGCTTGCTTCTTCCTTTCGTTTTCGAGTTGTTAAAGATAT
GGAAGAAGAGTAATAATAATCCTCCTCCAGGACCTTGGAGATTACCTCTGATCGGTAACATTCACCAGTTGGGTGGGCG
TCATCAACCCCATCTCCGCCTTACAGACTTGGCCAGAACTTATGGACCCGTTATGCGCCTGCAGCTTGGCCAAATTGAA
GCAGTAGTCATTTCCTCAGCTGAAACAGCCAAACAAGTTATGAAAACCCAAGAAAGCCAATTCCTTGGAAGACCTTCTC
TTTTAGCTGCCGATATCATGCTTTATAACCGTACAGACATCTCTTTCGCCCCTTATGGAGATTACTGGAGACAAATGAA
AAAAATTGCTGTCGTTGAGCTCCTTAGCGCCAAGCGTGTCCAAGCCTACAAATCAGTCATGGATGAGGAAGTTTCCAAT
TTCATCAATTTTCTTTATTCAAAAGCGGGGTCGCCTGTGAATCTTACTAAGACATTCTATTCCTTAGGAAATGGAATCA
TCGCAAAAACATCCATCGGCAAAAAATTTAAGAAACAAGAAACCTTCTTAAAAGTCGTAGACAAAGCCATTAGAGTAGC
AGGAGGTTTCAGTGTGGGGGATGCGTTTCCTTCCTTTAAATTGATTCACTTGATCACTGGAATCAGCTCCACACTCCAT
ACAGCTCATCAAGAGGCAGACGAGATTCTTGAAGAAATTATAAGCGAACACAGAGCCAGTAAGACTGCTGATGGTGATG
ACTATGAAGCCGATAATATTCTTGGCGTTCTTTTGGATATTCAAGAACGTGGGAACCTTCAAGTCCCCTTGACCACGGA
CAATATCAAAGCTATCATTCTGGACATGTTTGCCGGTGCAAGTGACACATCGTTAACAACTGCAGAATGGGCAATGGCA
GAAATGGTAAAGCATCCAAGAATAATGAAGAAAGCACAAGACGAAGTTAGGCGGACTTTGAACCAAGAAGGAAACGTAG
CTAATCTTCTTCCTGAACTGAAATATTTGAAATTAGTTATCAAAGAAACCTTGAGATTACATCCTCCAGTAGCCTTAAT
TCCTAGAGAATGTGATGGGCGATGTGAGCTTAATGGGTACGATGTTAATCCTAAAACTAAGATTCTTGTTAACGCATGG
GCAATCGGAAGAGATCATAATTTATGGAATGATCCTGAAAGATTTGATCCGGAGAGATTTCTTGACAATTCAAGTGATT
TCAGGGGAACCGACTTCAAATTCATTCCATTTGGCGCCGGAAAGAGGATTTGTCCTGGCATAACCATGGCTATAACTAT
TATTGAGGTCCTGCTTGCACAATTGCTCTACCATTTTGATTGGAAACTTCCTGATGGAGCTAAACCAGAAAGTCTTGAC
ATGTCTGATACATTTGGTCTCGTAGTTAAGAGAAGGATAGATCTCAATTTGATTCCAATCCCATAG

SEQ ID NO: 24

>CYP726A26
ATGGAGTATCAAATCCTCTCATCTCCAACCCTTATAGCCTTGTTGGTTTTTGTGGCGACAGTGGTGATAAAATTATGGA
AGAGACCCACAATAGCTAACAACAATCCTCCACCAGGACCTTGGAAGTTGCCTCTGATAGGCAACCTTCATAATTTGTT
TGGCCGTGATCAGCCACACCACCGCCTCCGAGATTTGGCCGGAAAGTATGGAGCCGTAATGGGTTTTCAGCTTGGACAG
GTTCCCACTGTTGTAATATCCTCGGCAGAAATAGCCAAACAAGTCTTAAAAACCCATGAGTTCCAATTCATCGACAGAC
CCTCTCTCTTGGCTGCCGATATCGTGCTTTATAATCGTTCTGACATTATATTTGCCCCTTACGGAGACTACTGGAGACA
AATCAAGAAAATTGCCATACTCGAGCTGCTTAGTTCAAAGCGCGTGCAGTCATTCAAATCAGTGAGAGAAGAGGAGGTC
TCCAGTTTCTTCAAGTTCTTATATTCAAAAGCTGGATCGCCTGTCAATCTTAGTCGGACTCTCTTGTCTTTAACTAATG
GGATCATAGCCAAAACTTCCATAGGTAAGAAATGCAAAAGACAGGAAGAAATCATTGCAGTTATAACGGATGCCATTAA
AGCAACAGGAGGTTTCAGCGTCGCCGATGTTTTTCCCTCCTTTAAATTTCTTCACATTATTACCGGCATCAGCTCTACT
ATCCGCAGGATTCATCGAGAGGCAGATACGATTCTTGAAGAAATTATGGACGAACACAAAGCCAACAACGAATCAAAGA
ATGAACCCGATAACATTCTGGATGTTCTTTTGGATATTCAACAGCGAGGAAACCTTGAATTCCCCCTCACCGCTGACAA
CATCAAAGCTATCATTCTGGAAATGTTTGGAGCTGCGAGTGACACATCTTCCGTGACCATTGAATGGGCAATGTCTGAA
ATGATGAAGAACCCATGGACGATGAAAAAAGCTCAAGAAGAAGTAAGGGAGGTATTTAATGGAACAGGTGACGTCAGCG
AAGCAAGCCTTCAAGAATTACAATATTTGAAGTTAGTTATCAAAGAAACTCTAAGATTGCATCCTCCGCTCACCTTAAT
CCCTAGAGAATGCAATCAGAAATGTCAGATTAATGAATATGATATTTATCCAAAAACCAGAGTCCTTGTCAATGCATGG
GCCATCGGAAGAGATCCTAACTGGTGGACTGATCCTGAAAGATTTGATCCAGAGAGATTTCGTTGCGGTTCAGTTGATT
TCAAAGGCACTGACTTTGAGTTCATCCCTTTTGGTGCTGGTAAAAGAATGTGTCCCGGCATAACCATGGCTATGGCTAA
CATTGAACTTATACTTGCACAACTACTGTACCATTTTAACTGGGAACTTCCTGGAAAAGCTAAACCAGAAACTCTCGAC
ATGTCTGAGAGTTTCGGTCTTGCAGTTAAAAGAAAGTCGAGCTTAACTTGATTCCGACCGCGTTTAATCCTTAG

Fig. 16

SEQ ID NO: 25

>Jcu17062
ATGGAACAACAAATCCTCTCTTTTCCAGTTATTTTCAATTTCCTTCTTTTTCTTCTGGTCCTATTAAAAG
TATCTAAGAAATTATCCAAACATGATTCGAACTCTCCTCCAGGACCATGGAAATTACCTTTCTTAGGTAA
TTTTCTCCAGCTCGCTGGTGATCTCCCTCACCGCCGAATAACGGAGTTGGCCAAAAAATACGGACCGGTA
ATGAGTATTAAACTTGGTCAGCATCCTTATCTTGTTGTTTCTTCGCCGGAAACAGCCAAAGAAGTAATGA
GAACCCAAGATCCCATTTTCGCTGATCGACCGCTTGTCCTTGCTGGAGAATTAGTGCTTTACAACCGAAA
TGACATAGGTTTTGGGCTGTACGGAGATCAATGGAGACAAATGAGAAAATTTTGCGCATTGGAATTACTT
AGCACAAAACGAATACAGTCGTTTCGATCCGTAAGGGAAGAAGAAATTGCAGTGTTTGTAAAATCTCTGC
GATCAAAAGAAGGAAGTTCTGTTAATCTGAGTCATACTTTATTTGCTTTAACAAACTCTATAATTGCAAG
AAATACTGTCGGCCATAAAAGCAAAAATCAAGAAGCGTTGCTGAAAATTATTGATGATATAGTTGAGTCA
CTAGGAGGTCTCAGCACAGTTGATATCTTTCCTTCCTTAAAATGGCTACCTTCAGTCAAAAGGGAAAGGT
CAAGAATTTGGAAATTGCATTGTGAAACAGATGAGATTCTTGAAGGTATCTTAGAAGAGCATAAAGCGAA
CAGGCAGGCCGCAGCTTTCAAGAACGACGATGGGAGCCAAGCTGATAATCTTCTTGATGTTCTTTTGGAT
CTTCAACAAAATGGAAATCTTCAAGTTCCTTTAACTGACGTCAACATCAAAGCAGTAATCCTTGGTATGT
TTGGCGCTGGAAGCGACACATCCTCCAAAACTACAGAATGGGCAATGGCGGAGTTGATGAAAAATCCGGA
AATAATGAAAAACGCACAAGAAGAATTGCGGAGTTTGTTTGGTGAAAGTGGAAACGTTGATGAAGCAAAA
CTTCACGAAATAAAATGGTTGAAGTTAATTATTAATGAAACATTGAGATTACATCCTGCAGTTACATTAA
TTCCAAGGCTTTGCAGGGAAAAGACTAAAATTAGTGGATATGACGTCTATCCTAATACTAGGGTTTTCAT
AAATACATGGGCAATCGGAAGAGATCCTATAATTTGGACTGAACCTGAGAAATTCGTTCCGGAAAGATTT
ATTGATAGTTCAATTGATTACAGGGGCAACCATTTTGAATATACTCCATTTGGTGCAGGAAGAAGAATAT
GCCCTGGAATGACATTTGGTATGGTTAATCTAGAGATTTTCCTTGCAAATTTGCTATATCATTTTGACTG
GAAACTTCCTAAAGGAATAACTTCGGAGAACCTTGACATGACTGAGAATTTTGGAGGAGTTATCAAAAGA
AAACAAGACCTTGAATTGATTCCCGTACCATTCCGTCCTTAA

SEQ ID NO: 26

>Jcu17064
ATGGAAGACCAAATCCTCTCATTTCAAGTTCTTTTCAGTTTCCTTCTTTTTCTTTTCGTCTTATTCAAAG
TATCCAAGAAATTGTACAAACATGGTTCTAACCCTCCGCCCGGACCACTGAAATTACCTTTCTTAGGTAA
TATTCTCCAGCTCGCCGGAGATGTACCTCACCGCCGGTTAACAGCCTTGGCCAAAACTTACGGACCCGTA
ATGGGTATTAAACTCGGTCAGATTCCTTTCCTTGTCGTGTCCTCCCCGGAAACAGCTAAAGAAGTAATGA
AAATACAAGATCCCGTTTTCGCAGAACGAGCGCCTCTCCTTGCAGGAGAAATAGTGCTTTATAACCGAAA
CGACATCATTTTTGGATTGTACGGAGATCAGTGGAGGCAAATGAGAAAAATTTGCACGTTGGAATTACTT
AGCGCGAAACGAGTACAGTCCTTTCGATCAGTGAGAGAAGAAGAAGTCGCAGATTTAGTCAAATTTCTTG
GTTCGAAAGAGGGAAGTCCTGTTAATCTTACTCATACTTTATTCGCTTTAGCAAATTCTATAATTGCAAG
AAATACGGTTGGTCAGAAAAGCAAAAACCAAGAAGCATTGCTAAGACTTATTGATGATATAATTGAATTA
ACAGGAAGTGTTAGTATAGCTGATATATTTCCTTCCTTAAAATGGCTTCCTTCAGTCCAAAGGGATAGGT
CTAGAATTAGGAAATTGCATTATGAAACAGATGAGATCCTTGAAGATATTTTACAAGAGCATAGAGCTAA
CAGGCAGGCTGCGGCTTCCAGGAAAGGCGATCGGAGGGGAGCTGATAATCTTCTTGATGTTCTTTTGTAT
CTTCAAGAAACTGGAAATCTTGATGTTCCTTTAACTGATGTCGCTATCAAAGCAGCAATCATTGATATGT
TTGGAGCTGGAAGCGACACATCCTCAAAAACCGTAGAATGGGCAATGGCTGAGTTGATGAGGAATCCAGA
AATAATGAAGAAAGCACAAGAAGAATTGCGGAATTTCTTTGGTGAAAATGGAAAGGTTGACGAAGCAAAA
CTTCAAGAATTAAAATGGTTAAATTTAATTAATAAAGAAACATTGAGATTACATCCTGCAGCAGCTGTAG
TTCCAAGGGTTTGTAGGGAAAGGACTAAGGTGAGTGGATATGACGTTTATCCTGGCACTCGGGTTTTCAT
TAACGCATGGGCAATCGGAAGAGATCCTAAAGTTTGGAGTGAAGCTGAGAAATTCAAACCGGAGAGATTT
ATTGATAGTGCAATTGATTATAGGGGTACCAATTTTGAACTAATTCCATTTGGAGCAGGAAAAAGAATAT
GCCCTGGAATGACTCTAGGTATGGCTAATCTGGAGATTTTCCTGGCAAACTTGCTATATCATTTTGACTG
GAAATTTCCTAAAGGAGTAACTGCAGAAAATCTTGACATGAACGAAGCTTTTGGAGCAGCTGTCAAAAGA
AAAGTAGACCTTGAATTGGTTCCCATTCCATTCCGTCCTTAA

Fig. 17

SEQ ID NO: 27

>CYP726A18
MSSQPAVLQSNFLNRNVQPFLTIPSASTKYSGTACFSSFPSVKLNARPPQACFSLNKNND
HSTPTSILPPGPWQLPLIGNIHQLVGHLPHSRLRDLGKIYGPVMSVQLGEVSAVVVSSVE
AAKEVLRIQDVIFAERPPVLMAEIVLYNRHDIVFGSYGDHWRQLRKICTLELLSLKRVQS
FKSVREDEFSNFIKYLSSKAGTPVNLTHDLFSLTNSVMLRTSIGKKCKNQEAILRIIDSV
VAAGGGFSVADVFPSFKLLHMISGDRSSLEALRRDTDEILDEIINEHKAGRKAGDDHDEA
ENLLDVLLDLQENGDLEVPLTNDSIKATILDMFGAGSDTSSKTAEWALSELMRHPEIMKK
AQEEVRGVFGDSGEVDETRLHELKYLKLVIKETLRLHPAIPLIPRECRERTKINGYDVYP
KTKVLVNIWAISRDPNIWSEADKFKPERFLNSSLDYKGNYLEFAPFGSGKRVCPGMTLGI
TNLELILAKLLYHFDWKLPDGITPETLDMTESVGGAIKRRTDLNLIPVLYPTH

SEQ ID NO: 28

>CYP726A14
MEQQLLSFPALLSFLLLIFVVLRIWKQYTYKGKSTPPPGPWRLPLLGNFHQLVGALPHHR
LTELAKIYGPVMGIQLGQISVVIISSVETAKEVLKTQGEQFADRTLVLAAKMVLYNRNDI
VFGLYGDHWRQLRKLCTLELLSAKRVQSFKSVREEELSNFVKFLHSKAGMPVNLTHTLFA
LTNNIMARTSVGKKCKNQEALLSIIDGIIDASGGFTIADVFPSVPFLHNISNMKSRLEKL
HQQADDILEDIINEHRATRNRDDLEEAENLLDVLLDLQENGNLEVPLTNDSIKGAILDMF
GAGSDTSSKTAEWALSELMRHPEEMKKAQEEVRRIFGEDGRIDEARFQELKFLNLVIKET
LRLHPPVALIPRECREKTKVNGYDIYPKTRTLINVWSMGRDPSVWTEAEKFYPERFLDGT
IDYRGTNFELIPFGAGKRICPGMTLGIVNLELFLAHLLYHFDWKLVDGVAPDTLDMSEGF
GGALKRKMDLNLVPIPFTTLP

SEQ ID NO: 29

>CYP726A17
MEKQILSFPVLLSFVLFILMILRIWKKSNPPPGPWKLPLLGNIHQLAGGALPHHRLRDLA
KTYGPVMSIQLGQISAVVISSVQGAKEVLKTQGEVFAERPLIIAAKIVLYNRKDIVFGSY
GDHWRQMRKICTLELLSAKRVQSFRSVREEEVSEFVRFLQSKAGTPVNLTKTLFALTNSI
MARTSIGKKCEKQETFSSVIDGVTEVSGGFTVADVFPSLGFLHVITGMKSRLERLHRVAD
QIFEDIIAEHKATRALSKNDDPKEAANLLDVLLDLQEHGNLQVPLTNDSIKAAILEMFGA
GSDTSSKTTEWAMSELMRNPTEMRKAQEEVRRVFGETGKVDETRLHELKFLKLVVKETXR
LHPAIALIPRECRERTKVDGYDIKPTARVLVNVWAIGRDPNVWSEPERFHPERFVNSSVD
FKGTDFELLPFGAGKRICPGILVGITNLELVLAHLLYHFDWKFVDGVTSDSFDMREGFGG
ALHRKSDLILIPIPFTP

SEQ ID NO: 30, *Euphorbia peplus*

>CYP726A19
MATLQHSMQANLQKQNLHPLLNKSFGTPNRPSFVYSSKSASRRTIQACLSSNSQPGGVCP
MANRFASSTTNQSVTESSSKPDEEDENSPVKLPPGPWKLPLLGNILQLVGDLPHSRLRDL
ATEYGPVMSVQLGEVYAVVISSVEAAREILRNQDVNFADRPPVLVSEIVLYNRQDIVFGA
YGVHWRQMRRLCTTELLSIKRVQSFKLVREEEVSNFIKSLYSKAGKPVNLTEGLFTLTNS
IMLRTSIGKKCRDQDTLLRVIEGVVAAGGGFSIADVFPSAVFLHDINGDKSGLQSLRRDA
DLILDEIIGEHRAIRGTGGDQGEADNLLDVLLDLQENGNLEVPLNDDSIKGAILDMFGAG
SDTSSKSTEWALSELLRHPEEMKKAQDEVRRVFAKKGNVEESQLDQLKYLKLVIKETLRL
HPAVPLIPRECREKTKVNGYDILPKTKALVNIWAISRDPKIWPEADKFIPERFENSSIDF
KGNNLEFAPFGSGKRICPGMALGITNLELFLAQLLYHFDWKLADGKDGRDLDMGEVVGGA
IKRKVDLNLIPIPFHTSPAN

SEQ ID NO 31, *Euphorbia fischeriana*

>Efi003329
MSTLQPFLQANFQKQNSHPLLSKPLGTTNHPSFISSSKSTKRSTIQACLSSNSQPGGVCP
MANRFASSSTTNQSVTQSSSNPDEKDGNSQVQLPPGPWKLPFIGNILQLVGDLPHRRLRD
LATVYGPVMSVQLGEVYAVIISSVEAAKEVLRTQDVNFADRPPVLVSEIVLYNRQDIVFG
SYGDHWRQMRRICTMELLSIKRVQSFKSVREEEVSNFIKLLYSEAGQPVNLTEKLFALTN
SIMLRTSIGKKCKDQETLLRVIEGVVAAGGGFSVADVFPSAVFLHDITGDKSGLESLRRD
ADLVLDEIIGEHRANRSGNGGDEGEAENLLDVLLDLQENGNLEVPLNDDSIKATILDMFG
AGSDTSSKSTEWALSELLRHPVAMKKAQDEVRKVFSENGNVEEEGLNQLKYLKLVIKETL
RLHPAIPLIPRECREKTKVNGYDILPKTKALVNIWAISRDPTIWPEADKFIPERFENSSM
DFKGNHCEFAPFGSGKRICPGMALGITNLELFLAQLLYHFDWKLTDGKDPRNLDMSEVVG
GAIKRKIDLNLIPIPFHP

Fig. 18

SEQ ID NO 32, *Jatropha curcas*

>Jcu2819
MSLQPAILQGNTCKQYFHPLSSISSTRWVGNCNRFAFLSPAKPTANRAPQASLSSKLQPV
VRLLTKFPASGFLAMNQSVDQFASTTTSLTKIFNKIGKPIQSSPFLVSVLLLMFMASKIQ
NQQEEDDNSINLPPGPWRLPFIGNIHQLAGPGLPHHRLTDLAKTYGPVMGVHLGEVYAVV
VSSAETSKEVLRTQDTNFAERPLVNAAKMVLYNRNDIVFGSFGDQWRQMRKICTLELLSV
KRVQSFKSVREEEMSSFIKFLSSKSGSPVNLTHHLFVLTNYIIARTSIGKKCKNQEALLR
IIDDVVEAGAGFSVTDVFPSFEALHVISGDKHKFDKLHRETDKILEDIISEHKADRAVSS
KKSDGEVENLLDVLLDLQENGNLQFPLTNDAIKGAILDTFGAGSDTSSKTAEWTLSELIR
NPEAMRKAQAEIRRVFDETGYVDEDKFEELKYLKLVVKETLRLHPAVPLIPRECRGKTKI
NGYDIFPKTKVLVNVWAISRDPAIWPEPEKFNPERFIDNPIDYKSINCELTPFGAGKRIC
PGMTLGITNLELFLANLLYHFDWKLPDGKMPEDLDMSESFGGAIKRKTDLKLIPVLARPL
TPRNANSGNTFTTTDADSPASMCPHLKAL

SEQ ID NO 33, *Jatropha gossypifolia*

>Jgo02184
MSLQPAVLQANTCKQYFHPLSSISSTRWVGNCNRFAFLSPAKPTANRAPQASLSSKLQPV
VRLLTRFPASGFLAMNQSVNQFASTTTSLAKIFDKIGKPIQSSPFLLSVLLLMFMASKIQ
NQQEEDNNSINLPPGPWRLPFIGNIHQLAGPGLPHHRLTDLAKTYGPVMGVHLGEVYAVV
VSSAETSKEVLRTQDTNFAERPLVNAAKMVLYNRNDIVFGSYGDQWRQMRKICTLELLSL
KRVQSFKSVREEEMSSFIKFLCSKSGSPVNLTHHLFVLTNYIIARTSIGKKCKNQEALLR
VIDDVVEAGAGFSVTDVFPSFEALHVISGDKHKFDKLHRETDKILEDIISEHKADRAVSS
KKSDGEAENLLDVLLDLQENGNLQFPLTNDAIKGAILDTFGAGSDTSSKTAEWTLSELIR
NPGAMRKAQEEIRRVFDETGYVDEDKFEELKYLKLVVKETLRLHPAVPLIPRECRGKTKI
NGYDIFPKTKVLVNVWAISRDPAIWPEPEKFNPERFIDNPIDYKSINCELTPFGAGKRVC
PGMTLGITNLELFLANLLYHFDWKLPDGKMPEDLDMSESFGGAIKRKTDLKLIPVLARPF
NPTNANNGNTFTTTDANSPSSMCPHLKAL

SEQ ID NO: 34

>CYP726A4
MELQFQIPSYPVLFSFFIFIFILIKIVKKQTQNSISPPGPWKYPILGNIPQLAAGGKLPH
HRLRDLAKIHGPVMNIQLGQVKSIVISSPETAKEVLKTQDIQFANRPLLLAGEMVLYNRK
DILYGLYGDQWRQMRKICTLELLSAKRIQSFKSVREQEVESFIRLLRSKAGSPVNLTTAV
FELTNTIMMITTIGEKCKNQEAVMSVIDRVSEAAAGFSVADVFPSLKFLHYLSGEKGKLQ
KLHKETDEILEEIISEHKANAKIGSQADNLLDVLLDLQKNGNLQVPLTNDNIKAATLEMF
GAGSDTSSKTTDWAMAQLMRKPSAMKKAQEEVRRVFSDTGKVEESRIQELKYLKLIVKET
LRLHPAVALIPRECREKTKIEGFDVYPKTKILVNPWAIGRDPKVWSDPESFNPERFEDSS
IDYKGTNFELIPFGAGKRICPGMTLGIVNLELFLANLLYHFDWKFPNGVTAENLDMTEAI
GGAIKRKLDLELIPIPYTLS

SEQ ID NO: 35

>CYP726A15
MSLQPAPVSQSNFLYKKVPPILRAPTTKSSGSSRSSFFSSSVKLAARPPQPQACLSLNKN
DDSNTSASSLPPGPWKLPLLGNIHQLVGALPHHRLRDLAKAYGPVMSVKLGEVSAVVISS
VDAAKEVLRTQDVNFADRPLVLAAEIVLYNRQDIVFGSYGEQWRQMRKICTLELLSIKRV
QSFKSVREEELSNFIRYLHSKAGTPVNLTHHLFSLTNSIMFRISIGKKYKNQDALLRVID
GVIEAGGGFSTADVFPSFKFLHHISGEKSSLEDLHREADYILEDIINERRASKINGDDRN
QADNLLDVLLDLQENGNLEIALTNDSIKAAILEMFGAGSDTSSKTAEWALSELMRHPEEM
EKAQTEVRQVFGKDGNLDETRLHELKFLKLVIKETLRLHPPVALIPRECRQRTKVNGYDI
DPKTKVLVNVWAISRDPNIWTEAEKFYPERFLHSSIDYKGNHCEFAPFGSGKRICPGMNL
GLTNLELFLAQLLYHFNWEFPDGITPKTLDMTESVGAAIKRKIDLKLIPVLFHP

SEQ ID NO: 36

>CYP726A16
MESAAHQSYFHMFLAMEQQILSFPVLLSFLLFIFMVLKVWKKNKDNPNSPPGPRKLPIIG
NMHQLAGSDLPHHPVTELSKTYGPIMSIQLGQISAIVISSVEGAKEVLKTQGELFAERPL
LLAAEAVLYNRMDIIFGAYGDHWRQLRKLCTLEVLSAKRIQSFSSLRQEELSHFVRFVHS
KAGSPINLSKVLFALTNSIIARIATGKKCKNQDALLDLIEDVIEVSGGFSIADLFPSLKF
IHVITGMKSRLEKLHRITDQVLEDIVNEHKATRAASKNGGGDDDKKEAKNLLDVLLDLQE
DGSLLQVPLTDDSIKAAILEMLGGGSDTSAKTTEWAMSEMMRYPETMKKAQEEVRQAFGN
AGKIDEARIHELKYLRAVFKETLRLHPPLAMIPRECRQKTKINGYDIYPKTKTLINVYAI
GRDPNVWSEPEKFYPERHLDSPIDFRGSNFELIPFGAGKRICPGMTLAITTVELFLAHLL
YYFDWKFVDGMTADTLDMTESFGASIKRKIDLALVPIPVSPLP

Fig. 19

SEQ ID NO: 37, *Ricinus communis*

>CYP726A13
MDKQILSYPVLLLSFLLFILMVLRIWKKSKGSFNSPPGPWKLPLIGNMHQLITPLPHHRL
RELAKTHGPVMSIQLGQVSAVVISSVEAAKQVLKTQGELFAERPSILASKIVLYNGMDII
FGSYGDHWRQMRKICTFELLSPKRVQSFSSVRQEELSNYVRFLHSNAGSPVNLSKTLFAL
TNSVIAKIAVGKECKNQEALLNLIEEVLVAAGGFTVADSFPSYNFLHVITGMKSNLERLH
RITDKILEDIITEHKAPRALFKRGGDEDKKEAENLLDVLLGLQEHGNLKVPLTNESVKSA
ILEMLSGGSDTSAKTIEWAMSELMRSPEAMEKAQEEVRRVFGELGKIEESRLHELKYLKL
VIKETLRLHPALALIPRECMKRTKIDGYDISPKTKALVNVWAIGRDPSVWNEPEKFFPER
FVDSSIDFRGNNFELLPFGSGKRICPGMTLGLATVELFLSYLLYYFDWKLVGGVPLDMTE
AFAASLKRKIDLVLIPISVGPSPTTD

SEQ ID NO 38

>CYP726A10
MELQIFSFPVLLSFFLFIFMVLRIWKNSNKKLNPPPGPWKLPLLGNIHQLATPLPHQRLR
DLAKSFGPVMSIKLGEISAVIISSAEAAQEVLKSQDVTFAERPASLASKLVLYNRNDIVF
GAYGPQWRQTRKLCVLELLSAKRIQSFKSVREEEVDEFAKFVYSKGGTPVNLTDKLFALT
NTIMARTTIGKKCRSEKDLLRCIDGIFEEAGVFNLADAFPSFTLLPVITGAKFRLEKLHR
ETDKILEDILREHIASKAASDKDTRNLLHVLLDLQESGNLEVPITNDSIKATILDIFIAG
SDTSAKTVEWAMSELMRNPKLMKRAQEEVRQVFGEKGFVDEAGLQDLKFMKLIVKETLRL
HPVFAMFPRECREKTKVNGYDISPKTTMLINVWAIGRDPNVWPDAEKFNPERFLDSSIDY
KGNNAEMIPFGAGKRICLGMTLGTLILEHFLAKLLYHFDWKFPDGVTPENFDMTEHYSAS
MRRETDLILIPIPVHPLPTH

SEQ ID NO 39

>CYP726A11
MEQQILSFSVLSCLILFLLMVINILKNYSKDFTPPPGPWKLPFLGNIHQLATALPHRRLR
DLAKTYGPVMSIKLGEISSIVISSAEAAQEVLKTQDVIFAERPIALAAKMVLYNRDGIVF
GSYGEQLRQSRKICILELLSAKRIQSFKSVREEEVSNFISFLNSKAGTPVNLTDKLFALT
NSIMARTSIGKKCKNQEDLLRCIDNIFEEATVFSPADAFPSFTLLHVITGVKSRLERLHQ
QTDKILEDIVSEHKATMAATENGDRNLLHVLLDLQKNGNLQVPLTNNIIKAIILTIFIGG
SDTSAKTVEWVMSELMHNPELMKKAQEEVRQVFGEKGFVDETGLHELKFLKSVVKETLRL
HPVFPLVPRECREVTKVNGYDIYPKTKVLINVWAIGRDPDIWSDAEKFNPERFLESSIDY
KDTSSEMIPFGAGKRVCPGMSLGLLILELFLAQLLYHFDWKLPDRVTPENFDMSEYYSSS
LRRKHDLILIPIPVLPLPIE

SEQ ID NO 40

>CYP726A12
MEQQILSFPVLLSFFLFIFMVLKIRKKYNKNISPPPGPWKLPILGNIHQLISPLPHHRLR
DLAKIYGPVMSIKLGEVSAVVISSAEAAKEVLRTQDVSFADRPLGLSAKMVLYNGNDVVF
GSYGEQWRQLRKICILELLSAKRVQSFKSLREAEVSNFIRFLYSKAGKPVNLTRKLFALT
NTIMARTSVGKQCENQEVLLTVIDRIFEVSGGFTVADVFPSFTLLHLITGIKSRLERLHQ
DTDQILEDIINEHRACKAVSKNGDQNEADNLLDVLLDLQEDGNLRVPLTNDSIKGTILDM
FAGGSDTTSKTAEWAVSELMFNPKAMKKAQEEVRRVFGQKGIVDESGFHELKFLKLVIKE
TLRLHPALPLIPRECMNKSKINGYNIDPKTKVLINVWAIGRDSNIWPEAEKFYPERFLDS
SIDYKGTSYEFIPFGAGKRICPGMMLGTTNLELFLAQLLYHFDWQFPDGVTPETFDMTEA
FSGSINRKYDLNLIPIPFHPLRVE

SEQ ID NO 41, Euphorbia peplus

>CYP726A3
MDLEMPSFLILFSFLILTWIIWKKMNSNSVPPPGPWKLPLLGNILQLRGGPANHRLCDLA
KVYGPVMSIQLGQNPAVVLSSPEAAEQVFKIQGDLFNNRPPALSGKILFYNNSDMTFTPY
GDHWRQIRKITVMEFLSPKRVLSFRSIREEQVSNFIKFLRTKGGSAINFPKALSELTSRI
MLITLLGNKDENEEIVLPAIERVIETANKGAASDTFPTLKFFLDFLTGDKSRMEKVLQET
DIILEAIINEHKKKGTSEHNYLDFLLDKQKKGDLQLPLTNEAIKANLMAMYAGGSETSSK
LIEWTFAEMMKNPETMRKAQEEVRRVFGDKGKVEESRIQELKYLKLVLKESFRIHPPSTL
ITRVCQERTKINGYDIHPKTTILINVWTMGRDPNLWKEPEKFHPERFEDSKIDFRGANME
LTPFGVGKRMCPGITLSTTYVEFLLANLLYHFDWKLPDGVTPATLDMTETLRGTLKKVQD
LILIPIPFSPHQIA

Fig. 20

SEQ ID NO: 42

>CYP726A5
MEFTLSLKKMELQILSFPILFPFLLFILTFLTIIRRKKQNQDCNFPPGPWQFPIIGNIPQ
LLGGLFHHRLSDLAKIHGPIMSIQQGQIPAVVITSVELAKEVLKTQGEIFAGRPQAPAGD
VLYYDCKDIVFAPYGDHWRQMRKICTLEFLSLKRVQSFRSLREENVSGFIKFLSTKANSS
VNLTKSVGNLTSSIMLIKTYGKCDEKLLAMLEKVKQAVLETSSGTDLFPSLKFIQYINGE
KSRMARVQKEMDKMLEQIIKEHKVQYKFGDNNLLQVLLDQQQNGDLELPLTNEIIKANIM
EIFFGGSHTSSKTVEWAMSELMKNPESMTKAQAEVRQVFGETGNVEESRMQEVKYLKSVI
KETLRLHPPATFVTRECRQKTKVNGYDIYPKTVVHVNTYAICRDPDVWVEPEKFYPERFE
ENQIDYKGAHMELIPFGAGKRICPGISLATTYVEVLLANLLYHFDWKLPYGMTPANLDMT
EMHCGALARKHDLCLIPIPFSKI

SEQ ID NO: 43

>CYP726A6
MKMLEQIPSLPIIFPLILFIFMLIKLWQKKNHNSIRPPGPRKYPFIGNLPQLLGAPVHQR
LADLAKTYGPVMSIQQGQIPSVVLSSVETAKEVLKIQGEEFAGRPSTMALDITFYDAQDI
AYTEYGDYWRQMKKISTLEFLSAKRVHSFKPVREERISIFLDSLRSKGRSPVNLTRTIYG
LTNSIIQITAFGKNCKTREKLNLDKIREAVVDGTIADLFPRFKFIASLSGAKSRMMRAHK
EIDVVLDEILEEHKANKSTIGNNLMQVLLDFQKNGGLQVPLTTDQIKANMLEMFLSGSHT
SSKITEWTMAELMRAPETMRKAQEEVRRVFSEIGRVDESRIHECKYVKNVLKEAFRLHPP
GPMVVRQCREITKVNGYEILPGTTVFINVWAIGRDPEVWTEPEKFNPDRFEDSEIDYRGA
HMELIPFGAGKRICPGLTLAVVYVELLLANLLYHFDWEFPDGVTQKTLDMTEFFRGTLNR
KEDLYLIPVPSSSLPKN

SEQ ID NO: 44, *Jatropha curcas*

>CYP726A20
MEHQILSFPVLFSLLLFILVLLKVSKKLYKHDSKPPPGPWKLPFIGNLIQLVGDTPHRRL
TALAKTYGPVMGVQLGQVPFLVVSSPETAKEVMKIQDPVFAERPLVLAGEIVLYNRNDIV
FGSYGDQWRQMRKFCTLELLSTKRVQSFRPVREEEVASFVKLMRTKKGTPVNLTHALFAL
TNSIVARNAVGHKSKNQEALLEVIDDIVVSGGGVSIVDIFPSLQWLPTAKRERSRIWKLH
QNTDEILEDILQEHRAKRQATASKNWDRSEADNLLDVLLDLQQSGNLDVPLTDVAIKAAI
IDMFGAGSDTSSKTAEWAMAELMRNPEVMKKAQEELRNFFGENGKVEEAKLHELKWIKLI
IKETLRLHPAVAVIPRVCREKTKVYGYDVEPGTRVFINVWSIGRDPKVWSEAERFKPERF
IDSAIDYRGLNFELIPFGAGKRICPGMTLGMANLEIFLANLLYHFDWKFPKGVTAENLDM
NEAFGGAVKRKVDLELIPIPFRP

SEQ ID NO: 45

>CYP726A21
MEQQILSFPVLFSFLLFLLVLLKVSKKLSKHDSNSPPGPWKLPFLGNILQLAGDLPHRRI
TELAKKYGPVMSIKLGQHPYLVVSSPETAKEVMRTQDPIFADRPLVLAGELVLYNRNDIG
FGLYGDQWRQMRKFCALELLSTKRVQSFRSVREEEIAEFVKSLRSKEGSSVNLSHTLFAL
TNSIIARNTVGHKSKNQEALLKIIDDIVESLGGLSTVDIFPSLKWLPSVKRERSRIWKLH
CETDEILEGILEEHKANRQAAAFKNDDGSQADNLLDVLLDLQQNGNLEVPLTDVNIKAVI
LGMFGAGSDTSSKTTEWAMAELMKNPEIMKKAQEELRSLFGESGYVDEAKLHEIKWLKLI
INETLRLHPAVTLIPRLCREKTKVSGYDVYPNTRVFINTWAIGRDPTIWSEPEKFVPERF
IDSSIDYRGNHFEYTPFGAGRRICPGMAFGMVNLEIFLANLLYHFDWKLPKGITSENLDM
TENFGGVIKRKQDLELIPAPFRP

SEQ ID NO: 46

>CYP726A22
MEQQILSVSVLSSFVLFLFVLLKVSKKLYKHDSNPPPGPWKLPFLGNILQLAGDAPHHRF
AELARTYGPVMGIKLGEIPFLVVSSPEAAKEVMKIQDPIFAERALVFANDVLNYNRNVMV
FGSYGYQWRQLRKFCTLALLSAKRVQSFQSVRKEEMADFVNFLRSKEGSSVNLTHTIFAF
TNSIIARNAVGHKTKNQETLLTCIDGIIYTGGVNIADVFPSLKWLPSVKREKSRVMKLHY
ETDKILEDILQEHKANKQAWVSEDGDGRKAGNFVDVLLDLQQSGNLDFPLTDVTIKASTI
DAFVGGSDTSSKTTEWAMAELMRKPEIMKKAQEELRSVFGEKGYIEEAKLQELKWLKLII
KETMRLHPVLSLLPRVCKQKTKVSGYDVYPGTQVLVNVWALGRDPKHWSEPEKFNPERFI
DSSIDYLGNHFEYLPFGAGKRVCPGIALGMVHMENFLANLLFHFDWKFPKGITAENLDMT
DAFGGVMKRKVDLELIPIPYHP

Fig. 21

SEQ ID NO: 47

>CYP726A23
MEHQILSFPALFSFLLFLLVLLKVSKKLYKHDSNPPPGPWKLPFLGNILQLAGDTFHRRL
TELAKTHGPVMSINVGQIPYVVVSSPETAKEVMKIQDPVFADHPVVLAAEVILYSPYDIF
FAPYGDHLKQMRKFCTVELLSTKRVQSFRSVREEEVADFVKFLRSKEGSSVNLTHTLFAL
TNSIVARTAVGHRSKNQEGLLKVIDEAVLASSGVNIADIFPSLQWLPSVKRERSRIWKTH
RETDKILEDVLQEHRANRKAAVPKNGDQSQADNLLDVLLDLQESGNLDVPLPDAAIKGTI
MEMFGAGSDTSSKTVEWAMAELMRNPEVMRKAQEELRSFFGENGEVEDAKIQELKCLKLI
IKETLRLHPPGAVIPRLCRERTKVAGYDIYPNTKIFVNTWAIGRDPEIWSEAEKFNPDRF
IDSSIDYKGNNFELIPFGAGRRICPGITLASANMELFLANLLYHFDWKFPQGITAENLDM
NECFGGAVKRKVDLELIPIPFRT

SEQ ID NO: 48

>CYP726A24
MLSFPVIFSFLLFLLVLLKVSKKLCKDNSIPPPGPWQLPFLGNIFQLAGYQFHIRLSELG
QTYGPVMGIKVGQVPFLIVSSPEMAKEVLKVQDPTFVDRPVVLAAELVMYGGHDIVYAPY
GDQWRQMRKFCTLELLSTKRVQSFRSVREEEAGEFVKFLLSKEGSSVNLTHALYALSNSM
VARSTVGHKTKNQEALLNVIDDTVSTAAGTNIADIFPSLKWLPTVKRQMSRIWKSHCQTD
EILEGILREHRAKRQTAASKNGDRAEADNLLDVLLDLQQRGDLDVPLTDINIKGAILEMF
GAGSDTSTKTLEWAMSELMRNPKMMKKVQQELRSFFGENGKVEEAKLQELKWLKLIIKET
LRLHPPIAVIPRLCRERTKVCGYDVYPNTRVFVNVWAMGRDPKIWNEAEKFNPERFIDSS
IDYRGNNFELIPFGAGKRICPGITLAIVHVETVLANLLYHFDWKFPEGVTAENFDMNETF
AGIIRRKVDLELIPVAFRP

SEQ ID NO: 49

>CYP726A25
MDHRILSFPFLMLSLLLPFVFELLKIWKKSNNNPPPGPWRLPLIGNIHQLGGRHQPHLRL
TDLARTYGPVMRLQLGQIEAVVISSAETAKQVMKTQESQFLGRPSLLAADIMLYNRTDIS
FAPYGDYWRQMKKIAVVELLSAKRVQAYKSVMDEEVSNFINFLYSKAGSPVNLTKTFYSL
GNGIIAKTSIGKKFKKQETFLKVVDKAIRVAGGFSVGDAFPSFKLIHLITGISSTLHTAH
QEADEILEEIISEHRASKTADGDDYEADNILGVLLDIQERGNLQVPLTTDNIKAIILDMF
AGASDTSLTTAEWAMAEMVKHPRIMKKAQDEVRRTLNQEGNVANLLPELKYLKLVIKETL
RLHPPVALIPRECDGRCELNGYDVNPKTKILVNAWAIGRDHNLWNDPERFDPERFLDNSS
DFRGTDFKFIPFGAGKRICPGITMAITIIEVLLAQLLYHFDWKLPDGAKPESLDMSDTFG
LVVKRRIDLNLIPIP

SEQ ID NO: 50

>CYP726A26
MEYQILSSPTLIALLVFVATVVIKLWKRPTIANNNPPPGPWKLPLIGNLHNLFGRDQPHH
RLRDLAGKYGAVMGFQLGQVPTVVISSAEIAKQVLKTHEFQFIDRPSLLAADIVLYNRSD
IIFAPYGDYWRQIKKIAILELLSSKRVQSFKSVREEEVSSFFKFLYSKAGSPVNLSRTLL
SLTNGIIAKTSIGKKCKRQEEIIAVITDAIKATGGFSVADVFPSFKFLHIITGISSTIRR
IHREADTILEEIMDEHKANNESKNEPDNILDVLLDIQQRGNLEFPLTADNIKAIILEMFG
AASDTSSVTIEWAMSEMMKNPWTMKKAQEEVREVFNGTGDVSEASLQELQYLKLVIKETL
RLHPPLTLIPRECNQKCQINEYDIYPKTRVLVNAWAIGRDPNWWTDPERFDPERFRCGSV
DFKGTDFEFIPFGAGKRMCPGITMAMANIELILAQLLYHFNWELPGKAKPETLDMSESFG
LAVKRKVELNLIPTAFNP

SEQ ID NO: 51

>Jcu17062
MEQQILSFPVIFNFLLFLLVLLKVSKKLSKHDSNSPPGPWKLPFLGNFLQLAGDLPHRRI
TELAKKYGPVMSIKLGQHPYLVVSSPETAKEVMRTQDPIFADRPLVLAGELVLYNRNDIG
FGLYGDQWRQMRKFCALELLSTKRIQSFRSVREEEIAVFVKSLRSKEGSSVNLSHTLFAL
TNSIIARNTVGHKSKNQEALLKIIDDIVESLGGLSTVDIFPSLKWLPSVKRERSRIWKLH
CETDEILEGILEEHKANRQAAAFKNDDGSQADNLLDVLLDLQQNGNLQVPLTDVNIKAVI
LGMFGAGSDTSSKTTEWAMAELMKNPEIMKNAQEELRSLFGESGNVDEAKLHEIKWLKLI
INETLRLHPAVTLIPRLCREKTKISGYDVYPNTRVFINTWAIGRDPIIWTEPEKFVPERF
IDSSIDYRGNHFEYTPFGAGRRICPGMTFGMVNLEIFLANLLYHFDWKLPKGITSENLDM
TENFGGVIKRKQDLELIPVPFRP

Fig. 22

SEQ ID NO: 52

>Jcu17064
MEDQILSFQVLFSFLLFLFVLFKVSKKLYKHGSNPPPGPLKLPFLGNILQLAGDVPHRRL
TALAKTYGPVMGIKLGQIPFLVVSSPETAKEVMKIQDPVFAERAPLLAGEIVLYNRNDII
FGLYGDQWRQMRKICTLELLSAKRVQSFRSVREEEVADLVKFLGSKEGSPVNLTHTLFAL
ANSIIARNTVGQKSKNQEALLRLIDDIIELTGSVSIADIFPSLKWLPSVQRDRSRIRKLH
YETDEILEDILQEHRANRQAAASRKGDRRGADNLLDVLLYLQETGNLDVPLTDVAIKAAI
IDMFGAGSDTSSKTVEWAMAELMRNPEIMKKAQEELRNFFGENGKVDEAKLQELKWLNLI
NKETLRLHPAAAVVPRVCRERTKVSGYDVYPGTRVFINAWAIGRDPKVWSEAEKFKPERF
IDSAIDYRGTNFELIPFGAGKRICPGMTLGMANLEIFLANLLYHFDWKFPKGVTAENLDM
NEAFGAAVKRKVDLELVPIPFRP22

DITERPENOID SYNTHESIS

CROSS REFERENCE TO RELATED APPLICATIONS

This is the U.S. National Stage of International Application No. PCT/GB2015/050035, filed Jan. 9, 2015, which was published in English under PCT Article 21(2), which in turn claims the benefit of Great Britain Application No. 1400512.8, filed Jan. 13, 2014.

FIELD OF THE INVENTION

The present disclosure relates to nucleic acids that encode cytochrome P450 polypeptides involved in the biosynthesis of plant derived diterpenoids and including plants or microbes that express said cytochrome P450 polypeptides.

BACKGROUND TO THE INVENTION

Terpenes or terpenoids are a structurally diverse and a very large group of organic compounds commonly found in plants ranging from essential and universal primary metabolites such as sterols, carotenoids and hormones to more complex and unique secondary metabolites. Terpenes are hydrocarbons assembled of five carbon terpene or isoprene subunits providing the carbon skeleton. Terpenoids are modified terpenes which typically comprise also oxygen; however, terpenes and terpenoids are often used interchangeably. Terpenoids are classified accordingly to the length of the isoprene units as for example hemiterpenoids consisting of one, monoterpenoids consisting of two, sesquiterpenoids consisting of three and diterpenoids consisting of four isoprene units.

The early core steps in terpenoid biosynthesis are well characterised in both eukaryotes and prokaryotes. The primary building blocks are isopentenyl diphosphate (IPP) and dimethylallyl diphosphate (DMAPP), which are used for the synthesis of the compounds geranyl diphosphate (GPP), farnesyl diphosphate (FPP) and geranylgeranyl diphosphate (GGPP).

Geranylgeranyl diphosphate (GGPP) is the precursor for the synthesis of a variety of diterpenes, which first steps are catalysed by diterpene synthases. For the conversion of terpenes to terpenoids, a number of enzymes may be involved. Cytochrome P450s are typically required for the addition of oxygen, whereas BAND acyltransferase are often involved in the addition of acyl groups. The enzymes involved in the biosynthesis of some diterpenes, for example paclitaxel, have been partially characterised, with sequences for a diterpene synthase (Wildung & Croteau, 1996. J. Biol. Chem. 271: 9201-9204) a number of cytochrome P450s (Schoendorf et al., 2001. PNAS 98: 1501-1506; Jennewein et al. 2001: PNAS 98: 13595-13600; Jennewein et al. 2003. Arch. Biochem. Biophys. 413: 262-270; Jennewein et al., 2004. Chem. Biol. 11: 379-387; Chau et al., 2004a: Chem. Biol. 11: 663-672; Chau et al. 2004b. Arch. Biochem. Biophys. 427: 48-57) and a number of acyltransferases (Walker & Croteau, 2000. PNAS 97: 583-587; Walker et al., 2000. Arch. Biochem. Biophys. 274: 371-380; Chau et al 2004c. Arch. Biochem. Biophys. 430: 237-246) being described. However, the enzymes involved in the synthesis of the vast majority of diterpenoids produced by other plant species remain unknown.

Diterpenes form the basis for many biologically important compounds such as retinol, retinal, and phytol and some compounds have shown antimicrobial and anti-inflammatory properties. A large number of diterpenes have been isolated from plants belonging to the family of Euphorbiaceae. The Euphorbiaceae or spurge family is a large family of flowering plants found all over the world, with some synthesising compounds of considerable biological activity such as ingenol mebutate (*Euphorbia peplus*), resiniferatoxin (*E. resinifera*), prostratin (*E. cornigera*), jatrophanes (*Jatropha* sp.) and jatrophone (*Jatropha* sp.).

Although the beneficial effects of some diterpenes are known such as ingenol mebutate which is licensed to treat actinic keratosis, or resiniferatoxin which is currently being tested in Phase II clinical trials for its analgesic effects, sufficient supply is still hampered by the lack of or inefficient chemical synthesis. Similarly, extraction of active compounds from the plant biomass is a complex process requiring several steps and various solvents, and moreover the yield is typically very low. Methods and processes enabling extraction of diterpenes from plants are disclosed in U.S. Pat. Nos. 4,361,697 and 6,228,996.

Bacteria and yeast have been successfully used to engineer biosynthetic pathways for the production of some desired chemical compounds from inexpensive carbon sources. The terpenoid artemisinic acid, a precursor for the anti-malaria drug artemesinin, has been successfully synthesised in yeast using this approach. Bacterial or yeast expression systems are often advantageous over other expression systems as they are easily maintained and various methods are available allowing straightforward expression of transgenic genes. The biosynthesis of isoprenoids using a genetically modified bacterial host cell comprising one or more enzymes of the mevalonate pathway is disclosed in patent application WO2008/039499.

The applicants of the present application have identified a number of cytochrome P450 encoding genes involved in the biosynthesis of diterpenoids.

STATEMENTS OF INVENTION

According to an aspect of the invention there is provided a nucleic acid molecule that is isolated from a Euphorbiaceae plant wherein said isolated nucleic acid molecule encodes a cytochrome P450 polypeptide characterized in that said cytochrome P450 polypeptide is involved in the biosynthesis of diterpenoids or intermediates in the biosynthesis of diterpenoids.

In a preferred embodiment of the invention said isolated nucleic acid molecule that encodes a cytochrome P450 polypeptide is selected from the group consisting of:

- i) a nucleotide sequence as represented by the sequence in SEQ ID NO: 1, 2, 3, 4, 5, 6, 7,8, 9, 10, 11, 12, 13, 14, 15, 16, 17, 18, 19, 20, 21, 22, 23, 24, 25 or 26;
- ii) a nucleotide sequence wherein said sequence is degenerate as a result of the genetic code to the nucleotide sequence defined in (i);
- iii) a nucleic acid molecule the complementary strand of which hybridizes under stringent hybridization conditions to the sequence in SEQ ID NO: 1, 2, 3, 4, 5, 6, 7,8, 9, 10, 11, 12, 13, 14, 15, 16, 17, 18, 19, 20, 21, 22, 23, 24, 25 or 26, wherein said nucleic acid molecule encodes polypeptides involved in the biosynthesis of diterpenoids or intermediates in the biosynthesis of diterpenoids;
- iv) a nucleotide sequence that encodes a polypeptide comprising an amino acid sequence as represented in SEQ ID NO: 27, 28, 29, 30, 31, 32, 33, 34, 35, 36, 37, 38, 39, 40, 41, 42, 43, 44, 45, 46, 47, 48, 49, 50, 51 or 52;

v) a nucleotide sequence that encodes a polypeptide comprising an amino acid sequence wherein said amino acid sequence is modified by addition, deletion or substitution of at least one amino acid residue as represented in iv) above and which has retained or enhanced diterpenoid biosynthetic activity.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, N.Y., 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences That Share at Least 90% Identity to Hybridize)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Allows Sequences That Share at Least 80% Identity to Hybridize)

Hybridization: 5×-6×SSC at 65° C-70° C. for 16-20 hours

Wash twice: 2×SSC at RT for 5-20 minutes each

Wash twice: 1×SSC at 55° C-70° C. for 30 minutes each

Low Stringency (Allows Sequences That Share at Least 50% Identity to Hybridize)

Hybridization: 6×SSC at RT to 55° C. for 16-20 hours

Wash at least twice: 2×-3×SSC at RT to 55° C. for 20-30 minutes each.

In a preferred embodiment of the invention said nucleic acid molecule comprises or consists of a nucleotide sequence as represented SEQ ID NO: 1 wherein said nucleic acid molecule encodes a polypeptide with casbene-oxidase activity.

In a preferred embodiment of the invention said nucleic acid molecule comprises or consists of a nucleotide sequence as represented SEQ ID NO: 2 wherein said nucleic acid molecule encodes a polypeptide with casbene-oxidase activity.

In a preferred embodiment of the invention said nucleic acid molecule comprises or consists of a nucleotide sequence as represented SEQ ID NO: 3 wherein said nucleic acid molecule encodes a polypeptide with casbene-oxidase activity.

In a preferred embodiment of the invention said nucleic acid molecule comprises or consists of a nucleotide sequence as represented SEQ ID NO: 4 wherein said nucleic acid molecule encodes a polypeptide with casbene-oxidase activity.

In a preferred embodiment of the invention said nucleic acid molecule comprises or consists of a nucleotide sequence as represented SEQ ID NO: 5 wherein said nucleic acid molecule encodes a polypeptide with casbene-oxidase activity.

In a preferred embodiment or aspect of the invention said nucleic acid molecule comprises or consists of a nucleotide sequence as represented SEQ ID NO: 6 wherein said nucleic acid molecule encodes a polypeptide with casbene-oxidase activity.

In a preferred embodiment of the invention said nucleic acid molecule comprises or consists of a nucleotide sequence as represented SEQ ID NO: 7 wherein said nucleic acid molecule encodes a polypeptide with casbene-oxidase activity.

In a preferred embodiment of the invention said nucleic acid molecule comprises or consists of a nucleotide sequence as represented SEQ ID NO: 8 wherein said nucleic acid molecule encodes a polypeptide with casbene-5-oxidase activity.

In a preferred embodiment of the invention said nucleic acid molecule comprises or consists of a nucleotide sequence as represented SEQ ID NO: 9 wherein said nucleic acid molecule encodes a polypeptide with neoembrene-5-oxidase activity.

In a preferred embodiment of the invention said nucleic acid molecule comprises or consists of a nucleotide sequence as represented SEQ ID NO: 10 wherein said nucleic acid molecule encodes a polypeptide with 5-keto-casbene 7,8-epoxidase activity.

In a preferred embodiment of the invention said nucleic acid molecule comprises or consists of a nucleotide sequence as represented SEQ ID NO: 11 wherein said nucleic acid molecule encodes a polypeptide with cytochrome P450 activity.

In a preferred embodiment of the invention said nucleic acid molecule comprises or consists of a nucleotide sequence as represented SEQ ID NO: 12 wherein said nucleic acid molecule encodes a polypeptide with cytochrome P450 activity.

In a preferred embodiment of the invention said nucleic acid molecule comprises or consists of a nucleotide sequence as represented SEQ ID NO: 13 wherein said nucleic acid molecule encodes a polypeptide with cytochrome P450 activity.

In a preferred embodiment of the invention said nucleic acid molecule comprises or consists of a nucleotide sequence as represented SEQ ID NO: 14 wherein said nucleic acid molecule encodes a polypeptide with cytochrome P450 activity.

In a preferred embodiment of the invention said nucleic acid molecule comprises or consists of a nucleotide sequence as represented SEQ ID NO: 15 wherein said nucleic acid molecule encodes a polypeptide with cytochrome P450 activity.

In a preferred embodiment of the invention said nucleic acid molecule comprises or consists of a nucleotide sequence as represented SEQ ID NO: 16 wherein said nucleic acid molecule encodes a polypeptide with cytochrome P450 activity.

In a preferred embodiment of the invention said nucleic acid molecule comprises or consists of a nucleotide sequence as represented SEQ ID NO: 17 wherein said nucleic acid molecule encodes a polypeptide with cytochrome P450 activity.

In a preferred embodiment of the invention said nucleic acid molecule comprises or consists of a nucleotide sequence as represented SEQ ID NO: 18 wherein said nucleic acid molecule encodes a polypeptide with cytochrome P450 activity.

In a preferred embodiment of the invention said nucleic acid molecule comprises or consists of a nucleotide sequence as represented SEQ ID NO: 19 wherein said nucleic acid molecule encodes a polypeptide with cytochrome P450 activity.

In a preferred embodiment of the invention said nucleic acid molecule comprises or consists of a nucleotide sequence as represented SEQ ID NO: 20 wherein said nucleic acid molecule encodes a polypeptide with cytochrome P450 activity.

In a preferred embodiment of the invention said nucleic acid molecule comprises or consists of a nucleotide sequence as represented SEQ ID NO: 21 wherein said nucleic acid molecule encodes a polypeptide with cytochrome P450 activity.

In a preferred embodiment of the invention said nucleic acid molecule comprises or consists of a nucleotide sequence as represented SEQ ID NO: 22 wherein said nucleic acid molecule encodes a polypeptide with cytochrome P450 activity.

In a preferred embodiment of the invention said nucleic acid molecule comprises or consists of a nucleotide sequence as represented SEQ ID NO: 23 wherein said nucleic acid molecule encodes a polypeptide with cytochrome P450 activity.

In a preferred embodiment of the invention said nucleic acid molecule comprises or consists of a nucleotide sequence as represented SEQ ID NO: 24 wherein said nucleic acid molecule encodes a polypeptide with cytochrome P450 activity.

In a preferred embodiment of the invention said nucleic acid molecule comprises or consists of a nucleotide sequence as represented SEQ ID NO: 25 wherein said nucleic acid molecule encodes a polypeptide with cytochrome P450 activity.

In a preferred embodiment of the invention said nucleic acid molecule comprises or consists of a nucleotide sequence as represented SEQ ID NO: 26 wherein said nucleic acid molecule encodes a polypeptide with cytochrome P450 activity.

According to a further aspect of the invention there is provided an isolated polypeptide selected from the group consisting of:

i) a polypeptide comprising or consisting of an amino acid sequence as represented in SEQ ID NO: 27; or ii) a modified polypeptide comprising or consisting of a modified amino acid sequence wherein said polypeptide is modified by addition, deletion or substitution of at least one amino acid residue of the sequence presented in SEQ ID NO: 27 and which has retained or enhanced casbene-5-oxidase activity.

According to a further aspect of the invention there is provided an isolated polypeptide selected from the group consisting of:

i) a polypeptide comprising or consisting of an amino acid sequence as represented in SEQ ID NO: 28; or ii) a modified polypeptide comprising or consisting of a modified amino acid sequence wherein said polypeptide is modified by addition, deletion or substitution of at least one amino acid residue of the sequence presented in SEQ ID NO: 28 and which has retained or enhanced casbene-oxidase activity.

According to a further aspect of the invention there is provided an isolated polypeptide selected from the group consisting of:

i) a polypeptide comprising or consisting of an amino acid sequence as represented in SEQ ID NO: 29; or ii) a modified polypeptide comprising or consisting of a modified amino acid sequence wherein said polypeptide is modified by addition, deletion or substitution of at least one amino acid residue of the sequence presented in SEQ ID NO: 29 and which has retained or enhanced casbene-oxidase activity.

According to a further aspect of the invention there is provided an isolated polypeptide selected from the group consisting of:

i) a polypeptide comprising or consisting of an amino acid sequence as represented in SEQ ID NO: 30; or ii) a modified polypeptide comprising or consisting of a modified amino acid sequence wherein said polypeptide is modified by addition, deletion or substitution of at least one amino acid residue of the sequence presented in SEQ ID NO: 30 and which has retained or enhanced casbene-oxidase activity.

According to a further aspect of the invention there is provided an isolated polypeptide selected from the group consisting of:

i) a polypeptide comprising or consisting of an amino acid sequence as represented in SEQ ID NO: 31; or ii) a modified polypeptide comprising or consisting of a modified amino acid sequence wherein said polypeptide is modified by addition, deletion or substitution of at least one amino acid residue of the sequence presented in SEQ ID NO: 31 and which has retained or enhanced casbene-oxidase activity.

According to a further aspect of the invention there is provided an isolated polypeptide selected from the group consisting of:

i) a polypeptide comprising or consisting of an amino acid sequence as represented in SEQ ID NO: 32; or ii) a modified polypeptide comprising or consisting of a modified amino acid sequence wherein said polypeptide is modified by addition, deletion or substitution of at least one amino acid residue of the sequence presented in SEQ ID NO: 32 and which has retained or enhanced casbene-oxidase activity.

According to a further aspect of the invention there is provided an isolated polypeptide selected from the group consisting of:

i) a polypeptide comprising or consisting of an amino acid sequence as represented in SEQ ID NO: 33; or ii) a modified polypeptide comprising or consisting of a modified amino acid sequence wherein said polypeptide is modified by addition, deletion or substitution of at least one amino acid residue of the sequence presented in SEQ ID NO: 33 and which has retained or enhanced casbene-oxidase activity.

According to a further aspect of the invention there is provided an isolated polypeptide selected from the group consisting of:

i) a polypeptide comprising or consisting of an amino acid sequence as represented in SEQ ID NO: 34; or ii) a modified polypeptide comprising or consisting of a modified amino acid sequence wherein said polypeptide is modified by addition, deletion or substitution of at least one amino acid residue of the sequence presented in SEQ ID NO: 34 and which has retained or enhanced casbene-5-oxidase activity.

According to a further aspect of the invention there is provided an isolated polypeptide selected from the group consisting of:

i) a polypeptide comprising or consisting of an amino acid sequence as represented in SEQ ID NO: 35; or ii) a modified polypeptide comprising or consisting of a modified amino acid sequence wherein said polypeptide is modified by addition, deletion or substitution of at least one amino acid residue of the sequence presented in SEQ ID NO: 35 and which has retained or enhanced neocembrene-5-oxidase activity.

According to a further aspect of the invention there is provided an isolated polypeptide selected from the group consisting of:

i) a polypeptide comprising or consisting of an amino acid sequence as represented in SEQ ID NO: 36; or ii) a modified polypeptide comprising or consisting of a modified amino acid sequence wherein said polypeptide is modified by addition, deletion or substitution of at least one amino acid residue of the sequence presented in SEQ ID NO: 36 and which has retained or enhanced 5-keto-casbene 7,8-epoxidase activity.

According to a further aspect of the invention there is provided an isolated polypeptide selected from the group consisting of:

i) a polypeptide comprising or consisting of an amino acid sequence as represented in SEQ ID NO: 37; or ii) a modified polypeptide comprising or consisting of a modified amino acid sequence wherein said polypeptide is modified by addition, deletion or substitution of at least one amino acid residue of the sequence presented in SEQ ID NO: 37 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 38; or ii) a modified polypeptide comprising or consisting of a modified amino acid sequence wherein said polypeptide is modified by addition, deletion or substitution of at least one amino acid residue of the sequence presented in SEQ ID NO: 38 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 39; or ii) a modified polypeptide comprising or consisting of a modified amino acid sequence wherein said polypeptide is modified by addition, deletion or substitution of at least one amino acid residue of the sequence presented in SEQ ID NO: 39 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 40; or ii) a modified polypeptide comprising or consisting of a modified amino acid sequence wherein said polypeptide is modified by addition, deletion or substitution of at least one amino acid residue of the sequence presented in SEQ ID NO: 40 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 41; or ii) a modified polypeptide comprising or consisting of a modified amino acid sequence wherein said polypeptide is modified by addition, deletion or substitution of at least one amino acid residue of the sequence presented in SEQ ID NO: 41 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 42; or ii) a modified polypeptide comprising or consisting of a modified amino acid sequence wherein said polypeptide is modified by addition, deletion or substitution of at least one amino acid residue of the sequence presented in SEQ ID NO: 42 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 43; or ii) a modified polypeptide comprising or consisting of a modified amino acid sequence wherein said polypeptide is modified by addition, deletion or substitution of at least one amino acid residue of the sequence presented in SEQ ID NO: 43 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 44; or ii) a modified polypeptide comprising or consisting of a modified amino acid sequence wherein said polypeptide is modified by addition, deletion or substitution of at least one amino acid residue of the sequence presented in SEQ ID NO: 44 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 45; or ii) a modified polypeptide comprising or consisting of a modified amino acid sequence wherein said polypeptide is modified by addition, deletion or substitution of at least one amino acid residue of the sequence presented in SEQ ID NO: 45 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 46; or ii) a modified polypeptide comprising or consisting of a modified amino acid sequence wherein said polypeptide is modified by addition, deletion or substitution of at least one amino acid residue of the sequence presented in SEQ ID NO: 46 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 47; or ii) a modified polypeptide comprising or consisting of a modified amino acid sequence wherein said polypeptide is modified by addition, deletion or substitution of at least one amino acid residue of the sequence presented in SEQ ID NO: 47 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 48; or ii) a modified polypeptide comprising or consisting of a modified amino acid sequence wherein said polypeptide is modified by addition, deletion or substitution of at least one amino acid residue of the sequence presented in SEQ ID NO: 48 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 49; or ii) a modified polypeptide comprising or consisting of a modified amino acid sequence wherein said polypeptide is modified by addition, deletion or substitution of at least one amino acid residue of the sequence presented in SEQ ID NO: 49 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 50; or ii) a modified polypeptide comprising or consisting of a modified amino acid sequence wherein said polypeptide is modified by addition, deletion or substitution of at least one amino acid residue of the sequence presented in SEQ ID NO: 50 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 51; or ii) a modified polypeptide comprising or consisting of a modified amino acid sequence wherein said polypeptide is modified by addition, deletion or substitution of at least one amino acid residue of the sequence presented in SEQ ID NO: 51 and which has retained or enhanced cytochrome P450 activity.

According to a further aspect of the invention there is provided an isolated polypeptide selected from the group consisting of:

i) a polypeptide comprising or consisting of an amino acid sequence as represented in SEQ ID NO: 52; or ii) a modified polypeptide comprising or consisting of a modified amino acid sequence wherein said polypeptide is modified by addition, deletion or substitution of at least one amino acid residue of the sequence presented in SEQ ID NO: 52 and which has retained or enhanced cytochrome P450 activity.

A modified polypeptide as herein disclosed may differ in amino acid sequence by one or more substitutions, additions, deletions, truncations that may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants that retain or enhance the same biological function and activity as the reference polypeptide from which it varies.

In a preferred embodiment of the invention the variant polypeptides have at least 60%, 65%, 70%, 75%, 80%, 85%, 90%, 95% identity, and at least 99% identity with the full length amino acid sequence illustrated herein.

According to a further aspect of the invention there is provided a vector comprising a nucleic acid molecule according to the invention.

Preferably the nucleic acid molecule in the vector is under the control of, and operably linked to, an appropriate promoter or other regulatory elements for transcription in a host cell such as a microbial, (e.g. bacterial, yeast), or plant cell. The vector may be a bi-functional expression vector which functions in multiple hosts. In the case of genomic DNA this may contain its own promoter or other regulatory elements and in the case of cDNA this may be under the control of an appropriate promoter or other regulatory elements for expression in the host cell.

By “promoter” is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells. Constitutive promoters include, for example CaMV 35S promoter (Odell et al. (1985) Nature 313, 9810-812); rice actin (McElroy et al. (1990) Plant Cell 2: 163-171); ubiquitin (Christian et al. (1989) Plant Mol. Biol. 18 (675-689); pEMU (Last et al. (1991) Theor. Appl. Genet. 81: 581-588); MAS (Velten et al. (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142, each of which is incorporated by reference.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88: 10421-10425 and McNellis et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al. (1997)

Plant Cell Physiol. 38(7): 792-803; Hansen et al. (1997) Mol. Gen. Genet. 254(3): 337-343; Russell et al. (1997) Transgenic Res. 6(2): 157-168; Rinehart et al. (1996) Plant Physiol. 112(3): 1331-1341; Van Camp et al. (1996) Plant Physiol. 112(2): 525-535; Canevascni et al. (1996) Plant Physiol. 112(2): 513-524; Yamamoto et al. (1994) Plant Cell Physiol. 35(5): 773-778; Lam (1994) Results Probl. Cell Differ. 20: 181-196; Orozco et al. (1993) Plant Mol. Biol. 23(6): 1129-1138; Mutsuoka et al. (1993) Proc. Natl. Acad. Sci. USA 90 (20): 9586-9590; and Guevara-Garcia et al (1993) Plant J. 4(3): 495-50.

"Operably linked" means joined as part of the same nucleic acid molecule, suitably positioned and oriented for transcription to be initiated from the promoter. DNA operably linked to a promoter is "under transcriptional initiation regulation" of the promoter. In a preferred aspect, the promoter is a tissue specific promoter, an inducible promoter or a developmentally regulated promoter Particular of interest in the present context are nucleic acid constructs which operate as plant vectors. Specific procedures and vectors previously used with wide success in plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP194809). If desired, selectable genetic markers may be included in the construct, such as those that confer selectable phenotypes such as resistance to herbicides (e.g. kanamycin, hygromycin, phosphinothricin, chlorsulfuron, methotrexate, gentamycin, spectinomycin, imidazolinones and glyphosate).

According to a further aspect of the invention there is provided a transgenic cell transformed or transfected with a nucleic acid molecule or vector according to the invention.

According to an aspect of the invention there is provided a transgenic cell transformed or transfected with an expression vector adapted to express a nucleic acid molecule comprising at least one nucleotide sequence which is at least 70% identical to SEQ ID NO: 1 and encodes a polypeptide that has casbene oxidase activity.

In a preferred embodiment of the invention said transgenic cell is transformed or transfected with an expression vector comprising a nucleotide sequence that is at least 69%, 70%, 71%, 72%, 73%, 74%, 76%, 78%, 80%, 85%, 90%, 95%, 98% or 99% identical to SEQ ID NO 1.

In a further preferred embodiment of the invention said transgenic cell is transformed or transfected with a vector comprising a nucleotide sequence selected form the group consisting of SEQ ID NO: 1, 2, 3, 4, 5, 6, 7 or 8.

In a further preferred embodiment of the invention said transgenic cell is transformed or transfected with an expression vector comprising one or more additional nucleotide sequences encoding one or more additional polypeptides involved in the biosynthesis of diterpenes and diterpenoids or intermediates selected from the group consisting of:

i) a nucleic acid molecule comprising a nucleotide sequence that is at least 71% identical over the full length sequence set forth in SEQ ID NO: 10 and encodes a polypeptide with 5-keto-casbene 7,8-epoxidase activity; and/or
ii) a nucleic acid molecule comprising a nucleotide sequence that is at least 75% identical over the full length sequences set forth in SEQ ID NO 11, 12, 13, 14, 15, 16, 17, 18, 19, 20, 21, 22, 23, 24, 25 or 26 and encodes a polypeptide with cytochrome P450 activity.

According to a further aspect of the invention there is provided a transgenic cell is transformed or transfected with a vector comprising i) a nucleic acid molecule comprising a nucleotide sequence set forth in SEQ ID NO 9; or
ii) a nucleic acid molecule comprising a nucleotide sequence that is at least 81% identical over the full length sequence set forth in SEQ ID NO: 9 and encodes a polypeptide with neocembrene-5-oxidase activity.

In a preferred embodiment of the invention said transgenic cell is transformed or transfected with an expression vector comprising one or more additional nucleotide sequences encoding one or more additional polypeptides involved in the biosynthesis of diterpenes and diterpenoids or intermediates selected from the group consisting of a nucleic acid molecule comprising a nucleotide sequence that is at least 75% identical over the full length sequences set forth in SEQ ID NO 11, 12, 13, 14, 15, 16, 17, 18, 19, 20, 21, 22, 23, 24, 25 or 26 and encodes a polypeptide with cytochrome P450 activity.

In a preferred embodiment of the invention said cell is a plant cell.

According to a further aspect of the invention there is provided a plant comprising a plant cell according to the invention.

In a preferred embodiment of the invention said plant is from the Euphorbiaceae family.

In a preferred embodiment of the invention said plant is of the genus *Nicotiana* spp, for example *Nicotiana benthamiana* or *Nicotiana tabacum.*

In an alternative preferred embodiment of the invention said cell is a microbial cell; preferably a bacterial or fungal cell (e.g. yeast, *Saccharomyces cerevisiae*).

In a preferred embodiment of the invention said cell is adapted such that the nucleic acid molecule encoding one or more polypeptides according to the invention is over-expressed when compared to a non-transgenic cell of the same species.

According to a further aspect of the invention there is provided a nucleic acid molecule comprising a transcription cassette wherein said cassette includes one or more nucleotide sequences designed with reference to one or more nucleotide sequences selected from the group: SEQ ID NO: 1, 2, 3, 4, 5, 6, 7,8, 9, 10, 11, 12, 13, 14, 15, 16. 17,18, 19, 20, 21, 22, 23, 24, 25 or 26 and is adapted for expression by provision of at least one promoter operably linked to said nucleotide sequence such that both sense and antisense molecules are transcribed from said cassette.

In a preferred embodiment of the invention said cassette is adapted such that both sense and antisense ribonucleic acid molecules are transcribed from said cassette wherein said sense and antisense nucleic acid molecules are adapted to anneal over at least part or all of their length to form a inhibitory RNA or short hairpin RNA.

In a preferred embodiment of the invention said cassette is provided with at least two promoters adapted to transcribe both sense and antisense strands of said ribonucleic acid molecule.

In an alternative preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an ribonucleic acid molecule which forms a double stranded region by complementary base pairing of said first and second parts thereby forming an short hairpin RNA.

A technique to specifically ablate gene function is through the introduction of double stranded RNA, also referred to as small inhibitory/interfering RNA (siRNA) or short hairpin RNA [shRNA], into a cell which results in the destruction of mRNA complementary to the sequence included in the siRNA/shRNA molecule. The siRNA molecule comprises two complementary strands of RNA (a sense strand and an antisense strand) annealed to each other to form a double stranded RNA molecule. The siRNA molecule is typically derived from exons of the gene which is to be ablated. The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In a preferred embodiment of the invention said nucleic acid molecule is part of a vector adapted for expression in a plant cell.

According to a further aspect of the invention there is provided a plant cell transfected with a nucleic acid molecule or vector according to the invention wherein said cell has reduced expression of a polypeptide according to the invention.

According to an aspect of the invention there is provided a process for the modification of one or more diterpenes and diterpenoids comprising:

i) providing a transgenic plant cell according to the invention;
ii) cultivating said plant cell to produce a transgenic plant; and optionally
i) harvesting said transgenic plant, or part thereof.

According to an alternative aspect of the invention there is provided a process for the modification of one or more diterpenes or diterpenoids comprising:

i) providing a transgenic microbial cell according to the invention that expresses one or more nucleic acid molecules according to the invention in culture with at least one diterpene and/or diterpenoid metabolite;
ii) cultivating the microbial cell under conditions that modify one or more diterpenes or diterpenoids; and optionally
iii) isolating said diterpenoid from the microbial cell or cell culture.

In a preferred method of the invention said microbial cell is a bacterial cell or fungal/yeast cell.

If microbial cells are used as organisms in the process according to the invention they are grown or cultured in the manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The diterpenoids produced can be isolated from the organisms as described above by processes known to the skilled worker, for example by extraction, distillation, crystallization, if appropriate precipitation with salt, and/or chromatography. To this end, the organisms can advantageously be disrupted beforehand. In this process, the pH value is advantageously kept between pH 4 and 12, preferably between pH 6 and 9, especially preferably between pH 7 and 8.

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as corn steep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing microorganisms usually also comprise other growth factors such as vitamins or growth promoters, which include, for example, biotin, riboflavin, thiamine, folic acid, nicotinic acid, pantothenate and pyridoxine. Growth factors and salts are frequently derived from complex media components such as yeast extract, molasses, corn steep liquor and the like. It is moreover possible to add suitable precursors to the culture medium. The exact composition of the media compounds heavily depends on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation. However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the diterpenoids present therein.

According to a further aspect of the invention there is provided the use of a gene encoded by a nucleic acid molecule as represented by the nucleic acid sequence in SEQ ID NO: 1, 2, 3, 4, 5, 6, 7,8, 9, 10, 11, 12, 13, 14, 15, 16, 17, 18, 19, 20, 21, 22, 23,24, 25 or 26 or a nucleic acid molecule the complementary strand of which hybridizes under stringent hybridization conditions to the nucleotide sequence in SEQ ID NO: 1, 2, 3, 4, 5, 6, 7,8, 9, 10, 11, 12, 13, 14, 15, 16, 17,18, 19, 20, 21, 22, 23, 24, 25 or 26and encodes a polypeptide with cytochrome P450 activity as a means to identify a locus wherein said locus is associated with altered expression or activity of diterpenoid and diterpene biosynthetic activity.

Mutagenesis as a means to induce phenotypic changes in organisms is well known in the art and includes but is not limited to the use of mutagenic agents such as chemical mutagens [e.g. base analogues, deaminating agents, DNA intercalating agents, alkylating agents, transposons, bromine, sodium azide] and physical mutagens [e.g. ionizing radiation, UV irradiation].

According to a further aspect of the invention there is provided a method to produce a plant of the Euphorbiaceae family that has altered expression of a polypeptide according to the invention comprising the steps of:

- i) mutagenesis of wild-type seed from a plant of the Euphorbiaceae family that does express said polypeptide;
- ii) cultivation of the seed in i) to produce first and subsequent generations of plants;
- iii) obtaining seed from the first generation plant and subsequent generations of plants;
- iv) determining if the seed from said first and subsequent generations of plants has altered nucleotide sequence and/or altered expression of said polypeptide;
- v) obtaining a sample and analysing the nucleic acid sequence of a nucleic acid molecule selected from the group consisting of:
  - a) a nucleic acid molecule comprising a nucleotide sequence as represented in 1, 2, 3, 4, 5, 6, 7,8, 9, 10, 11, 12, 13, 14, 15, 16, 17,18, 19, 20, 21, 22, 23, 24, 25 or 27;
  - b) a nucleic acid molecule that hybridises to the nucleic acid molecule in a) under stringent hybridisation conditions and that encodes a polypeptide with casbene oxidase or cytochrome P450 activity; and optionally
- vi) comparing the nucleotide sequence of the nucleic acid molecule in said sample to a nucleotide sequence of a nucleic acid molecule of the original wild-type plant.

In a preferred method of the invention said nucleic acid molecule is analysed by a method comprising the steps of:

- i) extracting nucleic acid from said mutated plants;
- ii) amplification of a part of said nucleic acid molecule by a polymerase chain reaction;
- iii) forming a preparation comprising the amplified nucleic acid and nucleic acid extracted from wild-type seed to form heteroduplex nucleic acid;
- iv) incubating said preparation with a single stranded nuclease that cuts at a region of heteroduplex nucleic acid to identify the mismatch in said heteroduplex; and
- v) determining the site of the mismatch in said nucleic acid heteroduplex.

In a preferred method of the invention said plant of the Euphorbiaceae has enhanced diterpenoid and diterpene biosynthetic activity.

In an alternative preferred method of the invention said plant of the Euphorbiaceae has reduced or abrogated diterpenoid and diterpene biosynthetic activity.

According to a further aspect of the invention there is provided a plant of the Euphorbiaceae family obtained by the method according to the invention.

According to an aspect of the invention there is provided a plant of the Euphorbiaceae family wherein said plant comprises a viral vector that includes all or part of a gene comprising a nucleic acid molecule according to the invention.

In a preferred embodiment of the invention said gene or part is encoded by a nucleic acid molecule comprising a nucleic acid sequence selected from the group consisting of:

- i) a nucleic acid molecule comprising a nucleotide sequence as represented in 1, 2, 3, 4, 5, 6, 7,8, 9, 10, 11, 12, 13, 14, 15, 16,17, 18, 19, 20, 21, 22, 23, 24, 25 or 26;

ii) a nucleic acid molecule comprising a nucleotide sequence that hybridises under stringent hybridisation conditions to a nucleic acid molecule in (i) and which encodes a polypeptide with cytochrome P450 activity.

According to a further aspect of the invention there is provided a viral vector comprising all or part of a nucleic acid molecule according to the invention.

According to an aspect of the invention there is provided the use of a viral vector according to the invention in viral induced gene silencing in a plant of the Euphorbiaceae.

Virus induced gene silencing [VIGS] is known in the art and exploits a RNA mediated antiviral defence mechanism. Plants that are infected with an unmodified virus induce a mechanism that specifically targets the viral genome. However, viral vectors which are engineered to include nucleic acid molecules derived from host plant genes also induce specific inhibition of viral vector expression and additionally target host mRNA. This allows gene specific gene silencing without genetic modification of the plant genome and is essentially a non-transgenic modification.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by example only and with reference to the following figures:

FIG. 5 provides cDNA sequences that encode polypeptides with casbene-oxidase activity from *Ricinus communis* (SEQ ID NOS: 1_ and 2).

FIG. 6 provides cDNA sequences that encode polypeptides with casbene-oxidase activity from *Ricinus communis* (SEQ ID NOS: 3_ and 4).

FIG. 7 provides cDNA sequences that encode polypeptides with casbene-oxidase activity from *Euphorbia fischeriana* (SEQ ID NO: 5) and *Jatropha curcas* (SEQ ID NO: 6).

FIG. 8 provides a cDNA sequence that encodes a polypeptide with casbene-oxidase activity from *Jatropha gossypifolia* (SEQ ID NO: 7)_ and a cDNA sequence that encodes a polypeptide with casbene-5-oxidase activity from *Euphorbia peplus* (SEQ ID NO: 8).

FIG. 9 provides a cDNA sequence that encodes a polypeptide with neoembrene-5-oxidase activity from *Ricinus communis* (SEQ ID NO: 9)_ and a cDNA sequence that encodes a polypeptide with 5-keto-casbene 7,8-epoxidase activity from *Ricinus communis* (SEQ ID NO: 10).

FIG. 10 provides a cDNA sequence that encodes a polypeptide with cytochrome P450 activity from *Ricinus communis* (SEQ ID NO: 11)_ and a cDNA sequence that encodes a polypeptide with cytochrome P450 activity from *Ricinus communis* (SEQ ID NO: 12).

FIG. 11 provides cDNA sequences that encode polypeptides with cytochrome P450 activity from *Ricinus communis* (SEQ ID NOS: 13 and 14).

FIG. 12 provides cDNA sequences that encode polypeptides with cytochrome P450 activity from *Euphorbia peplus* (SEQ ID NOS: 15, 16 and 17).

FIG. 13 provides cDNA sequences that encode polypeptides with cytochrome P450 activity from *Jatropha curcas* (SEQ ID NOS: 18 and 19).

FIG. 14 provides cDNA sequences that encode polypeptides with cytochrome P450 activity from *Jatropha curcas* (SEQ ID NOS: 20, 21 and 22).

FIG. 15 provides cDNA sequences that encode polypeptides with cytochrome P450 activity from *Jatropha curcas* (SEQ ID NOS: 23 and 24).

FIG. 16 provides cDNA sequences that encode polypeptides with cytochrome P450 activity from *Jatropha curcas* (SEQ ID NOS: 25 and 26).

FIG. 17 provides protein sequences with casbene-5-oxidase activity from *Ricinus communis* (SEQ ID NO: 27), casbene-oxidase activity from *Ricinus communis* (SEQ ID NOS: 28 and 29), casbene-oxidase activity from *Euphorbia peplus* (SEQ ID NO: 30), or casbene-oxidase activity from *Euphorbia fischeriana* (SEQ ID NO: 31).

FIG. 18 provides protein sequences with casbene-5-oxidase activity from *Jatropha curcas* (SEQ ID NO: 32), casbene-oxidase activity from *Jatropha gossypifolia* (SEQ ID NO: 33), casbene-5-oxidase activity from *Euphorbia peplus* (SEQ ID NO: 34), neocembrene-5-oxidase activity from *Ricinus communis* (SEQ ID NO: 35), or 5-keto-casbene 7,8-epoxidase activity from *Ricinus communis* (SEQ ID NO: 36).

FIG. 19 provides protein sequences with cytochrome P450 activity from *Ricinus communis* (SEQ ID NOS: 37, 38, 39, and 40) and from *Euphorbia peplus* (SEQ ID NO: 41).

FIG. 20 provides protein sequences with cytochrome P450 activity from *Euphorbia peplus* (SEQ ID NOS: 42 and 43), and from *Jatropha curcas* (SEQ ID NOS: 44, 45 and 46).

FIG. 21 provides protein sequences with cytochrome P450 activity from *Jatropha curcas* (SEQ ID NOS: 47, 48, 49, and 50).

FIG. 22 provides a protein sequence with cytochrome P450 activity from *Jatropha curcas* (SEQ ID NO: 52).

TABLE 1

Primers used for cloning genes

Figures 1A, 1B, 1C, 1D, 1E:
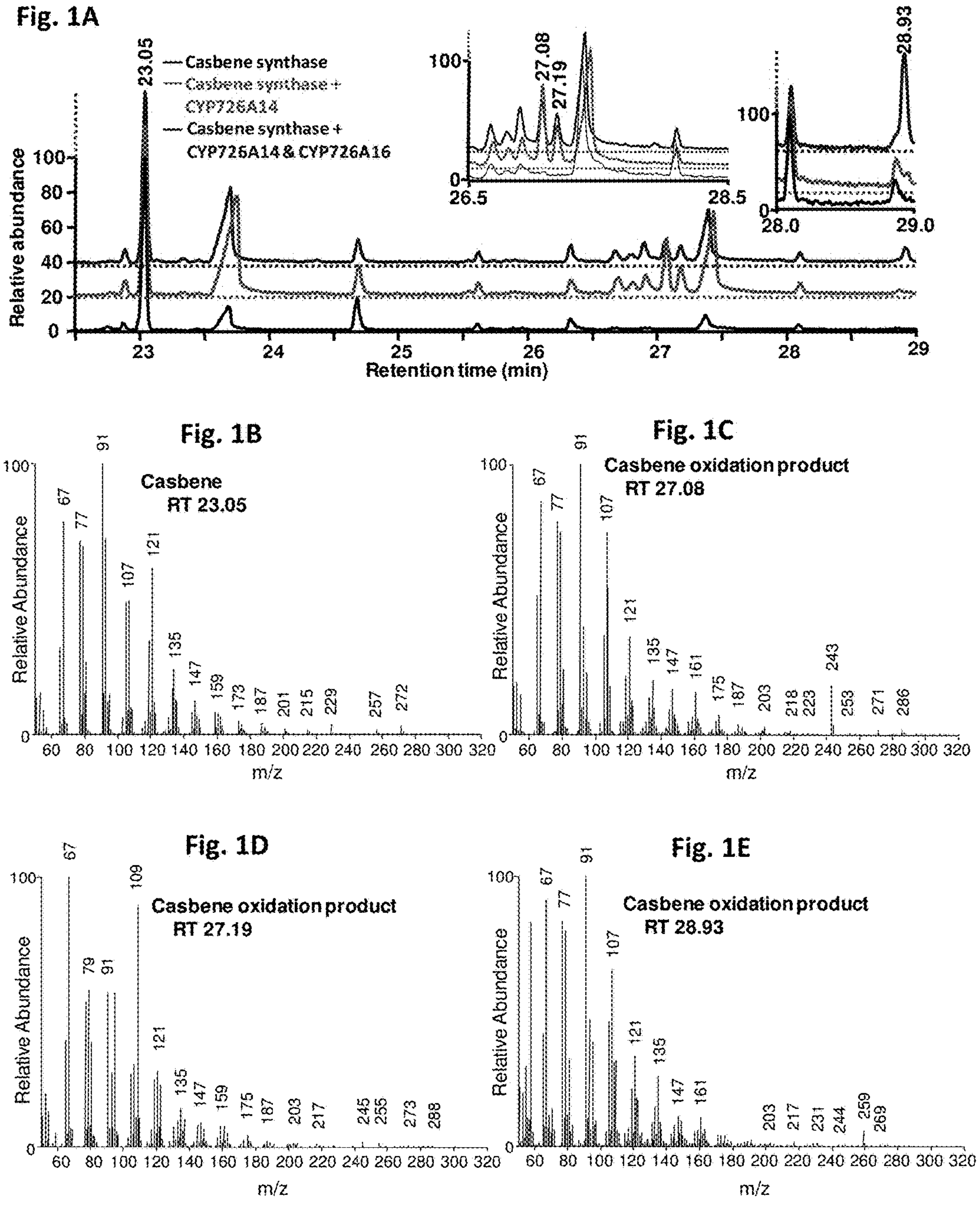
FIGS. 1A-1E: GC-MS analysis of N. benthamiana leaf extracts transiently expressing casbene synthase and cytochrome P450 enzymes. A-GC chromatograph obtained with expression of casbene synthase only (lower, black), casbene synthase and CYP726A14 (SEQ ID NO 2) (middle, red) and casbene synthase plus CYP726A14 (SEQ ID NO 2) and CYP726A16 (SEQ ID NO 10) (upper, blue). The two insets display rescaled chromatographs containing the retention times at which the casbene synthase oxidation products eluted from the column. B-E-Election impact mass spectra for casbene (B), casbene oxidation products produced by CYP726A14 (SEQ ID NO 2) (C & D) and the product obtained from co-expression of proteins encoded CYP726A14 (SEQ ID NO 2) and CYP726A16 (SEQ ID NO 10).

| Gene ID & annotation | Primer name | Species | Sequence (SEQ ID NO:) |
|---|---|---|---|
| Rc30169.m006273 (CYP726A13) (SEQ ID NO 11) | Rc6273F (ID 53)<br>Rc6275R (ID 54) | *R. communis*<br>*R. communis* | 5'-ATGGACAAGCAAATCCTATCATATCC-3' (53)<br>5'-TCAGTCCGTTGTTGGTGAAGGG-3' (54) |
| Rc30169.m006275 (CYP726A14) (SEQ ID NO 2) | Rc6275F (ID 55)<br>Rc6275R (ID 56) | *R. communis*<br>*R. communis* | 5'-ATGGAGCAGCAATTGCTATCG-3' (55)<br>5'-CTATGGCAAAGTAGTGAATGGAATGG (56) |
| Rc30169.m006276 (Neocembrene synthase) (SEQ ID NO 85) | Rc6276F (ID 57)<br>Rc6276R (ID 58) | *R. communis*<br>*R. communis* | 5'-ATGGCACTGCAATCACTACTATTC-3' (57)<br>5'-TTACACATGTTTTGTTTTGGTTTCTCC-3' (58) |
| Rc30169.m006277 (CYP726A15) (SEQ ID NO 9) | Rc6277F (ID 59)<br><br>Rc6277R (ID60) | *R. communis*<br>*R. communis* | 5'-ATGTCATTGCAACCTGCACCTG-3' (59)<br><br>5'-TTAAGGATGAAATAGAACAGGAATC-3' (60) |
| Rc30169.m006279 (CYP726A16) (SEQ ID NO 10) | Rc6279F (ID 61)<br>Rc6279R (ID 62) | *R. communis*<br>*R. communis* | 5'-ATGGAAAGTGCTGCTCACCAATC-3' (61)<br>5'-TTATGGTAAAGGACTGACGGGAATGG-3 (62) |
| Rc30169.m006282 (CYP726A17) (SEQ ID NO 3) | Rc6282F (ID 63)<br>Rc6282R (ID 64) | *R. communis*<br>*R. communis* | 5'-ATGGAGAAACAAATCCTATCATTTCCAG-3' (63)<br>5'-CTAAGGAGTAAATGGAATGGGAATC-3' (64) |
| Rc30169.m006285 (CYP726A18) (SEQ ID NO 1) | Rc6285F (ID 65)<br>Rc6285R (ID 66) | *R. communis*<br>*R. communis* | 5'-ATGTCATCACAACCAGCAGTTTTAC-3' (65)<br>5'-TCAATGTGTAGGATATAGAACAGG-3' (66) |
| JcCAS1 (Casbene synthase) (SEQ ID NO 86) | JcCAS1_F (ID 67)<br>JcCAS1_R (ID 68) | *J. curcas*<br>*J. curcas* | 5'-TTCATATTTGTTGCTAATCCTC-3' (67)<br>5'-CAAGGTACAGGATTTATGCAAATCC-3' (68) |

TABLE 2

Primers used for insertion of genes into pFGC5941

| Gene ID & annotation | Primer name | Species | Sequence |
|---|---|---|---|
| Rc30169.m006273 (CYP726A13) (SEQ ID NO 11) | Rc6273F_AscI (ID 69)<br>Rc6273R_PacI (ID 70) | *R. communis*<br>*R. communis* | 5'-AAAAGGCGCGCCAAAAATGGACAAGCAAATCCTATC-3' (69)<br>5'-AAAATTAATTAATCAGTCCGTTGTTGGTGAAG-3' (70) |
| Rc30169.m006275 (CYP726A14) (SEQ ID NO 2) | Rc6275F_AscI (ID 71)<br>Rc6275R PacI (ID 72) | *R. communis*<br>*R. communis* | 5'-AAAAGGCGCGCCAAAAATGGAGCAGCAATTGCTATCG-3' (71)<br>5'-AAAATTAATTAACTATGGCAAAGTAGTGAATG-3' (72) |
| Rc30169.m006276 (Neocembrene synthase) (SEQ ID NO 85) | Rc6276F_AscI (ID 73)<br>Rc6276R_PacI (ID 74) | *R. communis*<br>*R. communis* | 5'-AAAAGGCGCGCCAAAAATGGCACTGCAATCACTACTATTC-3' (73)<br>5'-AAAATTAATTAATTACACATGTTTTGITTIGGITTCTC-(74) |
| Rc30169.m006277 (CYP726A15) (SEQ ID NO 9) | Rc6277F_AscI (ID 75)<br>Rc6277R_PacI (ID 76) | *R. communis*<br>*R. communis* | 5'-AAAAGGCGCGCCAAAAATGTCATTGCAACCTGCACCTG-3' (75)<br>5'-AAAATTAATTAATTAAGGATGAAATAGAACAG-3' (76) |
| Rc30169.m006279 (CYP726A16) (SEQ ID NO 10) | Rc6279F_AscI (ID 77)<br>Rc6279R_PacI (ID 78) | *R. communis*<br>*R. communis* | 5'-AAAAGGCGCGCCAAAAATGGAAAGTGCTGCTCACCAATC-3' (77)<br>5'-AAAATTAATTAATTATGGTAAAGGACTGACG-3' (78) |

TABLE 2-continued

Primers used for insertion of genes into pFGC5941

| Gene ID & annotation | Primer name | Species | Sequence |
|---|---|---|---|
| Rc30169.m006282 (CYP726A17) | Rc6282F_AscI (ID 79) | *R. communis* | 5'-AAAAGGCGCGCCAAAAATGGAGAAACAAATCCTATCATTTC-3' (79) |
| (SEQ ID NO 3) | Rc6282R_PacI (ID 80) | *R. communis* | 5'-AAAATTAATTAACTAAGGAGTAAATGGAATG-3' (80) |
| Rc30169.m006285 (CYP726A18) | Rc6285F_AscI (ID 81) | *R. communis* | 5'-AAAAGGCGCGCCAAAAATGTCATCACAACCAGCAGTTTTAC-3' (81) |
| (SEQ ID NO 1) | Rc6285R_PacI (ID 82) | *R. communis* | 5'-AAAATTAATTAATCAATGTGTAGGATATAGAAC-3' (82) |
| JcCAS1 (Casbene | JcCAS1_AscI_F (ID 83) | *J. curcas* | 5'-AAAAGGCGCGCCAAAAATGGCAATGCAACCTGCAATTG-3' (83) |
| synthase) (SEQ ID NO 86) | JcCAS1_PacI_R (ID 84) | *J. curcas* | 5'-AAAATTAATTAATCAAGTGGCAATAGGTTCAATGAAC-3' (84) |

MATERIALS AND METHODS

Plant Materials, Nucleic Acid Extraction and Cloning of Cdna Sequences.

*Ricinus communis* (var. *Carmencita*) seeds were obtained from Thompson & Morgan (Ipswich, UK). *Jatropha curcas* seeds were obtained from Diligent (Tanzania). *Euphorbia peplus* seeds were obtained from All Rare Herbs (Mapleton, Old, Australia). Total RNA was extracted from plants using the CTAB-lithium chloride method (Gasic et al., 2004. Plant. Mol. Bio. Rep. 22:437a-437g). RNA samples were DNase treated and further purified using the on-column digestion protocol for the OlAgen RNeasy miniprep kit. cDNA was then synthesised from 5 μg of total RNA using Superscript II reverse transcriptase (Life Technologies, Carlsbad, Calif., USA) and a 5'-T(18)VN-3' oligonucleotides in a 20 μl volume according to the manufacturer's protocol. The cDNA product was then diluted to 50 μl with 10 mM Tris-HCl (pH 8.0). cDNA sequences were amplified with primers detailed in Table 1 using Phusion High-Fidelity Pfu DNA polymerase (Thermo Scientific, Waltham, Mass.) according to the manufacturer's recommended protocol and the subcloned in vector pJET 1.2 (Thermo Scientific). The cDNA sequences were the verified by dye-terminator sequencing.

Expression of Diterpenoid Biosynthetic Genes in *Nicotiana benthamiana*

Ascl and Pacl sites were added at the 5' and 3' end of the ORF by PCR using Phusion High Fidelity Pfu polymerase using the primers detailed a Table 2. For each ORF, a 5-AAAA-3' Kozak sequence was included immediately before each start codon. After restriction digestion, the ORF was then inserted into the 10 kb fragment obtained from digestion of pFGC5941 (Kerschen et al., 2004. FEBS Lett. 566: 223-228) with restriction enzymes Ascl and Pacl. The expression vectors were then transformed into *Agrobacterium tumefaciens* GV3101::pMP90 using the freeze-thaw method (Hofgen & Willmitzer 1988. Nucleic Acids. Res. 16: 9877). Infiltration of *N. benthamiana* plants was performed as described previously using an enhanced system which utilizes the p19 protein of tomato bushy stunt virus to reduce the effects of post-transcriptional gene silencing (Voinnet et al., 2003. Plant J. 33: 949-956).

Extraction of Terpenoids from *N. benthamiana* Leaves and GC-MS Analysis

Five days after Agrobacterium infiltration, three leaves were collected from each plant, ground in liquid nitrogen and then extracted with 10 ml of chloroform. The extracts were concentrated to <500 μl under a stream of nitrogen, and then 5 μl of the extract was analysed GC-MS. GC-MS analysis was performed using Thermofinnigan GCQ coupled to a Polaris MS and AS2000 autosampler. The GC was fitted with a Restek (Bellafonte, Pa., USA) RTX-5SIL MS capillary column (30 m, 0.25 mm ID, 0.25 μM df). The oven temperature was set at 100° C. for 2 minutes and then increased to 300° C. at a rate of 5° C. min-1. Mass spectral data was acquired for the m/z ranges of 50-450.

Purification of the Casbene and Two Oxidation Products Produced by CYP726A14 (SEQ ID NO 2)

100 g of *Agrobacterium* infiltrated *N. benthamiana* leaves were dried by lyophilisation and then extracted twice with 200 ml of 60/40 hexane/isopropanol. The extract was dried over anhydrous sodium sulphate and the solvent was then removed by rotary evaporation to yield 520 mg of a green oily residue. This extract was dissolved in 10 ml of hexane fractionated by flash chromatography using 25 grams of silica gel 60 (particle size 35-70 μM, 220-440 mesh) as a stationary phase. The mobile phases were (a) 250 ml of hexane, (b) 250 ml of 2% ethyl acetate in hexane, (c) 250 ml 10% ethyl acetate in hexane and (d) 50% ethyl acetate in hexane. Fractions of 25 ml were collected and an aliquot from each was analysed for the presence of casbene or casbene oxidation products by GC-MS (as above). Fractions containing the desired compounds were pooled then concentrated via rotary evaporation. The casbene fraction did not require further purification, but the two casbene oxidation products were further purified using reverse phased HPLC. The fractions were evaporated to dryness and then dissolved in 250 μl of methanol. 10 μl aliquots were separated on a Develosil C30-UG-S column (3 mm ID, 5 μM particle size, Nomura Chemical Co. Ltd, Seto, Japan) using a three solvent gradient. Solvent A was 20 mM ammonium formate, 0.2% formic acid and 20% water in methanol. Solvent B was 0.2% formic acid in methanol. Solvent C was 0.2% formic acid in tetrahydrofuran. The gradient was ran as follows; at injection, 80% Solvent A and 20% solvent B ramping via a linear gradient to 40% solvent A and 60% solvent B over 16 minutes. After holding at this ratio for a further 1 minute, the solvents were switched to 40% solvent B and 60% solvent C for a further 8 minutes. The flow rate was 1 ml minute-1. Detection was performed using atmospheric pressure chemical ionization (+ve). The fractions were then pooled, evaporated to dryness in a GeneVac EZ-2 plus (Ipswich, UK) and dissolved in 500 μl of $CDCl_3$.

NMR Analysis of Casbene and Casbene Oxidation Products

All NMR data were recorded with a Bruker AVIII 700 MHz instrument, equipped with a TCI probe. 2D-NMR datasets were typically acquired with 2,048 points in F2 and 256 increments in F1 then Fourier transformed to give a spectral resolution of 4,096×1,024 data points.

EXAMPLE 1

Modification of Casbene by CYP726A14 (SEQ ID NO 2), CYP726A17(SEQ ID NO 3) and CYP726A18 (SEQ ID NO 1) from *R. communis*

Figure 2:
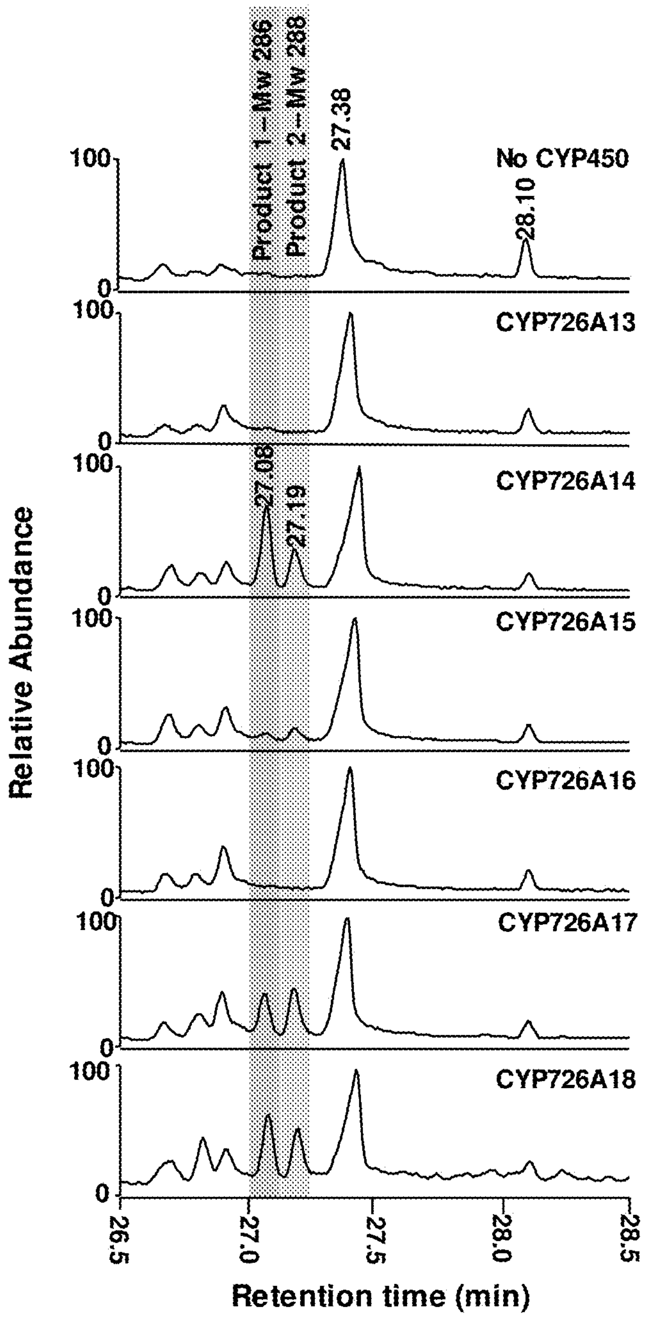
FIG. 2: GC analysis of a chloroform extract of *N. benthamiana* leaves infiltrated with a p19 vector, a pFGC vector containing a casbene synthase ORF for *J. curcas* and pFGC vectors contain the ORF for a cytochrome P450 gene as indicated in the top right of each graph.

To determine whether any of the *R. communis* P450 genes were capable of modifying casbene, we used a transient expression system in *Nicotiana benthamiana*. A casbene synthase gene from *J. curcas* and each of the P450 genes were co-expressed via infiltration of young *N. benthamiana* plants by multiple combinations of *Agrobacterium tumefaciens* strains harbouring different expression vectors. Five days after infection, chloroform extracts of the leaves were analysed by GC-MS. Three of the P450 genes (CYP726A14 (SEQ ID NO 2), CYP726A17 (SEQ ID NO 3) and CYP726A18 (SEQ ID NO 1)) were able to use casbene as a substrate (FIG. 1 and FIG. 2).

EXAMPLE 2

Modification of Neocembrene by CYP726A15 (SEQ ID NO 9) from *R. communis*

Figure 3:
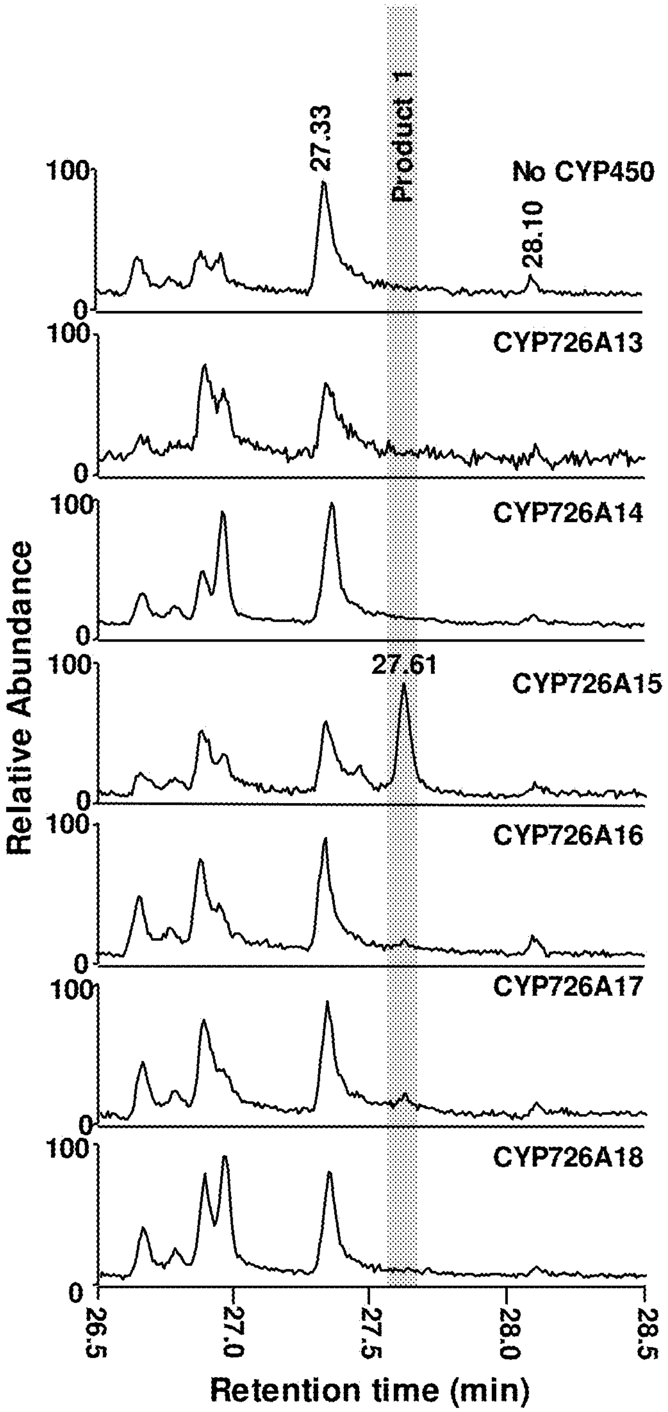
FIG. 3: GC analysis of a chloroform extract of *N. benthamiana* leaves infiltrated with a p19 vector, a pFGC vector containing the neocembrene synthase ORF for *J. curcas* and pFGC vectors contain the ORF for a cytochrome P450 gene as indicated in the top right of each graph.

To determine whether any of the *R. communis* P450 genes were capable of modifying casbene, we used a transient expression system in *Nicotiana benthamiana*. A neocembrene synthase gene from *R. communis* and each of the P450 genes were co-expressed via infiltration of young *N. benthamiana* plants by multiple combinations of *Agrobacterium tumefaciens* strains harbouring different expression vectors. Five days after infection, chloroform extracts of the leaves were analysed by GC-MS. CYP726A15 (SEQ ID NO 9), was able to use neocembrene as a substrate (FIG. 3).

EXAMPLE 3

Figure 4:
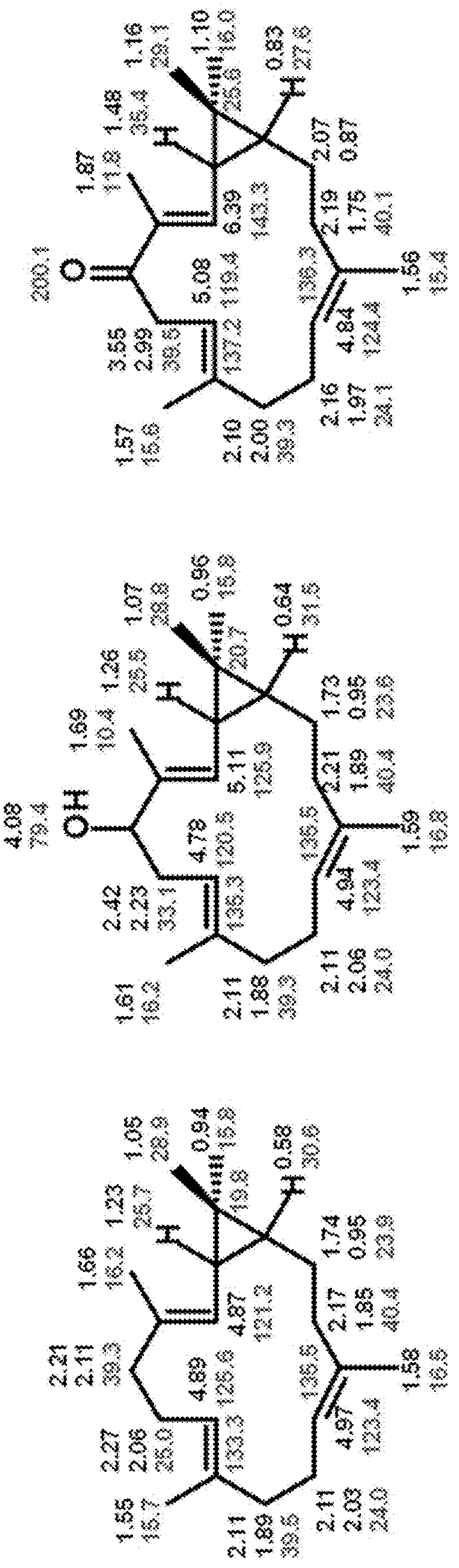
FIG. 4: Structures of casbene (left), 5-hydroxycasbene (centre) and 5-ketocasbene (right) as established by 1D- and 2D-NMR. $^{1}H$ and $^{13}C$ assignments at each position are shown in black and red, respectively.

NMR Analysis of the Products of CYP726A14 (SEQ ID NO 2) Reveals it is a Casbene 5-oxidase To obtain structures of the two products of CYP726A14 (SEQ ID NO 2) (and therefore CYP726A17 (SEQ ID NO 3) and CYP726A18 (SEQ ID NO 1)), lyophilized material from 100 g of infiltrated leaf material was extracted. The two casbene oxidation products were purified using a combination of normal-phase flash chromatography and preparative reversed-phase HPLC to yield approximately 300 μg of casbene, 30 μg of 5-hydroxycasbene and 15 μg of 5-ketocasbene. All three samples were dissolved separately in CDCl3 (500 μl) and NMR data was recorded at 700 MHz. Following acquisition of both 1D-$^{1}$H and $^{13}$C NMR spectra, the 2D-experiment, edited-HSQC, was used to determine which protons and carbons were directly attached to one another via a single bond. Both HMBC and $^{1}$H-$^{1}$H COSY experiments were then used to connect these fragments of the molecule together through the observation, respectively, of 2- and 3-bond couplings between proton and carbon; and (predominantly) 3-bond couplings between protons. The $^{1}$H and $^{13}$C assignments resulting from these experiments are shown at each position on the structures appearing in FIG. 4. The perturbations to both 1H and 13C chemical shifts at and around the 5-position of the two oxygenated derivatives of casbene support the two functionalizations which are proposed.

EXAMPLE 4

Modification of 5-ketocasbene by CYP726A16 from *R. communis*

To determine whether any of the *R. communis* P450 genes were capable of modifying 5-hydroxy- or 5-ketocasbene, we used a transient expression system in *Nicotiana benthamiana*. A casbene synthase gene from *J. curcas*, CYP726A16 (SEQ ID NO 10) from *R. communis* and each of the other *R. communis* P450 genes were co-expressed via infiltration of young *N. benthamiana* plants by multiple combinations of *Agrobacterium tumefaciens* strains harbouring different expression vectors. Five days after infection, chloroform extracts of the leaves were analysed by GC-MS. An additional product was observed when CYP726A16 was co-expressed, and the relative levels of 5-ketocasbene were decreased (retention time 27.08 minutes in FIG. 1). CYP726A16 (SEQ ID NO 10) was therefore identified as a 5-ketocasbene oxidase.

The invention claimed is:

1. A transgenic fungal cell comprising an expression vector adapted to express a nucleic acid molecule, wherein the nucleic acid molecule comprises:

i) the nucleotide sequence of SEQ ID NO: 6;

ii) a nucleotide sequence comprising at least 90% identity to SEQ ID NO: 6 and that encodes a polypeptide having cytochrome P450 activity; or iii) a nucleotide sequence degenerate as a result of the genetic code to the nucleotide sequence of SEQ ID NO: 6 and encodes a polypeptide comprising SEQ ID NO: 32 and that has cytochrome P450 activity;

or wherein the nucleic acid molecule comprises:

iv) the nucleotide sequence of SEQ ID NO: 18;

v) a nucleotide sequence comprising at least 90% identity to SEQ ID NO: 18 and that encodes a polypeptide having cytochrome P450 activity; or vi) a nucleotide sequence degenerate as a result of the genetic code to the nucleotide sequence of SEQ ID NO: 18 and encodes the polypeptide of SEQ ID NO: 44 and that has cytochrome P450 activity.

2. A process for modification of one or more diterpenoids or diterpenes, the process comprising:

i) cultivating the transgenic fungal cell of claim 1; and optionally ii) isolating said one or more diterpenoid or diterpene from the transgenic fungus or fungal culture.

3. The transgenic fungal cell of claim 1, wherein said fungal cell is a *Saccharomyces cerevisiae* cell.

4. A process for modification of one or more diterpenes or diterpenoids, the process comprising:

i) cultivating the transgenic *Saccharomyces cerevisiae* cell of claim 3 under conditions that modify one or more diterpenes or diterpenoids; and optionally ii) isolating said one or more diterpenoid or diterpene from the transgenic *Saccharomyces cerevisiae* cell or cell culture.

5. The transgenic fungal cell of claim 1, wherein the fungal cell is transformed or transfected with an expression vector adapted to express the nucleic acid molecule of SEQ ID NO: 6.

6. The transgenic fungal cell according to claim 1, wherein the fungal cell is transformed or transfected with an expression vector adapted to express the nucleic acid molecule of SEQ ID NO: 18.

7. The transgenic fungal cell of claim 1, wherein the fungal cell is transformed or transfected with an expression vector adapted to express the nucleotide sequence degenerate as a result of the genetic code to the nucleotide sequence of SEQ ID NO: 6 and encodes the amino acid sequence of SEQ ID NO: 32.

8. The transgenic fungal cell of claim 1, wherein the fungal cell is transformed or transfected with an expression vector adapted to express the nucleotide sequence degenerate as a result of the genetic code to the nucleotide sequence of SEQ ID NO: 18 and encodes the amino acid sequence of SEQ ID NO: 44.

9. The transgenic fungal cell of claim 1, wherein the nucleic acid molecule expressed by the expression vector is over-expressed when compared to a non-transgenic fungal cell of the same species.

* * * * *

SEQUENCE LISTING

```
<160> NUMBER OF SEQ ID NOS: 86

<210> SEQ ID NO 1
<211> LENGTH: 1602
<212> TYPE: DNA
<213> ORGANISM: Ricinus communis

<400> SEQUENCE: 1

atgtcatcac aaccagcagt tttacaatcc aacttcctta acagaaacgt ccagccattt      60

ctaaccattc cctctgcttc taccaagtat agtggcaccg cttgtttctc ttcctttccc     120

tcagttaaat taaatgctag accaccgcaa gcatgcttct ccttgaataa aaacaacgat     180

cactctaccc ccacctccat ccttcctcca ggaccttggc agttacctct gataggtaac     240

atacaccagc tcgtcggcca tttaccccat agccgcctga gagacttggg aaaaatttat     300

ggacctgtga tgagtgttca actcggagaa gtttctgctg tggtggtatc atcagtagaa     360
```

```
gcagccaaag aagtgctgag gatccaggat gtcatcttcg ctgaaagacc tcctgtcctc    420
atggcagaaa ttgtgctcta caatcgtcat gatattgttt ttgggtctta tggagatcac    480
tggagacaac ttagaaagat ttgcacattg gagttgctta gtcttaagcg cgtgcaatct    540
ttcaaatcag tcagggaaga cgagttttca aattttatca aatacctttc ttccaaagcc    600
ggaactccag tcaatcttac tcacgacttg ttttctttaa caaattctgt tatgttaaga    660
acctccatag gcaagaaatg caaaaaccaa gaagcaattt taagaatcat cgacagtgtt    720
gttgcggcag gaggaggttt cagtgttgct gatgtgtttc cttccttcaa attgctccat    780
atgattagcg gagacaggtc aagtcttgag gccttacgtc gagacacaga cgagatactt    840
gacgaaatca ttaatgaaca caaagccggc aggaaggctg gtgatgatca cgacgaagct    900
gaaaatcttc tggatgttct tttggatctt caggaaaatg gagacctgga agtcccttta    960
accaacgaca gcatcaaagc aacaattctg gatatgtttg ggctggtag cgacacgtcc   1020
tcaaaaacag cagaatgggc gttgtcggag ttgatgagac acccagaaat aatgaaaaag   1080
gcacaggagg aagtgagggg agtctttggt gatagcggag aagtcgatga aacacgcctt   1140
catgaattaa aatacttgaa gttagtgatc aaagaaacat tgagattaca tcctgccatt   1200
ccattaattc caagagaatg cagggaaagg actaagatta atggatatga cgtatatccc   1260
aaaaccaagg tccttgtcaa tatttgggca atctcaagag atccaaatat atggagcgaa   1320
gcagataaat tcaaaccaga aagattcttg aacagttcac ttgattacaa gggtaattat   1380
ctggaattcg ctccgtttgg ttctgggaaa agggtatgtc ctggtatgac attaggtata   1440
actaatctag agctcatcct tgcaaaatta ctatatcatt ttgactggaa acttcctgat   1500
ggaataacgc ctgagacgct tgacatgact gaatctgttg gtggcgcaat taaaagaaga   1560
acagacctta acttgattcc tgttctatat cctacacatt ga                      1602
```

```
<210> SEQ ID NO 2
<211> LENGTH: 1506
<212> TYPE: DNA
<213> ORGANISM: Ricinus communis

<400> SEQUENCE: 2
```

```
atggagcagc aattgctatc gtttccagcc cttttgagct ttctcctttt aatcttcgtg     60
gtactaagga tctggaagca atacacatac aaaggaaaat ccacccccacc ccctggacca    120
tggagattac ctctcctagg caactttcac cagctagttg gtgctctacc ccaccaccgc    180
ctaaccgaat tggccaaaat ttatggacca gttatgggta ttcaacttgg tcagatttct    240
gttgtcatca tttcctcagt agaaacagcc aaagaagtgc ttaaaaccca gggtgagcag    300
ttcgctgata gaaccccttgt cctcgcagca aaaatggtac tttataatcg caacgacatt    360
gtgtttggat tatacggaga ccactggaga caactgagaa aattatgcac attggagctg    420
cttagtgcaa aacgtgtcca atcattcaag tccgtcagag aagaagagct ctcaaatttt    480
gtaaagttcc ttcattccaa agcaggaatg cccgtcaatc ttactcacac gttgtttgct    540
ttgacaaaca atattatggc aagaacatct gtaggtaaaa aatgcaagaa ccaggaagcc    600
ctcttaagta ttatagatgg catcattgat gcatcaggag gttttactat tgcggatgtg    660
tttccttccg ttcccttcct ccacaacata tctaatatga aatcgagatt ggagaagttg    720
catcaacaag cggacgatat tcttgaagac atcataaatg aacacagagc caccaggaat    780
cgtgatgatc tggaagaagc tgaaaatctc cttgatgttc ttttggatct tcaggaaaat    840
```

```
ggaaaccttg aagtcccttt gaccaatgac agcatcaagg gagccattct ggatatgttt    900

ggagctggta gcgacacatc ctcaaaaaca gccgaatggg cattgtcgga gttgatgagg    960

cacccagaag aaatgaaaaa ggcacaagaa gaggtgaggc gaatttttgg tgaagatgga   1020

agaattgatg aagctcgatt tcaagaattg aagttcttga atttagttat caaagaaact   1080

ctgagattac atcctccagt agcactgatt ccaagagaat gtagggaaaa aactaaggtt   1140

aatggatacg atatctatcc taaaactaga acactcatta atgtttggtc tatgggaagg   1200

gatcccagtg tttggactga agctgagaag ttctacccgg aaaggtttct ggatggcaca   1260

attgattata gaggtactaa ttttgaacta attccatttg gtgcaggaaa aaggatatgt   1320

cctggtatga cattagggat agttaacctt gagcttttcc ttgcgcacct attgtatcat   1380

tttgactgga agcttgttga tggagtggct cctgacactc ttgacatgag tgaaggtttt   1440

ggcggtgcac ttaaaaggaa aatggacctt aacttggttc ccattccatt cactactttg   1500

ccatag                                                              1506
```

<210> SEQ ID NO 3
<211> LENGTH: 1494
<212> TYPE: DNA
<213> ORGANISM: Ricinus communis

<400> SEQUENCE: 3

```
atggagaaac aaatcctatc atttccagtc ttattaagct ttgtcctttt tatcttaatg     60

atcttaagga tatggaagaa aagcaaccca cctccaggac catggaaatt acctctgtta    120

ggcaacattc accagctggc tggtggtgct ctgccccatc accgcctaag ggacttggca    180

aaaacttatg gaccagttat gagtattcaa ctcggccaga tttctgctgt cgtaatttct    240

tcagtacaag gagccaaaga agtgctgaag actcagggtg aggtgttcgc tgaaagaccc    300

ctcatcatcg cagctaaaat tgtgctttat aatcgtaagg atattgtatt tggttcctac    360

ggagatcact ggagacaaat gagaaagatc tgcaccttag agctactgag tgccaaacgc    420

gtccagtcct ttagatccgt cagggaagaa gaggtctcag aatttgtgag atttcttcaa    480

tccaaagcag gaacgccagt caatcttacc aagaccctgt ttgctttaac aaattctatc    540

atggcaagaa catccatagg taaaaaatgt gaaaaacaag aaacgttttc aagtgttata    600

gacggtgtca ctgaggtatc aggaggtttt actgttgctg atgtgtttcc ttctttggga    660

ttccttcacg tcatcactgg tatgaagtct agactagaga ggttgcaccg agtagcagat    720

cagatatttg aagatataat agctgaacac aaagccacca gggcactctc caagaacgat    780

gatccgaaag aagcagctaa tcttctagat gttcttttgg atcttcagga acacggaaat    840

cttcaggtcc ctttaaccaa cgacagcatc aaagcagcca ttctggaaat gtttggtgct    900

gggagcgaca catcctcaaa aaccacagaa tgggccatgt cagagttgat gaggaaccca    960

acagaaatga gaaaagcaca agaagaagtg aggcgagtgt ttggtgaaac agggaaggtt   1020

gatgaaacac gccttcatga attaaagttt ttgaagttgg ttgtcaaaga aactytgaga   1080

ttacatcctg ccatagcatt aattccaaga gaatgcaggg agaggactaa ggttgacggg   1140

tatgacataa aacccacagc tagagtcctc gtcaatgtat gggcgattgg aagggatcct   1200

aatgtttgga gtgaacctga aaggtttcac ccagaaaggt ttgtcaatag ttcagttgat   1260

ttcaagggta ctgatttcga actacttcca tttggtgcag gaaagagaat atgccctggt   1320

attttagtgg gtataactaa tttagagctt gttttagctc acctattata tcattttgat   1380

tggaaatttg ttgatggagt gacgagtgat agttttgata tgagagaagg ttttggtggg   1440
```

-continued gcacttcata gaaaatcaga ccttatcttg attcccattc catttactcc ttag 1494

<210> SEQ ID NO 4
<211> LENGTH: 1683
<212> TYPE: DNA
<213> ORGANISM: Euphorbia peplus

<400> SEQUENCE: 4
atggcaacac ttcaacattc aatgcaagca aatttacaga aacaaaatct tcatccattg 60
ttaaacaaat cctttggtac tccgaatcgt ccttccttcg tctattcctc gaaatctgca 120
tcccgaagaa caatccaagc atgtttatct tcaaattcac agcctggagg agtttgcccc 180
atggctaatc gctttgcttc ctcaactact aatcaatctg ttactgagtc cagttcaaaa 240
ccagatgaag aggatgaaaa ttctccggtt aaacttcctc cgggaccgtg gaaattacct 300
ttgctcggta atattctcca gctcgttgga gacctaccgc atagtcgcct acgagattta 360
gcgacagaat acggacctgt tatgagtgtt caactcggtg aagtttacgc tgtggtaatt 420
tcatctgttg aagcagctag agaaattctc agaaatcagg atgtaaattt tgctgataga 480
ccgccggtct tagtatccga aattgttctt tacaatcgtc aggatatcgt tttcggtgcc 540
tacggagttc attggcgaca aatgagaaga ctatgcacga cggaattgct tagtataaaa 600
cgtgttcagt cattcaaatt agtccgtgaa gaagaggttt cgaatttcat caaatcgctt 660
tactcgaaag caggaaagcc cgttaatctt accgagggtt tgttcacgtt gacgaattcg 720
ataatgttga ggacgtcgat cggtaagaaa tgcagggatc aagatacact tttgagagta 780
attgaaggag ttgtggcggc cggaggaggt tttagcatcg cggatgtgtt tccttctgcc 840
gtgttccttc acgatatcaa tggagacaag tcgggcctcc agagtttgcg gcgagatgct 900
gatttgatac tcgacgagat cattggtgaa catagagcta ttagaggtac tggtggggat 960
caaggtgaag ctgataatct tttagatgtt cttctggatc ttcaggaaaa tggaaatctt 1020
gaagtccctt tgaatgatga tagcatcaaa ggggcaattc tggacatgtt tggggcagga 1080
agtgacacct catcaaaatc aacagaatgg gcgttatcag aattactacg acacccagaa 1140
gaaatgaaaa aagcacaaga cgaagtaaga cgagtttttg caaagaaagg aaatgtagaa 1200
gaatcacaac ttgaccaatt aaaatacctg aaattagtca tcaaagaaac tctgagacta 1260
cacccagcag tccctttaat cccaagagaa tgcagagaaa aaaccaaggt caatggatat 1320
gatattctcc caaaaactaa ggcacttgtg aatatttggg caatctctag ggaccccaaa 1380
atttggcctg aagcagataa atttatacct gaaagattcg aaaatagttc aattgatttt 1440
aagggaaata acttggaatt cgctccgttt ggttcaggaa aaagaatatg tccaggcatg 1500
gccttgggga taactaattt ggagcttttt ctggcacaac ttttgtatca tttcgattgg 1560
aaacttgccg acgggaaaga cggtagggat cttgacatgg gtgaagttgt tggtggtgct 1620
attaaaagaa aagtagacct caatttgatt cctattccat tccatacttc acctgcaaac 1680
tga 1683

<210> SEQ ID NO 5
<211> LENGTH: 1677
<212> TYPE: DNA
<213> ORGANISM: Euphorbia fischeriana

<400> SEQUENCE: 5
atgtcaacac ttcaaccttt tctgcaagca aattttcaga agcaaaattc tcatccattg 60

-continued

```
ttaagcaaac ctttaggtac taccaatcat ccttccttca tttcttcgtc taaatcaaca    120

aaaagatcaa ctattcaagc atgtttatct tcaaattcgc agcctggtgg agtttgcccc    180

atggctaatc gctttgcttc ttcttcaact actaatcaat ctgttactca gtccagttca    240

aacccagatg aaaaggacgg aaattcacag gttcagcttc ctccggggcc gtggaaatta    300

cctttcatcg gtaatattct ccagctcgtc ggagatctac cccatcgtcg cctaagagat    360

ttggcgacag tgtacggacc tgttatgagt gttcaacttg gggaagttta cgctgtgata    420

atttcatcag ttgaagcagc taaagaagtt ctcagaacac aggatgtgaa tttcgctgat    480

agaccgcccg tcctagtatc cgaaatcgtt ctctacaatc gtcaggatat cgtatttggt    540

tcctacggag atcattggcg acagatgaga agaatctgca caatggaatt gcttagtata    600

aaacgtgttc aatcattcaa atctgtccgg gaagaagagg tttcgaattt tatcaaattg    660

ctttattcgg aagcaggaca gccggtcaat cttacggaga agttgtttgc tttgacgaat    720

tcgattatgt tgaggacttc aattggtaag aaatgcaaag atcaagagac ccttttgaga    780

gtaattgaag gagttgtggc ggccggagga ggtttcagtg ttgctgatgt gtttccttcc    840

gccgtgttcc ttcatgatat caccggagac aagtctggcc ttgagagttt gcgccgagat    900

gcagatttgg tacttgatga gatcatcgga gaacatagag ctaatagatc aggtaatggt    960

ggtgatgaag gcgaagctga aaatcttttg gatgttcttt tggatcttca ggaaaatgga   1020

aatcttgaag tccctttaaa cgatgacagc atcaaagcta caattctgga tatgtttggg   1080

gcaggaagtg acacatcctc caaatctaca gaatgggcat tatcagagtt actaagacac   1140

ccagtagcaa tgaagaaagc acaagatgaa gtaaggaaag ttttcagtga aaatggaaat   1200

gtagaagaag aaggacttaa ccaattaaaa tacttgaaat tagtcatcaa ggaaactctc   1260

agattacacc cagcaatccc tttaattcca agagaatgca gagaaaagac taaagtcaat   1320

ggatatgaca ttcttccaaa aactaaggca cttgtgaata tttgggcaat ttccagagat   1380

ccaacaatat ggccagaagc agacaaattc atcccagaaa gatttgaaaa tagttcaatg   1440

gatttcaaag gaaatcactg tgaatttgct ccatttggtt caggaaaaag gatatgccca   1500

ggcatggctt tggggataac taatcttgaa cttttccttg cacaactgtt atatcatttt   1560

gactggaaac ttaccgacgg aaaagaccct cgaaatcttg acatgagtga agtagtaggt   1620

ggtgcaatta aaagaaaaat agatctcaat ttgattccta ttccattcca tccttaa      1677
```

```
<210> SEQ ID NO 6
<211> LENGTH: 1890
<212> TYPE: DNA
<213> ORGANISM: Jatropha curcas

<400> SEQUENCE: 6

atgtcgctgc aaccagcaat tttacaggga aatacctgta aacagtattt tcatccatta     60

tcaagcatat cctctaccag atgggttggc aattgcaacc gtttcgcttt tctttctccg    120

gctaagccaa ctgcaaacag agcaccgcaa gcgtctttat catcaaaact gcagccagta    180

gttcgtctgc tgactaaatt ccctgcttct ggtttcttgg ccatgaatca atctgttgat    240

caatttgctt caactaccac aagtcttacc aaaatattca acaaaatagg aaaacctatc    300

caatcatctc catttcttgt aagcgttctt cttttgatgt ttatggcatc aaaaatacag    360

aaccaacaag aagaagatga taactccata aatcttcctc caggaccatg gagattacct    420

ttcataggta acattcacca acttgctggc cccggtctac cccatcaccg tctaacagac    480

ttagccaaaa cttacggacc tgtaatgggt gttcaccttg gcgaagttta cgctgttgtt    540
```

```
gtttcctccg cagaaacatc caaagaagta ttaagaacgc aggatacaaa tttcgctgaa    600
agacctttag ttaatgcagc gaaaatggtc ctatataaca gaaacgacat tgtttttggg    660
tcgtttggag atcaatggcg acaaatgaga aaaatctgca cattagaatt acttagtgta    720
aaacgtgtgc agtcattcaa atcagtaaga gaagaagaga tgtcaagttt tattaaattt    780
ctttcttcga aatctggttc gccggtaaat cttacccatc atctgtttgt tttgacaaac    840
tatattattg caagaacttc cattggtaag aaatgtaaga atcaagaagc gcttcttaga    900
attatagacg acgtcgttga ggcgggagct ggatttagtg ttactgatgt ctttccatcg    960
tttgaagcgc ttcatgtgat tagtggagat aagcataaat ttgataaatt gcatagagaa   1020
actgataaga tacttgaaga tatcataagt gaacataaag ccgacagggc agtatcttcc   1080
aagaaaagtg atggtgaagt tgagaatctt cttgatgttc ttttggatct tcaagaaaat   1140
ggaaaccttc aatttccctt aacaaatgat gccatcaaag gagccattct ggatacattt   1200
ggcgcaggca gcgacacatc ctcaaaaaca gcagaatgga cattatcgga gctgatcagg   1260
aacccagaag caatgagaaa agcacaagca gaaataagga gagttttcga tgaaacagga   1320
tatgttgatg aagacaaatt tgaggaatta aaatacctga aactagttgt gaaggaaact   1380
ttgagattac atcctgctgt gccattaatt ccaagagaat gcagaggaaa aactaagatt   1440
aatgggtatg acattttccc caagaccaag gtattggtga acgtctgggc aatttcaaga   1500
gatcctgcaa tttggccaga gcctgaaaag ttcaatccag aaagattcat cgataatccg   1560
attgattata agagtattaa ctgcgagcta acaccttttg gtgcgggaaa gagaatttgc   1620
cctggaatga cattagggat aacaaatctt gaactttttcc tggcaaattt gctatatcat   1680
tttgattgga aacttcctga cgggaagatg ccagaggatc ttgatatgag tgaatcattt   1740
ggtggagcaa ttaaaagaaa aacagatctg aagttgattc ctgttctggc gcgccctttg   1800
actccaagaa acgccaacag tggcaacact ttcactacaa cagacgccga ctctcctgca   1860
tcaatgtgcc cacacttaaa agcattatga                                    1890
```

<210> SEQ ID NO 7
<211> LENGTH: 1890
<212> TYPE: DNA
<213> ORGANISM: Jatropha gossypifolia

<400> SEQUENCE: 7

```
atgtcactgc aaccagcagt tttacaggca aatacctgta aacagtattt tcatccatta     60
tcaagcatat cctctaccag atgggttggc aattgcaacc gtttcgcttt cctttctccg    120
gctaagccaa ctgctaacag agcaccgcaa gcttctttat catcaaaact gcagccagta    180
gttcgtctgc tgactagatt ccctgcttct ggtttcttgg ctatgaatca atctgtcaat    240
caatttgctt caactacaac aagtcttgcc aaaatattcg acaaaatagg aaaacctatc    300
caatcatctc catttcttct aagtgttctt cttttgatgt ttatggcatc aaaaatacag    360
aaccaacaag aagaagataa taactccata aatcttcctc caggaccatg gagattacct    420
ttcataggta acattcacca acttgctggc cccggtctac cccatcaccg tctaacagac    480
ttggccaaaa cttatggacc tgtaatgggt gttcaccttg gcgaagttta cgctgttgtt    540
gtttcctccg cagaaacatc taaagaagta ttaagaacac aggatacaaa tttcgctgaa    600
agacctttgg ttaatgcagc gaaaatggtc ctatataaca gaaacgacat tgtttttggg    660
tcgtatggag atcaatggcg acaaatgaga aaaatctgca cattggaatt acttagttta    720
```

-continued

```
aaacgtgtgc agtcattcaa atcagtaaga gaagaagaga tgtcaagttt tattaaattt    780
ctttgttcga aatctggttc gccggtaaat cttacccatc atctgtttgt tttgacaaac    840
tatattattg caagaacttc cattggtaag aaatgtaaga atcaagaagc gcttcttaga    900
gttatagacg acgtcgttga ggcaggagct ggatttagtg ttactgatgt ctttccatcg    960
tttgaagccc ttcatgtgat tagtggagat aagcataaat ttgataaatt gcatagagaa   1020
actgataaga tacttgaaga tatcataagt gaacataagg ccgacagggc agtatcttcc   1080
aagaaaagtg atggtgaagc tgagaatctt cttgatgttc ttttggatct tcaagaaaat   1140
ggaaatcttc aatttccctt aacaaatgat gccatcaaag gagccattct ggatacgttt   1200
ggcgcaggca gcgacacatc ctcaaaaaca gcagaatgga cgttatcaga gttgatcagg   1260
aacccaggag caatgagaaa agcacaagaa gaaataagga gagttttcga tgaaacagga   1320
tatgttgatg aagacaaatt tgaggaatta aaatacctga aactagttgt gaaggaaact   1380
ttgagattac atcctgctgt gccattaatt ccaagagaat gcagaggaaa aactaagatt   1440
aatgggtatg acattttccc caagactaag gtcttggtga acgtctgggc aatttcaaga   1500
gatcctgcaa tttggccaga gcctgaaaag ttcaatccag aaagattcat cgataatccg   1560
attgattata agagtattaa ttgcgagcta acaccttttg gtgcaggaaa gagagtttgc   1620
cctggaatga cattagggat aacaaatctt gaacttttcc tggcaaattt gctatatcat   1680
tttgattgga aacttcctga cggaaagatg ccagaagatc ttgatatgag tgaatcattt   1740
ggtggagcaa ttaaaagaaa aacagatctg aagttgattc ctgttctggc tcgtcctttc   1800
aatccaacta acgccaacaa tggcaacact ttcactacaa cagacgccaa ctctccttca   1860
tcaatgtgcc cacacttaaa agcattatga                                    1890
```

<210> SEQ ID NO 8
<211> LENGTH: 1503
<212> TYPE: DNA
<213> ORGANISM: Euphorbia peplus

<400> SEQUENCE: 8

```
atggagcttc aatttcaaat cccctcttat ccagtccttt tctccttctt catcttcatc     60
tttatactaa tcaaaatagt aaaaaaacaa actcaaaact ctatctcccc tccgggacca    120
tggaaatatc ctattttggg aaacattcca caattagctg ccggcggaaa gcttcctcat    180
caccggttaa gagatttagc aaaaatccat ggtccggtga tgaacattca actcgggcaa    240
gtcaagtcca ttgtcatttc ctccccggaa actgccaaag aggtgttgaa aactcaggat    300
atccagttcg ccaataggcc tcttcttctc gctggagaaa tggttcttta caaccggaaa    360
gatatcttgt acggtcttta cggggatcaa tggcgacaaa tgaggaaaat atgcactttg    420
gagttactaa gtgctaagcg aattcaatca ttcaagtcag tgagagaaca agaagtcgag    480
agcttcattc ggttgctccg atcaaaggcg gggtccccag tgaatctcac gacagcggtg    540
tttgagttga cgaatactat tatgatgatc acgacgattg gtgagaaatg caagaatcaa    600
gaggcggtga tgagtgtgat tgatcgagtg agtgaggctg cagcggggtt tagtgttgcc    660
gacgtatttc catcgctaaa atttcttcat tatctgagtg gagaaaaggg gaagttgcag    720
aagttgcata aggagactga tgagatactt gaagagatta taagtgaaca taaagctaat    780
gctaagattg gaagccaagc tgataatctt ttggatgttt tgttggatct tcagaaaaat    840
gggaatcttc aagttccatt gactaatgat aatatcaaag ctgccactct ggaaatgttc    900
ggagctggta gcgacacatc ctccaaaact acagactggg caatggcgca actaatgagg    960
```

aagccatcag caatgaaaaa ggcacaagaa gaggtcaggc gcgtctttag cgacacggga 1020
aaggtagagg aatcaagaat ccaagaacta aaatacttga aattaatcgt taaagaaaca 1080
ttgagattac atcctgccgt ggcattgatt cctagagaat gccgagagaa aactaaaatc 1140
gagggatttg atgtttatcc taaaacaaaa attcttgtga atccttgggc gattggaaga 1200
gatccgaaag tttggagtga ccccgaaagt ttcaacccag aaagatttga agatagttca 1260
atagactata agggtacaaa tttcgaacta attccgtttg gtgcaggaaa aagaatatgt 1320
ccaggaatga ctttgggcat agtgaattta gagcttttcc ttgcaaattt gttatatcat 1380
tttgattgga aattcccaaa tggagtcaca gctgagaatc ttgatatgac tgaagccatt 1440
ggtggtgcta tcaagagaaa actagacctt gagttgattc ctattccata cacattaagt 1500
taa 1503

<210> SEQ ID NO 9
<211> LENGTH: 1605
<212> TYPE: DNA
<213> ORGANISM: Ricinus communis

<400> SEQUENCE: 9
atgtcattgc aacctgcacc tgtttcacaa tccaactttc tttacaaaaa agttccacca 60
atattacgtg cacccactac caagtctagt ggtagcagtc gttcctcttt cttttcctca 120
tcagttaagt tagctgctag accaccgcaa ccgcaagctt gcttatcgtt gaacaaaaac 180
gatgactcca atacctccgc ctccagtctt cctccaggac catggaagtt gcctctgcta 240
ggtaacattc accagctagt cggagctctt ccccatcacc gcctaagaga cttggctaaa 300
gcttacgggc ctgtcatgtc tgttaaactc ggagaagttt ctgctgtcgt aatttcatca 360
gtagatgctg ccaaagaggt actcaggact caggatgtca acttcgcaga tagacccctt 420
gtcctggcag cagaaattgt gctatataat cgtcaggaca ttgtatttgg gtcatatgga 480
gagcaatgga gacaaatgag aaagatttgc acactggagt tgcttagtat taagcgcgtt 540
caatctttca aatcggtcag ggaagaagag ctttctaatt ttatcagata ccttcactca 600
aaagctggaa ctcctgttaa ccttactcat cacttgtttt ctttaacaaa ttccattatg 660
tttagaattt ccattggtaa gaaatacaaa aatcaagatg cacttttgag agtcatcgat 720
ggcgtcattg aagctggagg aggtttcagt actgctgatg tgtttccttc ctttaaattc 780
cttcaccaca ttagcggaga gaagtctagc cttgaggact tgcaccgaga agcagactat 840
atactagaag atatcataaa tgaacgcaga gcctccaaga ttaatggtga tgatcgaaac 900
caagctgata atctcttaga tgttctttta gatcttcagg aaaacggaaa tctcgaaatc 960
gctctaacca atgacagcat caaagcagcc attctggaaa tgtttggtgc tggcagcgac 1020
acatcctcaa aaaccgctga atgggcactg tcagagttga tgaggcaccc agaagaaatg 1080
gaaaaggcac aaacagaagt aaggcaagtc tttggtaaag atggaaattt ggatgaaact 1140
cgacttcatg aattaaaatt cttgaagtta gttatcaaag aaaccttaag attgcatcct 1200
ccagtagcat tgattccaag agaatgcagg caaaggacta aggttaatgg atatgacata 1260
gatcccaaaa ctaaggttct cgtcaatgtt tgggcaattt caagggatcc aaatatatgg 1320
actgaagcag agaaattcta cccggaaaga tttcttcaca gttccattga ttacaagggc 1380
aatcattgtg aatttgctcc atttggatct ggaaaaagaa tatgccctgg tatgaactta 1440
ggtttaacta atcttgaact cttccttgcc caattactgt atcactttaa ctgggaattt 1500

-continued

```
cctgatggaa taacacctaa gactcttgat atgacagaat ctgttggtgc tgcaattaaa   1560

agaaagatag atcttaaatt gattcctgtt ctatttcatc cttaa                   1605
```

<210> SEQ ID NO 10
<211> LENGTH: 1572
<212> TYPE: DNA
<213> ORGANISM: Ricinus communis

<400> SEQUENCE: 10

```
atggaaagtg ctgctcacca atcctacttc catatgttcc tggctatgga gcagcaaatc     60

ctttcatttc cagtcctttt aagctttctt cttttcattt tcatggtatt aaaggtgtgg    120

aagaaaaaca aggacaatcc aaactcgcct ccggggccaa ggaagttgcc tatcataggc    180

aacatgcacc agctagctgg tagtgatctg ccccatcacc ctgtaacaga attgtcaaaa    240

acttacggac caataatgag cattcaactt ggccaaatat cggccatcgt tatttcttca    300

gtagaaggag ccaaagaagt gctgaagacc caaggtgagc tgttcgctga aagacctctt    360

ctcttggcag cagaggcagt gctttataat cgtatggaca ttatattcgg tgcatacggt    420

gatcattgga ggcaattgag aaaattgtgc accttagagg tgcttagtgc aaaacgaatc    480

caatcattca gttcactcag acaagaagaa ctttcacatt ttgtccgctt cgttcattcc    540

aaagcaggaa gcccaatcaa tctttccaag gtgctgtttg ctttaacaaa ttctatcatt    600

gcaagaatcg ccacaggtaa gaaatgcaaa aaccaagatg ccctcttaga tcttatcgaa    660

gacgttattg aggtatctgg aggtttcagc attgccgatt tatttccttc gttgaaattc    720

attcacgtca tcactggtat gaagtctaga ctggaaaaat tgcatcggat aacagatcag    780

gtacttgaag acatcgtcaa tgaacataaa gccaccaggg cagcctccaa gaatggtggt    840

ggtgacgatg ataaaaaaga agccaaaaat cttctagatg ttcttttgga tcttcaagaa    900

gatggaagcc ttcttcaagt tcctttaacc gacgatagca tcaaagcagc cattctggaa    960

atgcttggcg gtggaagtga cacatctgca aaaaccacag aatgggcaat gtccgagatg   1020

atgaggtacc cagaaacaat gaaaaaagca caagaagaag tgaggcaagc gttcggtaac   1080

gcgggaaaga ttgatgaagc acgcatccat gagttgaaat acttgagggc agttttcaaa   1140

gagactttga gattacatcc cccgctagcg atgataccga gagaatgcag gcaaaagact   1200

aagattaatg gatatgatat ctatcccaaa actaaaacgt tgatcaatgt atatgcaatc   1260

ggaagggatc ccaatgtttg gagtgaacct gagaagttct atccggaaag acatcttgat   1320

agtccaatcg acttcagagg cagtaacttt gaactaattc cattcggtgc agggaaaaga   1380

atatgtcctg gcatgacatt agctataact actgtggagc tgtttctcgc tcatcttcta   1440

tactattttg actggaagtt tgttgatgga atgacggctg atactcttga tatgactgaa   1500

tccttcggag cttcaattaa aagaaaaata gatctcgccc tggttcccat tcccgtcagt   1560

cctttaccat aa                                                       1572
```

<210> SEQ ID NO 11
<211> LENGTH: 1521
<212> TYPE: DNA
<213> ORGANISM: Ricinus communis

<400> SEQUENCE: 11

```
atggacaagc aaatcctatc atatccagtg ctcctgctga gcttcctcct ttttatctta     60

atggtgttaa ggatatggaa gaaaagcaag ggcagcttca actcacctcc gggaccatgg    120

aagttacctc tcataggcaa catgcaccaa ctcattactc ctctgcccca tcaccgcctg    180
```

```
agagaattgg ccaaaactca tgggccagtt atgagtattc aacttggcca agtttcggcc    240

gtcgtcattt cctcagtaga agcagctaag caagtgctca aaacccaagg tgaattgttc    300

gctgaaagac ccagcatcct ggcatcaaaa atagtgcttt ataatggtat ggacataata    360

tttgggtcat acggtgacca ctggagacaa atgaggaaaa tttgcacctt cgagctgctc    420

agtccaaaac gcgtccagtc cttcagttcg gtcaggcaag aagaactttc caattatgtc    480

aggttcctcc attccaatgc cggaagccca gtcaatctgt ccaagacctt gtttgcttta    540

acaaattctg ttatcgcaaa aatcgcagta ggtaaggaat gcaaaaacca ggaagccctc    600

ttaaatctta tcgaagaagt ccttgtggca gcaggaggtt tcactgttgc tgattcattt    660

ccatcctata atttccttca cgtcatcact ggtatgaagt ctaacctgga gagattgcac    720

cggataacag ataagatcct tgaagacatc ataactgaac ataaagcccc cagggcactc    780

ttcaagcgtg gtggcgatga ggataaaaaa gaagccgaaa atcttttaga tgttcttttg    840

ggtcttcagg aacatggaaa ccttaaagtc cctttaacca atgagagtgt caagtcagcc    900

attctggaaa tgctttccgg cgggagcgac acatctgcaa aaacaataga atgggcaatg    960

tcagagttga tgaggagtcc agaagcaatg gaaaaggcac aagaagaagt gagaagagtg   1020

tttggtgaat tgggaaagat cgaggaatca cgcctccatg aattaaagta cttgaaatta   1080

gttatcaaag agacgttgag attacatccc gcactagcct tgattccaag agaatgcatg   1140

aaaagaacta agattgatgg atatgatatt tctcccaaaa ctaaagcctt ggtcaatgta   1200

tgggcaatcg gaagagatcc cagcgtttgg aatgaacctg aaaagttttt cccggaaagg   1260

tttgtcgaca gttcgattga tttcagaggt aataattttg aactacttcc atttggttca   1320

ggaaagagga tatgtcctgg tatgacattg ggtttagcca ctgtagagct tttcctctcc   1380

tacctgctgt attattttga ttggaagctt gtcggtggag tgcctcttga catgaccgaa   1440

gcttttgctg cttcacttaa aagaaaaata gacctcgttt taattcccat ttcagtcggc   1500

ccttcaccaa caacggactg a                                             1521
```

<210> SEQ ID NO 12
<211> LENGTH: 1503
<212> TYPE: DNA
<213> ORGANISM: Ricinus communis

<400> SEQUENCE: 12

```
atggagctgc aaatcttttc ttttccagtt cttctgagct tcttcctttt tattttcatg     60

gtcttgagga tatggaagaa ttccaacaaa aaattgaacc cccctccagg accctggaag    120

ctacctcttc taggaaatat tcatcaacta gccaccccat taccccatca acgcctcaga    180

gatttggcca aaagttttgg cccagtgatg agcatcaaac ttggggaaat ttcagctgtg    240

ataatttcat cagcagaagc agctcaagaa gtactaaaat ctcaggatgt cacctttgct    300

gaaaggcctg catctcttgc ttcgaaatta gtactttaca atcgcaacga tattgtcttt    360

ggggcttatg gaccacaatg gagacaaacg agaaaactgt gcgtgctgga gctgctaagt    420

gccaaacgca ttcaatcatt caaatctgta agggaagaag aggtagacga gtttgccaag    480

ttcgtttatt cgaaaggtgg gacgccagtc aaccttactg ataagctgtt tgctttaaca    540

aatactatca tggcaaggac caccataggt aagaaatgca gaagtgaaaa agatctcttg    600

agatgtattg atggcatctt tgaagaagca ggggttttca atcttgccga tgcgtttcct    660

tcctttactt tgcttcctgt aatcactgga gccaagttta gacttgagaa attgcataga    720
```

-continued

```
gagacagaca agatacttga agacatctta cgtgaacaca tagcttccaa ggctgcttca    780

gacaaagata cccggaatct tttacatgtt cttttggatc ttcaggaaag tggaaacctt    840

gaagtcccta ttaccaacga cagcatcaaa gctactattc tggatatatt tatcgcaggg    900

agcgacacat ctgcaaaaac tgtagagtgg gcaatgtcag agttgatgcg aaacccaaaa    960

ttaatgaaaa gagcacaaga agaagtgagg caagtctttg gtgagaaggg gtttgttgat   1020

gaagcagggc ttcaggattt aaaattcatg aagttgattg ttaaagaaac tttgagattg   1080

catcctgtct ttgcaatgtt tccaagagaa tgtagggaaa agacaaaagt caatggatat   1140

gacatttctc ctaagactac aatgctcatc aatgtgtggg caattggaag ggatcctaat   1200

gtctggcctg atgcagagaa gttcaaccca gaaagatttc ttgatagttc aattgattac   1260

aaaggtaata atgctgaaat gattccattt ggtgcaggaa aaaggatatg tcttgggatg   1320

acattaggta cacttattct agagcatttc cttgcaaaac tactctatca ttttgattgg   1380

aaatttcctg atggagtaac ccctgagaat ttcgacatga cagaacatta tagtgcttcg   1440

atgagaaggg aaaccgacct tatcttaatt cctattccag tccatccttt gcctacacac   1500

taa                                                                 1503
```

<210> SEQ ID NO 13
<211> LENGTH: 1503
<212> TYPE: DNA
<213> ORGANISM: Ricinus communis

<400> SEQUENCE: 13

```
atggagcagc agatcctctc attttctgtc ctttcatgtc tcattctttt tctcttaatg     60

gtcattaata ttttgaaaaa ttacagtaaa gattttaccc ctcctccagg accatggaag    120

ctaccctttc ttggtaatat tcaccagcta gctaccgcac tacctcatcg tcgcctacga    180

gatttggcca aaacttatgg tcctgtaatg agcattaagc ttggagaaat ttcttctatc    240

gtaatctcat cagcagaagc agctcaagaa gtactgaaaa ctcaggatgt catatttgca    300

gaaagaccaa tagctcttgc agccaaaatg gtgctttaca atcgtgatgg cattgtcttt    360

ggttcctatg gcgagcaact caggcagtca aggaaaattt gcatattgga gctgttaagt    420

gcgaaacgca ttcagtcatt caaatcagta agggaagaag aggtatctaa ctttatcagt    480

ttccttaatt cgaaagcggg gacgcctgtc aaccttactg acaagctgtt tgcattaact    540

aattctatca tggcaagaac ctcaattggt aagaaatgca agaatcaaga agatctctta    600

agatgtattg ataacatttt tgaggaagca acagttttca gccctgccga tgcgtttcct    660

tcctttactt tgcttcatgt aatcaccgga gtcaagtcta gacttgagag attgcatcaa    720

caaacagaca agatacttga agacattgta agtgaacaca aagctactat ggctgctacc    780

gagaatggag accggaatct cttgcatgtt cttttggatc ttcagaaaaa tggaaatctt    840

caagttcctt taaccaacaa catcatcaaa gcaattattc tgactatatt tatcggaggg    900

agtgacacat cggcaaaaac tgtagaatgg gtaatgtcag agttgatgca taaccctgaa    960

ctgatgaaaa aagcacaaga agaagtgagg caagtctttg gtgaaaaggg atttgttgat   1020

gaaacagggc tgcatgaatt aaaatttctc aagtcagttg ttaaggagac tctgaggttg   1080

catcctgttt tcccattagt tcctagagag tgtagggaag taactaaggt gaatggatac   1140

gacatttatc ctaaaactaa ggtgctcatc aacgtgtggg ctattggaag ggatcctgat   1200

atctggtccg acgcagaaaa gttcaatcct gaaagatttc ttgaaagttc gattgactac   1260

aaagatactt cttctgaaat gatcccattt ggtgcaggaa agagggtatg tcctggcatg   1320
```

tcattaggcc tactaattct tgagcttttt cttgcacagc tactctatca ttttgactgg 1380
aaacttcctg atagagttac tccggagaat tttgacatga gcgaatatta tagttcttca 1440
ttgagaagaa aacatgacct tatcttgatt cccattcctg tccttccttt gcctatagaa 1500
taa 1503

<210> SEQ ID NO 14
<211> LENGTH: 1515
<212> TYPE: DNA
<213> ORGANISM: Ricinus communis

<400> SEQUENCE: 14
atggagcagc aaattctctc atttccagtc cttctaagct tcttcctttt tatcttcatg 60
gtcttgaaaa tacggaagaa atacaacaag aatatcagcc ctcctccagg accatggaag 120
ctacctatcc taggtaacat tcaccagcta attagcccac taccccatca tcgcctaaga 180
gacttggcca aaatttatgg gcctgtgatg agtattaaac ttggcgaggt ttctgctgtg 240
gtaatttctt ccgcggaagc agcaaaagaa gtactaagaa cccaggatgt cagtttcgct 300
gatagacccc ttggcctctc agcgaaaatg gtgctttata atggtaacga tgttgttttt 360
ggttcttatg gagaacaatg gagacaactg agaaaaattt gcatattgga gctgcttagt 420
gcaaaacgtg ttcagtcttt caaatcgtta agggaagcag aggtatcaaa ttttattcgt 480
tttctttatt cgaaagcagg gaagcctgtc aaccttactc gcaagctgtt tgctttaaca 540
aatactatta tggcgagaac ctccgtaggt aaacaatgtg aaaatcaaga agttctctta 600
acagttatag ataggatttt tgaagtatca ggaggtttca ctgttgctga tgtttttcct 660
tcatttactt tgcttcattt aattactggg atcaagtctc gacttgagag gttgcatcaa 720
gacacagatc agattcttga agacatcata aatgagcata gagcttgtaa ggccgtatcc 780
aagaatggtg atcagaatga agctgacaat cttttagatg ttcttttgga tcttcaggaa 840
gatggaaacc ttcgagtccc tttaaccaat gacagcatca aaggaacaat tctggatatg 900
ttcgctggtg ggagtgatac aacttcaaaa actgcagaat gggcagtgtc agaattgatg 960
ttcaacccaa aagcaatgaa aaaagcacaa gaagaagtga ggcgagtctt tggccaaaaa 1020
gggattgttg atgaatcagg atttcatgaa ttgaaattct tgaagctggt tattaaagaa 1080
actctgagat tgcatccagc attgccctta attccaagag agtgtatgaa caagtctaag 1140
atcaatggat acaacattga tccaaaaacc aaggttctga tcaatgtgtg ggcaattgga 1200
agagattcta atatctggcc tgaagcagag aaattctatc cagaaagatt tctggatagt 1260
tcaatagatt ataagggcac tagttatgag ttcattccat ttggtgcagg aaagaggata 1320
tgtcctggca tgatgttggg tacaactaat cttgagcttt ttcttgccca actactatat 1380
cattttgact ggcaattccc tgatggagtg acacctgaga cttttgacat gacagaggct 1440
tttagcggtt caattaacag aaaatatgat cttaatttaa ttcccattcc gttccatccc 1500
ttgcgtgtag aatag 1515

<210> SEQ ID NO 15
<211> LENGTH: 1485
<212> TYPE: DNA
<213> ORGANISM: Euphorbia peplus

<400> SEQUENCE: 15
atggatcttg aaatgccctc ttttctcatc ctctttagct ttctcatttt aacatggatc 60

```
atatggaaga agatgaattc caactcagtt cctcctccgg ggccttggaa gttgcctctt    120
ctaggcaaca ttcttcaatt acgcggcggt ccagccaatc accgcctctg cgatttggct    180
aaagtgtacg gtccggtgat gagcattcaa ctaggccaga atcctgcggt tgtgctttct    240
tcacctgaag cagccgaaca agtcttcaaa attcagggcg acctatttaa caaccgtcca    300
ccagccctct caggtaaaat tttgttttac aataacagcg acatgacatt cacgccatac    360
ggagatcatt ggcgacaaat tagaaaaatt accgtgatgg aattccttag tccgaaacga    420
gttttatcgt ttcgatcaat acgtgaagaa caagtatcaa atttcatcaa attccttcgt    480
acgaaaggcg gatctgcgat caatttcccg aaagccctct ccgagttgac aagtaggatt    540
atgctaataa ccttacttgg taacaaagat gaaaatgagg aaattgtatt accagcgata    600
gaaagagtga tagagactgc aaataaaggt gctgcttcgg atacctttcc gacgttaaaa    660
ttcttcctcg actttctcac cggagacaag tcaagaatgg aaaaagtgtt acaagagacg    720
gatatcatac ttgaagccat cataaatgaa cacaaaaaaa aaggtacctc agaacacaat    780
tatttagatt ttctgctgga taaacagaaa aagggagacc tccaattgcc attaacaaac    840
gaagccatca aagcaaatct tatggctatg tatgcgggcg ggagtgagac atcatctaaa    900
ctcatagaat ggacattcgc ggagatgatg aagaaccctg aaacgatgcg aaaagcgcaa    960
gaggaggtga gaagagtttt tggtgacaaa ggaaaagttg aggaatcaag aattcaagaa   1020
ttgaaatact tgaaattagt tcttaaagaa tctttcagaa tacatcctcc gtcgaccttg   1080
attacaagag tatgccaaga aagaacaaaa atcaacggtt acgacattca tcccaaaact   1140
acaattctta tcaatgtgtg gacgatggga agagatccga atctttggaa agaacccgaa   1200
aagttccatc cagaaagatt tgaagatagt aaaattgatt tcagaggagc aaatatggaa   1260
ttaacaccat ttggtgtagg aaaaagaatg tgtcctggaa ttactctatc tacaacttat   1320
gtggagtttc tgctggcaaa tttattgtat cattttgatt ggaaacttcc tgacggagtc   1380
acaccggcca ctctcgatat gactgaaact ctgcgtggca cgctcaaaaa agtacaagat   1440
cttattttga ttcccattcc attctccccc catcaaattg cttga                    1485
```

<210> SEQ ID NO 16
<211> LENGTH: 1512
<212> TYPE: DNA
<213> ORGANISM: Euphorbia peplus

<400> SEQUENCE: 16

```
atggagttca ctttatcact taaaaaaatg gagcttcaaa tcctatcttt tccaatcctc     60
ttccccttc  tccttttcat ccttaccttc ctcacaatta tacgccggaa aaagcagaat    120
caagactgca attttcctcc gggaccatgg cagtttccga tcatcggaaa cattccacag    180
ttgctcggag gtctcttcca ccaccgtctt tccgatctag ccaaaattca cggcccgata    240
atgagcattc aacaaggaca aatcccagct gttgtaatca cttcagttga actagccaaa    300
gaagttctca aaacccaagg tgaaatattc gccggaaggc ctcaagcccc ggccggagat    360
gttttgtatt acgattgcaa ggatatcgtg ttcgccccgt acggggatca ctggagacag    420
atgagaaaga tctgcacact ggagtttctc agtctgaaaa gagttcagtc tttcagatcc    480
ttgagggaag aaaacgtttc aggttttatt aaattcctca gtactaaagc aaattcgtcg    540
gtaaatctga cgaaatccgt cggtaatttg acaagttcaa ttatgcttat taaaacttat    600
ggaaaatgtg atgaaaaatt gttggctatg ttggagaaag tgaaacaagc agttttagag    660
acgagtagtg gtacggatct gtttccgtcg ctgaaattta ttcaatatat taatggtgag    720
```

-continued

```
aagtcaagaa tggcaagggt gcaaaaggaa atggataaaa tgcttgaaca gattattaaa    780
gaacataaag ttcaatataa gtttggagat aataatcttt tgcaggtttt gttggatcaa    840
cagcaaaatg gagatcttga acttccattg acaaatgaaa tcatcaaagc caacattatg    900
gaaatatttt ttggtggaag ccatacttct tctaaaactg tggagtgggc aatgtcggag    960
ctaatgaaga acccagaatc aatgacaaaa gcacaagcag aggtgagaca agtcttcggt   1020
gagacgggaa atgttgagga atcaagaatg caagaagtga aatacctcaa gtcagttatc   1080
aaagaaactc taagattgca ccctccggcg acctttgtca caagagaatg cagacaaaaa   1140
acaaaagtca atggttatga tatttacccg aagacagttg ttcatgtcaa tacatatgca   1200
atctgtagag atcctgatgt ttgggttgaa cctgaaaagt tttatcctga aaggtttgaa   1260
gaaaatcaaa tagattataa gggtgcacat atggaactaa taccgtttgg tgcagggaaa   1320
agaatatgtc caggaatctc attagccaca acatacgttg aggttctcct tgcaaacttg   1380
ttatatcatt ttgactggaa acttccatat ggaatgactc ctgccaatct tgacatgacg   1440
gaaatgcatt gcggtgccct ggctagaaaa catgaccttt gcttgattcc aattccgttt   1500
tctaaaattt ga                                                       1512
```

<210> SEQ ID NO 17
<211> LENGTH: 1494
<212> TYPE: DNA
<213> ORGANISM: Euphorbia peplus

<400> SEQUENCE: 17

```
atgaaaatgc ttgagcaaat tccctctctt ccaatcatct ttcccttgat cctcttcatt     60
ttcatgctca taaagttatg gcagaaaaaa aatcacaact caatccgtcc acccggtcca    120
agaaaatatc cattcatagg caatcttcct caattacttg gtgctccagt tcatcaaaga    180
ctagcagatt tagccaaaac ctacggcccg gtaatgagca ttcaacaagg ccagatcccg    240
tccgtcgtgc tttcatcagt cgaaacggcc aaagaagtcc tcaaaatcca gggcgaagag    300
tttgctggaa gaccctccac tatggctctt gatataactt tttacgacgc ccaagatatt    360
gcctatactg aatacggtga ttattggaga caaatgaaga aaatttcgac gctagagttt    420
ctaagcgcga aacgagttca ttctttcaaa ccagtccggg aagaacgaat ttcgatattc    480
ctcgattccc ttcgttcaaa aggcagatct ccggtgaacc tgacgaggac aatttacggg    540
ttaacgaatt cgatcattca aataacggcg tttgggaaga actgtaaaac gagagagaaa    600
ttgaatcttg ataagattcg agaggcagtt gtggatggaa ctattgctga tttgtttccg    660
agatttaaat ttattgcgag tttgagtgga gctaaatcaa gaatgatgag ggctcataag    720
gagattgatg tggttcttga tgaaatcttg gaagaacata aggctaataa aagcaccatt    780
ggaaataatc ttatgcaagt tcttttggat tttcagaaaa atggtggcct tcaagttcca    840
ttgacaactg atcagattaa agctaacatg ctggaaatgt ttctttcagg gagccatacg    900
tcgtcaaaaa ttacagagtg gacaatggcg gagctaatgc gagcaccaga aacaatgaga    960
aaagcacaag aagaggtgag gcgagtcttc agcgaaattg gaagagtcga cgaatcaaga   1020
atccatgaat gtaaatacgt gaaaaatgtc cttaaggaag cttttagatt acatcctccg   1080
gggccaatgg ttgtaaggca atgcagagaa ataactaaag tcaatggtta cgagattctt   1140
cctggcacta cagttttcat caatgtctgg gcaataggaa gagatccgga ggtttggact   1200
gaacccgaaa agttcaaccc tgacagattc gaagacagtg aaattgatta cagaggcgca   1260
```

```
catatggaac taataccatt tggtgcaggg aaaaggatat gccctggctt gacgttagcc   1320

gtagtttacg ttgagctttt gcttgccaac ttattatatc atttcgattg ggaatttcca   1380

gatggagtca cacaaaagac tcttgatatg accgaatttt tccgtggtac actcaaccga   1440

aaagaagacc tttacttgat tcccgttcca tcttcttcat tgccaaagaa ttaa         1494


<210> SEQ ID NO 18
<211> LENGTH: 1512
<212> TYPE: DNA
<213> ORGANISM: Jatropha curcas

<400> SEQUENCE: 18

atggaacacc aaatcctctc atttccagtt cttttcagtt tgcttctttt tattctcgtc     60

ttactaaaag tatccaagaa attatacaaa catgactcta aacctccgcc tggaccatgg    120

aaattacctt tcataggtaa ccttatccag ctcgtcggtg acacacctca tcgccggtta    180

acagccttgg ccaaaactta cggacctgta atgggtgttc aacttgggca agttcctttc    240

cttgtcgtgt cctcgccgga aacagctaaa gaagtaatga aaatacaaga tcccgttttt    300

gcagaacgac cgcttgtcct tgcaggagaa atagtgcttt ataaccgaaa tgacatcgtt    360

tttgggtcgt acggagatca gtggaggcaa atgagaaaat tttgcacgtt ggaattactt    420

agcacaaaac gagtacagtc gttccgaccc gtgagagaag aagaagttgc atcttttgta    480

aaacttatgc gtacaaagaa aggaactcct gttaatctta ctcatgcttt atttgcttta    540

acaaattcta tagttgcaag aaatgctgtt ggtcataaaa gcaaaaacca agaggcgttg    600

ttagaagtta ttgatgacat agttgtatca ggaggaggtg ttagtatagt tgatatcttt    660

ccttccctac aatggcttcc tactgccaag agggaaagat caagaatttg gaaattgcac    720

caaaatacag atgagattct cgaagatatc ttacaagagc atagagctaa aagacaggcg    780

acagcttcca agaattggga taggagcgaa gctgataatc ttcttgatgt tcttttggat    840

cttcaacaga gcggaaatct tgatgttcct ttaactgatg tcgccatcaa agcagcaatt    900

attgatatgt ttggtgctgg aagcgacaca tcctcaaaaa ctgcagaatg ggcaatggct    960

gagttgatga ggaatccaga agtaatgaag aaagcacaag aagaattgcg gaatttcttt   1020

ggtgaaaatg gaaaggttga ggaagcaaaa cttcacgaat taaaatggat aaagttaatt   1080

attaaagaaa cattgagatt acatcctgca gtggctgtaa ttccaagggt ttgtagggaa   1140

aagactaaag tttatggata tgacgttgag cctggcactc gggttttcat taacgtgtgg   1200

tcaatcggaa gagatcctaa agtttggagt gaagctgaga gattcaagcc ggagagattt   1260

attgatagcg caattgatta caggggtctt aattttgaac tgattccatt tggagcagga   1320

aaaagaatat gccctggaat gaccttagga atggctaatc tggagatttt ccttgcaaac   1380

ttgctatatc attttgactg gaaatttcct aaaggagtaa ctgcagaaaa tcttgacatg   1440

aatgaagctt ttggaggagc tgtcaaaaga aaagtagacc ttgaattgat ccccattcca   1500

ttccgtccct aa                                                       1512


<210> SEQ ID NO 19
<211> LENGTH: 1512
<212> TYPE: DNA
<213> ORGANISM: Jatropha curcas

<400> SEQUENCE: 19

atggaacaac aaatcctctc ttttccagtt cttttcagtt tccttctttt tcttctggtc     60

ctattaaaag tatctaagaa attatccaaa catgattcca actctcctcc aggaccatgg    120
```

```
aaattacctt tcttaggtaa tattctccag ctcgctggtg atctccctca ccgccgaata    180
acggagttgg ccaaaaaata cggaccggta atgagtatta aacttggtca gcatccttat    240
cttgttgttt cttcgccgga aacagccaaa gaagtaatga gaacccaaga tcccattttc    300
gctgatcgac cgcttgtcct tgcgggagaa ttagtgcttt acaaccgaaa tgacataggt    360
tttgggctgt acggagatca atggagacaa atgagaaaat tttgcgcatt ggaattactt    420
agcacaaaac gagtacagtc gtttcgatcc gtaagagaag aagaaattgc agagtttgta    480
aaatctctgc gatcaaaaga aggaagttct gttaatctga gtcatacttt atttgcttta    540
acaaactcta taattgcaag aaatactgtc ggccataaaa gcaaaaatca agaagcgttg    600
ctgaaaatta ttgatgatat agttgagtca ctgggaggtc tcagtacagt tgatatcttt    660
ccttccttaa aatggctacc ttcagtcaaa agggaaaggt caagaatttg gaaattgcat    720
tgtgaaacag atgagattct tgaaggtatc ttagaagagc ataaagcgaa caggcaggcc    780
gcagctttca agaacgacga tgggagccaa gctgataatc ttcttgatgt tcttttggat    840
cttcagcaaa atggaaatct tgaagttcct ttaactgacg tcaacatcaa agcagtaatc    900
cttggtatgt ttggcgctgg aagcgacaca tcctccaaaa caacagaatg ggcaatggcg    960
gagttgatga aaaatccgga aataatgaaa aaggcacaag aagaattgcg gagtttgttt   1020
ggtgaaagtg gatacgttga tgaagcaaaa cttcacgaaa taaaatggtt gaagttaatt   1080
attaatgaaa cattgagatt acatcctgca gttacattaa ttccaaggct ttgcagggaa   1140
aagaccaaag ttagtggata tgacgtttat cctaatacta gggttttcat aaatacatgg   1200
gcaatcggaa gagatcctac aatttggagt gaacctgaga aattcgttcc ggagagattt   1260
attgatagtt caattgatta taggggcaac cattttgaat atactccatt tggtgcagga   1320
agaagaatat gccctggaat ggcattcggt atggttaatc tagagatttt ccttgcaaat   1380
ttgctatatc attttgactg gaaacttcct aaaggaataa cttcggagaa tcttgacatg   1440
actgagaatt ttggaggagt tatcaaaaga aaacaagacc ttgaattgat tcccgcacca   1500
ttccgtcctt aa                                                        1512
```

<210> SEQ ID NO 20
<211> LENGTH: 1509
<212> TYPE: DNA
<213> ORGANISM: Jatropha curcas

<400> SEQUENCE: 20

```
atggaacagc aaatcctctc agtttcagtt ctttccagtt tcgttctttt tcttttcgtc     60
ttattaaaag tatccaagaa attatacaaa catgattcta accctccgcc aggaccatgg    120
aaattacctt tcttaggtaa tatcctccag ctcgccggcg acgcacctca tcaccggttt    180
gcggagttgg ccagaactta tggaccggta atgggtatta aactcggtga aattcccttt    240
cttgttgttt cctcgccgga agcagccaaa gaagtgatga aaatacaaga tcccatcttt    300
gcagaacgag cgcttgtctt tgcaaatgat gtgttgaact ataaccgtaa cgttatggtt    360
tttgggtcat acggatatca atggaggcaa ttgagaaaat tttgtacgtt ggcattactg    420
agcgcaaaac gagtacagtc gtttcaatca gtaagaaaag aagaaatggc tgattttgta    480
aactttctgc gttccaaaga aggaagttct gttaatctta ctcatactat atttgctttt    540
acaaattcta taattgcaag aaatgctgtt ggtcataaaa ccaaaaatca agaaacgttg    600
ttaacatgta ttgatggtat tatttatact ggaggagtaa atatagctga cgtgtttcct    660
```

-continued

```
tccttaaaat ggcttccttc agtcaagagg gaaaaatcta gagttatgaa attgcattat    720

gaaacagata agatcctgga agatatctta caagagcata aagcaaacaa gcaggcgtgg    780

gtttccgagg atggcgatgg gaggaaagct ggcaatttcg ttgatgttct tctggacctt    840

caacaaagtg gaaatcttga ttttccctta actgatgtca ccattaaagc atcaaccatc    900

gatgcttttg tgggtggaag tgacacatcc tcaaaaacta cagaatgggc aatggcagag    960

ttgatgagga aaccggaaat aatgaaaaaa gcgcaagaag aattgcggag tgtctttggt   1020

gaaaaagggt acattgagga agcaaaactc caggaattaa aatggttgaa gttaattatt   1080

aaagaaacaa tgagattaca tcctgtactt tcactacttc caagggtttg taagcaaaag   1140

actaaagtta gtggatatga tgtttatcct ggtactcaag ttctggttaa tgtatgggca   1200

ctcggaagag atcctaaaca ttggagtgaa cctgaaaaat tcaatcccga gagatttatt   1260

gatagttcaa tcgattatct gggaaatcat tttgaatatc ttccatttgg tgcaggaaaa   1320

agagtatgcc ctggaattgc attaggtatg gttcatatgg aaaatttcct cgcaaatttg   1380

ctctttcatt ttgactggaa atttcctaaa ggaattactg cagagaatct tgacatgacc   1440

gatgcttttg gaggagttat gaagagaaaa gtagaccttg aactgattcc cattccatac   1500

catccttaa                                                           1509


<210> SEQ ID NO 21
<211> LENGTH: 1512
<212> TYPE: DNA
<213> ORGANISM: Jatropha curcas

<400> SEQUENCE: 21

atggaacatc aaatcctctc atttccagct cttttcagtt tccttctttt tcttctggtc     60

ttattaaaag tatccaagaa attatacaaa catgattcta accctccacc cggaccatgg    120

aaattacctt tcttaggtaa cattctccag cttgccggcg acacatttca tagacggtta    180

acagagttgg ctaaaactca tggcccggta atgagtatta atgtcggtca gattccttat    240

gttgtcgttt cttccccgga aacagccaaa gaagtaatga aaattcaaga tccagttttc    300

gccgaccatc cggttgtcct tgcagcagaa gtaattcttt atagcccata cgacatcttt    360

tttgcgccct acggagatca cttgaaacaa atgagaaaat tttgcacggt cgaattactt    420

agcacaaaac gagtacagtc gtttcgatct gtgagagaag aagaagttgc agattttgta    480

aaatttctgc gttcaaaaga gggaagttct gttaatctta ctcatacttt atttgctttg    540

acaaattcta tagttgcaag aactgctgtt ggtcatagaa gcaaaaatca agaaggattg    600

ttaaaagtta ttgatgaagc agttttagct tcatcaggtg ttaatatagc tgatatcttt    660

ccttccttac aatggcttcc ttcagtcaaa agggaaaggt ctagaatttg gaaaacgcat    720

cgtgaaacag ataagattct cgaagatgtt ttgcaagagc atagagctaa caggaaggcg    780

gcagttccca agaatggaga tcagagccaa gctgataatc ttcttgatgt tcttttggat    840

cttcaagaaa gtggaaatct tgatgttccc ttacctgatg ccgccatcaa aggaacaatc    900

atggaaatgt ttggggctgg cagcgacacg tcctcaaaaa cagtagaatg ggcaatggca    960

gagttgatga ggaatccaga agtaatgaga aaagcacaag aagaattgcg gagtttcttt   1020

ggtgaaaatg gagaggttga ggatgcaaaa attcaggaat taaaatgttt aaagttaatt   1080

attaaagaaa cattgagatt acatcctcca ggtgcagtaa ttccaaggct ttgtagggaa   1140

agaactaaag tcgctggata cgacatttat cctaatacta agattttcgt taatacatgg   1200

gcaattggaa gagatcctga aatttggagt gaagctgaga aattcaatcc cgacagattt   1260
```

-continued

```
attgacagtt caattgatta taagggtaac aattttgaac tgattccatt tggtgcagga   1320

agaagaatat gccccggaat tacattagct tcagctaata tggaactttt ccttgcaaac   1380

ttgctatatc attttgactg gaaatttcct caaggaataa cagcagagaa tctcgacatg   1440

aatgaatgtt ttggaggagc tgtcaaaaga aaagtagacc ttgaactcat tcctattcca   1500

ttccgtactt aa                                                         1512
```

<210> SEQ ID NO 22
<211> LENGTH: 1500
<212> TYPE: DNA
<213> ORGANISM: Jatropha curcas

<400> SEQUENCE: 22

```
atgctctcat ttccagttat tttcagtttc cttcttttcc ttctcgtctt attaaaagta     60

tccaaaaaat tatgcaaaga taattctatc cctccgccgg gaccatggca attacctttc    120

ttgggtaaca ttttccagct cgcaggctac caatttcata tccggttaag cgagttgggc    180

caaacttatg gaccagtaat gggtattaaa gtcggtcaag ttccttttct tatcgtttct    240

tcgccggaaa tggccaaaga agtgttgaaa gtccaagatc ccactttcgt cgaccgaccg    300

gttgtccttg cagcagaatt ggtgatgtat gggggccacg acatcgttta tgcgccatac    360

ggagatcaat ggagacaaat gagaaaattt tgcacgttag agttacttag cacaaaacga    420

gtgcaatcct ttcgatccgt aagagaagaa gaagctggag agtttgtaaa atttctactt    480

tcaaaagagg gaagttctgt taaccttact catgctttat atgctttatc aaattctatg    540

gttgcaagaa gtactgttgg tcataaaacc aaaaatcaag aagcgttatt aaacgttatt    600

gatgatacag tttcaacagc ggcaggtact aatatagccg atatctttcc gtccttaaaa    660

tggcttccta cagtcaaacg gcagatgtct agaatttgga aatctcattg tcaaacagat    720

gagattcttg aaggtatctt aagagagcat agagctaaaa ggcagacggc agcttccaag    780

aacggtgatc gggctgaagc cgataatctt cttgatgttc ttttggatct tcaacagaga    840

ggagatcttg atgttccctt aactgatatc aacatcaaag gagcaatcct ggaaatgttt    900

ggcgctggaa gcgacacatc tacaaaaact ttagaatggg caatgtcaga attgatgagg    960

aacccaaaaa tgatgaaaaa agtacaacaa gaattgcgga gtttctttgg tgaaaatgga   1020

aaagttgagg aagcaaaact tcaggaatta aaatggttaa agttaattat taaagaaaca   1080

ttgagattac atcctccaat tgcagtaatt ccaaggcttt gtagggagag gactaaagtt   1140

tgtggatatg acgtttatcc taataccagg gttttcgtta atgtctgggc aatgggaaga   1200

gatcctaaaa tttggaatga agctgaaaaa ttcaatcctg agagatttat tgatagttca   1260

attgattata ggggtaataa ttttgaactg attccatttg gtgcaggaaa aagaatatgc   1320

cctggaatta cattagctat tgttcatgta gaaactgtcc ttgcaaactt gctatatcac   1380

tttgactgga aatttcctga aggagtaact gcagagaatt ttgatatgaa tgaaactttt   1440

gcaggaatta tccgaagaaa agtagacctt gaactgatcc ctgttgcatt ccgtccttaa   1500
```

<210> SEQ ID NO 23
<211> LENGTH: 1488
<212> TYPE: DNA
<213> ORGANISM: Jatropha curcas

<400> SEQUENCE: 23

```
atggaccacc gaattctctc attcccattc ctaatgctaa gcttgcttct tcctttcgtt     60
```

-continued

```
ttcgagttgt taaagatatg gaagaagagt aataataatc ctcctccagg accttggaga    120
ttacctctga tcggtaacat tcaccagttg ggtgggcgtc atcaacccca tctccgcctt    180
acagacttgg ccagaactta tggacccgtt atgcgcctgc agcttggcca aattgaagca    240
gtagtcattt cctcagctga aacagccaaa caagttatga aaacccaaga aagccaattc    300
cttggaagac cttctctttt agctgccgat atcatgcttt ataaccgtac agacatctct    360
ttcgcccctt atggagatta ctggagacaa atgaaaaaaa ttgctgtcgt tgagctcctt    420
agcgccaagc gtgtccaagc ctacaaatca gtcatggatg aggaagtttc caatttcatc    480
aattttcttt attcaaaagc ggggtcgcct gtgaatctta ctaagacatt ctattcctta    540
ggaaatggaa tcatcgcaaa aacatccatc ggcaaaaaat ttaagaaaca agaaaccttc    600
ttaaaagtcg tagacaaagc cattagagta gcaggaggtt tcagtgtggg ggatgcgttt    660
ccttccttta aattgattca cttgatcact ggaatcagct ccacactcca tacagctcat    720
caagaggcag acgagattct tgaagaaatt ataagcgaac acagagccag taagactgct    780
gatggtgatg actatgaagc cgataatatt cttggcgttc ttttggatat tcaagaacgt    840
gggaaccttc aagtcccctt gaccacggac aatatcaaag ctatcattct ggacatgttt    900
gccggtgcaa gtgacacatc gttaacaact gcagaatggg caatggcaga aatggtaaag    960
catccaagaa taatgaagaa agcacaagac gaagttaggc ggactttgaa ccaagaagga   1020
aacgtagcta atcttcttcc tgaactgaaa tatttgaaat tagttatcaa agaaaccttg   1080
agattacatc ctccagtagc cttaattcct agagaatgtg atgggcgatg tgagcttaat   1140
gggtacgatg ttaatcctaa aactaagatt cttgttaacg catgggcaat cggaagagat   1200
cataatttat ggaatgatcc tgaaagattt gatccggaga gatttcttga caattcaagt   1260
gatttcaggg gaaccgactt caaattcatt ccatttggcg ccggaaagag gatttgtcct   1320
ggcataacca tggctataac tattattgag gtcctgcttg cacaattgct ctaccatttt   1380
gattggaaac ttcctgatgg agctaaacca gaaagtcttg acatgtctga tacatttggt   1440
ctcgtagtta agagaaggat agatctcaat ttgattccaa tcccatag                1488
```

<210> SEQ ID NO 24
<211> LENGTH: 1497
<212> TYPE: DNA
<213> ORGANISM: Jatropha curcas

<400> SEQUENCE: 24

```
atggagtatc aaatcctctc atctccaacc cttatagcct tgttggtttt tgtggcgaca     60
gtggtgataa aattatggaa gagacccaca atagctaaca acaatcctcc accaggacct    120
tggaagttgc ctctgatagg caaccttcat aatttgtttg gccgtgatca gccacaccac    180
cgcctccgag atttggccgg aaagtatgga gccgtaatgg gttttcagct tggacaggtt    240
cccactgttg taatatcctc ggcagaaata gccaaacaag tcttaaaaac ccatgagttc    300
caattcatcg acagaccctc tctcttggct gccgatatcg tgctttataa tcgttctgac    360
attatatttg ccccttacgg agactactgg agacaaatca agaaaattgc catactcgag    420
ctgcttagtt caaagcgcgt gcagtcattc aaatcagtga gagaagagga ggtctccagt    480
ttcttcaagt tcttatattc aaaagctgga tcgcctgtca atcttagtcg gactctcttg    540
tctttaacta atgggatcat agccaaaact tccataggta agaaatgcaa aagacaggaa    600
gaaatcattg cagttataac ggatgccatt aaagcaacag gaggtttcag cgtcgccgat    660
gtttttccct cctttaaatt tcttcacatt attaccggca tcagctctac tatccgcagg    720
```

```
attcatcgag aggcagatac gattcttgaa gaaattatgg acgaacacaa agccaacaac    780
gaatcaaaga atgaacccga taacattctg gatgttcttt tggatattca acagcgagga    840
aaccttgaat tccccctcac cgctgacaac atcaaagcta tcattctgga aatgtttgga    900
gctgcgagtg acacatcttc cgtgaccatt gaatgggcaa tgtctgaaat gatgaagaac    960
ccatggacga tgaaaaaagc tcaagaagaa gtaagggagg tatttaatgg aacaggtgac   1020
gtcagcgaag caagccttca agaattacaa tatttgaagt tagttatcaa agaaactcta   1080
agattgcatc ctccgctcac cttaatccct agagaatgca atcagaaatg tcagattaat   1140
gaatatgata tttatccaaa aaccagagtc cttgtcaatg catgggccat cggaagagat   1200
cctaactggt ggactgatcc tgaaagattt gatccagaga gatttcgttg cggttcagtt   1260
gatttcaaag gcactgactt tgagttcatc ccttttggtg ctggtaaaag aatgtgtccc   1320
ggcataacca tggctatggc taacattgaa cttatacttg cacaactact gtaccatttt   1380
aactgggaac ttcctggaaa agctaaacca gaaactctcg acatgtctga gagtttcggt   1440
cttgcagtta aaagaaaagt cgagcttaac ttgattccga ccgcgtttaa tccttag      1497
```

<210> SEQ ID NO 25
<211> LENGTH: 1512
<212> TYPE: DNA
<213> ORGANISM: Jatropha curcas

<400> SEQUENCE: 25

```
atggaacaac aaatcctctc ttttccagtt attttcaatt tccttctttt tcttctggtc     60
ctattaaaag tatctaagaa attatccaaa catgattcga actctcctcc aggaccatgg    120
aaattacctt tcttaggtaa ttttctccag ctcgctggtg atctccctca ccgccgaata    180
acggagttgg ccaaaaaata cggaccggta atgagtatta aacttggtca gcatccttat    240
cttgttgttt cttcgccgga aacagccaaa gaagtaatga gaacccaaga tcccattttc    300
gctgatcgac cgcttgtcct tgctggagaa ttagtgcttt acaaccgaaa tgacataggt    360
tttgggctgt acggagatca atggagacaa atgagaaaat tttgcgcatt ggaattactt    420
agcacaaaac gaatacagtc gtttcgatcc gtaagggaag aagaaattgc agtgtttgta    480
aaatctctgc gatcaaaaga aggaagttct gttaatctga gtcatacttt atttgcttta    540
acaaactcta taattgcaag aaatactgtc ggccataaaa gcaaaaaatca agaagcgttg    600
ctgaaaatta ttgatgatat agttgagtca ctaggaggtc tcagcacagt tgatatcttt    660
ccttccttaa aatggctacc ttcagtcaaa agggaaaggt caagaatttg gaaattgcat    720
tgtgaaacag atgagattct tgaaggtatc ttagaagagc ataaagcgaa caggcaggcc    780
gcagctttca agaacgacga tgggagccaa gctgataatc ttcttgatgt tcttttggat    840
cttcaacaaa atggaaatct tcaagttcct ttaactgacg tcaacatcaa agcagtaatc    900
cttggtatgt ttggcgctgg aagcgacaca tcctccaaaa ctacagaatg ggcaatggcg    960
gagttgatga aaaatccgga aataatgaaa aacgcacaag aagaattgcg gagtttgttt   1020
ggtgaaagtg gaaacgttga tgaagcaaaa cttcacgaaa taaaatggtt gaagttaatt   1080
attaatgaaa cattgagatt acatcctgca gttacattaa ttccaaggct ttgcagggaa   1140
aagactaaaa ttagtggata tgacgtctat cctaatacta gggttttcat aaatacatgg   1200
gcaatcggaa gagatcctat aatttggact gaacctgaga aattcgttcc ggaaagattt   1260
attgatagtt caattgatta caggggcaac cattttgaat atactccatt tggtgcagga   1320
```

-continued

```
agaagaatat gccctggaat gacatttggt atggttaatc tagagatttt ccttgcaaat   1380

ttgctatatc attttgactg gaaacttcct aaaggaataa cttcggagaa ccttgacatg   1440

actgagaatt ttggaggagt tatcaaaaga aaacaagacc ttgaattgat tcccgtacca   1500

ttccgtcctt aa                                                       1512


<210> SEQ ID NO 26
<211> LENGTH: 1512
<212> TYPE: DNA
<213> ORGANISM: Jatropha curcas

<400> SEQUENCE: 26

atggaagacc aaatcctctc atttcaagtt cttttcagtt tccttctttt tcttttcgtc     60

ttattcaaag tatccaagaa attgtacaaa catggttcta accctccgcc cggaccactg    120

aaattacctt tcttaggtaa tattctccag ctcgccggag atgtacctca ccgccggtta    180

acagccttgg ccaaaactta cggacccgta atgggtatta aactcggtca gattcctttc    240

cttgtcgtgt cctccccgga aacagctaaa gaagtaatga aaatacaaga tcccgttttc    300

gcagaacgag cgcctctcct tgcaggagaa atagtgcttt ataaccgaaa cgacatcatt    360

tttggattgt acggagatca gtggaggcaa atgagaaaaa tttgcacgtt ggaattactt    420

agcgcgaaac gagtacagtc ctttcgatca gtgagagaag aagaagtcgc agatttagtc    480

aaatttcttg gttcgaaaga gggaagtcct gttaatctta ctcatacttt attcgcttta    540

gcaaattcta taattgcaag aaatacggtt ggtcagaaaa gcaaaaacca agaagcattg    600

ctaagactta ttgatgatat aattgaatta acaggaagtg ttagtatagc tgatatattt    660

ccttccttaa aatggcttcc ttcagtccaa agggataggt ctagaattag gaaattgcat    720

tatgaaacag atgagatcct tgaagatatt ttacaagagc atagagctaa caggcaggct    780

gcggcttcca ggaaaggcga tcggaggga gctgataatc ttcttgatgt tcttttgtat    840

cttcaagaaa ctggaaatct tgatgttcct ttaactgatg tcgctatcaa agcagcaatc    900

attgatatgt ttggagctgg aagcgacaca tcctcaaaaa ccgtagaatg ggcaatggct    960

gagttgatga ggaatccaga aataatgaag aaagcacaag aagaattgcg gaatttcttt   1020

ggtgaaaatg gaaaggttga cgaagcaaaa cttcaagaat taaaatggtt aaatttaatt   1080

aataaagaaa cattgagatt acatcctgca gcagctgtag ttccaagggt ttgtagggaa   1140

aggactaagg tgagtggata tgacgtttat cctggcactc gggttttcat taacgcatgg   1200

gcaatcggaa gagatcctaa agtttggagt gaagctgaga aattcaaacc ggagagattt   1260

attgatagtg caattgatta taggggtacc aattttgaac taattccatt tggagcagga   1320

aaaagaatat gccctggaat gactctaggt atggctaatc tggagatttt cctggcaaac   1380

ttgctatatc attttgactg gaaatttcct aaaggagtaa ctgcagaaaa tcttgacatg   1440

aacgaagctt ttggagcagc tgtcaaaaga aaagtagacc ttgaattggt tcccattcca   1500

ttccgtcctt aa                                                       1512


<210> SEQ ID NO 27
<211> LENGTH: 533
<212> TYPE: PRT
<213> ORGANISM: Ricinus communis

<400> SEQUENCE: 27

Met Ser Ser Gln Pro Ala Val Leu Gln Ser Asn Phe Leu Asn Arg Asn
1               5                   10                  15
```

-continued

```
Val Gln Pro Phe Leu Thr Ile Pro Ser Ala Ser Thr Lys Tyr Ser Gly
            20                  25                  30

Thr Ala Cys Phe Ser Ser Phe Pro Ser Val Lys Leu Asn Ala Arg Pro
        35                  40                  45

Pro Gln Ala Cys Phe Ser Leu Asn Lys Asn Asn Asp His Ser Thr Pro
    50                  55                  60

Thr Ser Ile Leu Pro Pro Gly Pro Trp Gln Leu Pro Leu Ile Gly Asn
65                  70                  75                  80

Ile His Gln Leu Val Gly His Leu Pro His Ser Arg Leu Arg Asp Leu
                85                  90                  95

Gly Lys Ile Tyr Gly Pro Val Met Ser Val Gln Leu Gly Glu Val Ser
            100                 105                 110

Ala Val Val Val Ser Ser Val Glu Ala Ala Lys Glu Val Leu Arg Ile
        115                 120                 125

Gln Asp Val Ile Phe Ala Glu Arg Pro Pro Val Leu Met Ala Glu Ile
    130                 135                 140

Val Leu Tyr Asn Arg His Asp Ile Val Phe Gly Ser Tyr Gly Asp His
145                 150                 155                 160

Trp Arg Gln Leu Arg Lys Ile Cys Thr Leu Glu Leu Leu Ser Leu Lys
                165                 170                 175

Arg Val Gln Ser Phe Lys Ser Val Arg Glu Asp Glu Phe Ser Asn Phe
            180                 185                 190

Ile Lys Tyr Leu Ser Ser Lys Ala Gly Thr Pro Val Asn Leu Thr His
        195                 200                 205

Asp Leu Phe Ser Leu Thr Asn Ser Val Met Leu Arg Thr Ser Ile Gly
    210                 215                 220

Lys Lys Cys Lys Asn Gln Glu Ala Ile Leu Arg Ile Ile Asp Ser Val
225                 230                 235                 240

Val Ala Ala Gly Gly Gly Phe Ser Val Ala Asp Val Phe Pro Ser Phe
                245                 250                 255

Lys Leu Leu His Met Ile Ser Gly Asp Arg Ser Ser Leu Glu Ala Leu
            260                 265                 270

Arg Arg Asp Thr Asp Glu Ile Leu Asp Glu Ile Ile Asn Glu His Lys
        275                 280                 285

Ala Gly Arg Lys Ala Gly Asp Asp His Asp Glu Ala Glu Asn Leu Leu
    290                 295                 300

Asp Val Leu Leu Asp Leu Gln Glu Asn Gly Asp Leu Glu Val Pro Leu
305                 310                 315                 320

Thr Asn Asp Ser Ile Lys Ala Thr Ile Leu Asp Met Phe Gly Ala Gly
                325                 330                 335

Ser Asp Thr Ser Ser Lys Thr Ala Glu Trp Ala Leu Ser Glu Leu Met
            340                 345                 350

Arg His Pro Glu Ile Met Lys Lys Ala Gln Glu Glu Val Arg Gly Val
        355                 360                 365

Phe Gly Asp Ser Gly Glu Val Asp Glu Thr Arg Leu His Glu Leu Lys
    370                 375                 380

Tyr Leu Lys Leu Val Ile Lys Glu Thr Leu Arg Leu His Pro Ala Ile
385                 390                 395                 400

Pro Leu Ile Pro Arg Glu Cys Arg Glu Arg Thr Lys Ile Asn Gly Tyr
                405                 410                 415

Asp Val Tyr Pro Lys Thr Lys Val Leu Val Asn Ile Trp Ala Ile Ser
            420                 425                 430

Arg Asp Pro Asn Ile Trp Ser Glu Ala Asp Lys Phe Lys Pro Glu Arg
```

```
        435                 440                 445

Phe Leu Asn Ser Ser Leu Asp Tyr Lys Gly Asn Tyr Leu Glu Phe Ala
    450                 455                 460

Pro Phe Gly Ser Gly Lys Arg Val Cys Pro Gly Met Thr Leu Gly Ile
465                 470                 475                 480

Thr Asn Leu Glu Leu Ile Leu Ala Lys Leu Leu Tyr His Phe Asp Trp
                485                 490                 495

Lys Leu Pro Asp Gly Ile Thr Pro Glu Thr Leu Asp Met Thr Glu Ser
            500                 505                 510

Val Gly Gly Ala Ile Lys Arg Arg Thr Asp Leu Asn Leu Ile Pro Val
        515                 520                 525

Leu Tyr Pro Thr His
    530


<210> SEQ ID NO 28
<211> LENGTH: 501
<212> TYPE: PRT
<213> ORGANISM: Ricinus communis

<400> SEQUENCE: 28

Met Glu Gln Gln Leu Leu Ser Phe Pro Ala Leu Leu Ser Phe Leu Leu
1               5                   10                  15

Leu Ile Phe Val Val Leu Arg Ile Trp Lys Gln Tyr Thr Tyr Lys Gly
            20                  25                  30

Lys Ser Thr Pro Pro Pro Gly Pro Trp Arg Leu Pro Leu Leu Gly Asn
        35                  40                  45

Phe His Gln Leu Val Gly Ala Leu Pro His His Arg Leu Thr Glu Leu
    50                  55                  60

Ala Lys Ile Tyr Gly Pro Val Met Gly Ile Gln Leu Gly Gln Ile Ser
65                  70                  75                  80

Val Val Ile Ile Ser Ser Val Glu Thr Ala Lys Glu Val Leu Lys Thr
                85                  90                  95

Gln Gly Glu Gln Phe Ala Asp Arg Thr Leu Val Leu Ala Ala Lys Met
            100                 105                 110

Val Leu Tyr Asn Arg Asn Asp Ile Val Phe Gly Leu Tyr Gly Asp His
        115                 120                 125

Trp Arg Gln Leu Arg Lys Leu Cys Thr Leu Glu Leu Leu Ser Ala Lys
    130                 135                 140

Arg Val Gln Ser Phe Lys Ser Val Arg Glu Glu Glu Leu Ser Asn Phe
145                 150                 155                 160

Val Lys Phe Leu His Ser Lys Ala Gly Met Pro Val Asn Leu Thr His
                165                 170                 175

Thr Leu Phe Ala Leu Thr Asn Asn Ile Met Ala Arg Thr Ser Val Gly
            180                 185                 190

Lys Lys Cys Lys Asn Gln Glu Ala Leu Leu Ser Ile Ile Asp Gly Ile
        195                 200                 205

Ile Asp Ala Ser Gly Gly Phe Thr Ile Ala Asp Val Phe Pro Ser Val
    210                 215                 220

Pro Phe Leu His Asn Ile Ser Asn Met Lys Ser Arg Leu Glu Lys Leu
225                 230                 235                 240

His Gln Gln Ala Asp Asp Ile Leu Glu Asp Ile Ile Asn Glu His Arg
                245                 250                 255

Ala Thr Arg Asn Arg Asp Asp Leu Glu Glu Ala Glu Asn Leu Leu Asp
            260                 265                 270
```

-continued

```
Val Leu Leu Asp Leu Gln Glu Asn Gly Asn Leu Glu Val Pro Leu Thr
        275                 280                 285

Asn Asp Ser Ile Lys Gly Ala Ile Leu Asp Met Phe Gly Ala Gly Ser
    290                 295                 300

Asp Thr Ser Ser Lys Thr Ala Glu Trp Ala Leu Ser Glu Leu Met Arg
305                 310                 315                 320

His Pro Glu Glu Met Lys Lys Ala Gln Glu Glu Val Arg Arg Ile Phe
                325                 330                 335

Gly Glu Asp Gly Arg Ile Asp Glu Ala Arg Phe Gln Glu Leu Lys Phe
            340                 345                 350

Leu Asn Leu Val Ile Lys Glu Thr Leu Arg Leu His Pro Pro Val Ala
        355                 360                 365

Leu Ile Pro Arg Glu Cys Arg Glu Lys Thr Lys Val Asn Gly Tyr Asp
    370                 375                 380

Ile Tyr Pro Lys Thr Arg Thr Leu Ile Asn Val Trp Ser Met Gly Arg
385                 390                 395                 400

Asp Pro Ser Val Trp Thr Glu Ala Glu Lys Phe Tyr Pro Glu Arg Phe
                405                 410                 415

Leu Asp Gly Thr Ile Asp Tyr Arg Gly Thr Asn Phe Glu Leu Ile Pro
            420                 425                 430

Phe Gly Ala Gly Lys Arg Ile Cys Pro Gly Met Thr Leu Gly Ile Val
        435                 440                 445

Asn Leu Glu Leu Phe Leu Ala His Leu Leu Tyr His Phe Asp Trp Lys
    450                 455                 460

Leu Val Asp Gly Val Ala Pro Asp Thr Leu Asp Met Ser Glu Gly Phe
465                 470                 475                 480

Gly Gly Ala Leu Lys Arg Lys Met Asp Leu Asn Leu Val Pro Ile Pro
                485                 490                 495

Phe Thr Thr Leu Pro
            500


<210> SEQ ID NO 29
<211> LENGTH: 497
<212> TYPE: PRT
<213> ORGANISM: Ricinus communis
<220> FEATURE:
<221> NAME/KEY: misc_feature
<222> LOCATION: (359)..(359)
<223> OTHER INFORMATION: Xaa can be any naturally occurring amino acid

<400> SEQUENCE: 29

Met Glu Lys Gln Ile Leu Ser Phe Pro Val Leu Leu Ser Phe Val Leu
1               5                   10                  15

Phe Ile Leu Met Ile Leu Arg Ile Trp Lys Lys Ser Asn Pro Pro Pro
            20                  25                  30

Gly Pro Trp Lys Leu Pro Leu Leu Gly Asn Ile His Gln Leu Ala Gly
        35                  40                  45

Gly Ala Leu Pro His His Arg Leu Arg Asp Leu Ala Lys Thr Tyr Gly
    50                  55                  60

Pro Val Met Ser Ile Gln Leu Gly Gln Ile Ser Ala Val Val Ile Ser
65                  70                  75                  80

Ser Val Gln Gly Ala Lys Glu Val Leu Lys Thr Gln Gly Glu Val Phe
                85                  90                  95

Ala Glu Arg Pro Leu Ile Ile Ala Ala Lys Ile Val Leu Tyr Asn Arg
            100                 105                 110

Lys Asp Ile Val Phe Gly Ser Tyr Gly Asp His Trp Arg Gln Met Arg
```

```
        115                 120                 125

Lys Ile Cys Thr Leu Glu Leu Leu Ser Ala Lys Arg Val Gln Ser Phe
    130                 135                 140

Arg Ser Val Arg Glu Glu Glu Val Ser Glu Phe Val Arg Phe Leu Gln
145                 150                 155                 160

Ser Lys Ala Gly Thr Pro Val Asn Leu Thr Lys Thr Leu Phe Ala Leu
                165                 170                 175

Thr Asn Ser Ile Met Ala Arg Thr Ser Ile Gly Lys Lys Cys Glu Lys
            180                 185                 190

Gln Glu Thr Phe Ser Ser Val Ile Asp Gly Val Thr Glu Val Ser Gly
        195                 200                 205

Gly Phe Thr Val Ala Asp Val Phe Pro Ser Leu Gly Phe Leu His Val
    210                 215                 220

Ile Thr Gly Met Lys Ser Arg Leu Glu Arg Leu His Arg Val Ala Asp
225                 230                 235                 240

Gln Ile Phe Glu Asp Ile Ile Ala Glu His Lys Ala Thr Arg Ala Leu
                245                 250                 255

Ser Lys Asn Asp Asp Pro Lys Glu Ala Ala Asn Leu Leu Asp Val Leu
            260                 265                 270

Leu Asp Leu Gln Glu His Gly Asn Leu Gln Val Pro Leu Thr Asn Asp
        275                 280                 285

Ser Ile Lys Ala Ala Ile Leu Glu Met Phe Gly Ala Gly Ser Asp Thr
    290                 295                 300

Ser Ser Lys Thr Thr Glu Trp Ala Met Ser Glu Leu Met Arg Asn Pro
305                 310                 315                 320

Thr Glu Met Arg Lys Ala Gln Glu Glu Val Arg Arg Val Phe Gly Glu
                325                 330                 335

Thr Gly Lys Val Asp Glu Thr Arg Leu His Glu Leu Lys Phe Leu Lys
            340                 345                 350

Leu Val Val Lys Glu Thr Xaa Arg Leu His Pro Ala Ile Ala Leu Ile
        355                 360                 365

Pro Arg Glu Cys Arg Glu Arg Thr Lys Val Asp Gly Tyr Asp Ile Lys
    370                 375                 380

Pro Thr Ala Arg Val Leu Val Asn Val Trp Ala Ile Gly Arg Asp Pro
385                 390                 395                 400

Asn Val Trp Ser Glu Pro Glu Arg Phe His Pro Glu Arg Phe Val Asn
                405                 410                 415

Ser Ser Val Asp Phe Lys Gly Thr Asp Phe Glu Leu Leu Pro Phe Gly
            420                 425                 430

Ala Gly Lys Arg Ile Cys Pro Gly Ile Leu Val Gly Ile Thr Asn Leu
        435                 440                 445

Glu Leu Val Leu Ala His Leu Leu Tyr His Phe Asp Trp Lys Phe Val
    450                 455                 460

Asp Gly Val Thr Ser Asp Ser Phe Asp Met Arg Glu Gly Phe Gly Gly
465                 470                 475                 480

Ala Leu His Arg Lys Ser Asp Leu Ile Leu Ile Pro Ile Pro Phe Thr
                485                 490                 495

Pro
```

<210> SEQ ID NO 30
<211> LENGTH: 560
<212> TYPE: PRT
<213> ORGANISM: Euphorbia peplus -continued

<400> SEQUENCE: 30

```
Met Ala Thr Leu Gln His Ser Met Gln Ala Asn Leu Gln Lys Gln Asn
1               5                   10                  15

Leu His Pro Leu Leu Asn Lys Ser Phe Gly Thr Pro Asn Arg Pro Ser
            20                  25                  30

Phe Val Tyr Ser Ser Lys Ser Ala Ser Arg Arg Thr Ile Gln Ala Cys
        35                  40                  45

Leu Ser Ser Asn Ser Gln Pro Gly Gly Val Cys Pro Met Ala Asn Arg
    50                  55                  60

Phe Ala Ser Ser Thr Thr Asn Gln Ser Val Thr Glu Ser Ser Ser Lys
65                  70                  75                  80

Pro Asp Glu Glu Asp Glu Asn Ser Pro Val Lys Leu Pro Pro Gly Pro
                85                  90                  95

Trp Lys Leu Pro Leu Leu Gly Asn Ile Leu Gln Leu Val Gly Asp Leu
            100                 105                 110

Pro His Ser Arg Leu Arg Asp Leu Ala Thr Glu Tyr Gly Pro Val Met
        115                 120                 125

Ser Val Gln Leu Gly Glu Val Tyr Ala Val Val Ile Ser Ser Val Glu
    130                 135                 140

Ala Ala Arg Glu Ile Leu Arg Asn Gln Asp Val Asn Phe Ala Asp Arg
145                 150                 155                 160

Pro Pro Val Leu Val Ser Glu Ile Val Leu Tyr Asn Arg Gln Asp Ile
                165                 170                 175

Val Phe Gly Ala Tyr Gly Val His Trp Arg Gln Met Arg Arg Leu Cys
            180                 185                 190

Thr Thr Glu Leu Leu Ser Ile Lys Arg Val Gln Ser Phe Lys Leu Val
        195                 200                 205

Arg Glu Glu Glu Val Ser Asn Phe Ile Lys Ser Leu Tyr Ser Lys Ala
    210                 215                 220

Gly Lys Pro Val Asn Leu Thr Glu Gly Leu Phe Thr Leu Thr Asn Ser
225                 230                 235                 240

Ile Met Leu Arg Thr Ser Ile Gly Lys Lys Cys Arg Asp Gln Asp Thr
                245                 250                 255

Leu Leu Arg Val Ile Glu Gly Val Val Ala Ala Gly Gly Gly Phe Ser
            260                 265                 270

Ile Ala Asp Val Phe Pro Ser Ala Val Phe Leu His Asp Ile Asn Gly
        275                 280                 285

Asp Lys Ser Gly Leu Gln Ser Leu Arg Arg Asp Ala Asp Leu Ile Leu
    290                 295                 300

Asp Glu Ile Ile Gly Glu His Arg Ala Ile Arg Gly Thr Gly Gly Asp
305                 310                 315                 320

Gln Gly Glu Ala Asp Asn Leu Leu Asp Val Leu Leu Asp Leu Gln Glu
                325                 330                 335

Asn Gly Asn Leu Glu Val Pro Leu Asn Asp Asp Ser Ile Lys Gly Ala
            340                 345                 350

Ile Leu Asp Met Phe Gly Ala Gly Ser Asp Thr Ser Ser Lys Ser Thr
        355                 360                 365

Glu Trp Ala Leu Ser Glu Leu Leu Arg His Pro Glu Glu Met Lys Lys
    370                 375                 380

Ala Gln Asp Glu Val Arg Arg Val Phe Ala Lys Lys Gly Asn Val Glu
385                 390                 395                 400

Glu Ser Gln Leu Asp Gln Leu Lys Tyr Leu Lys Leu Val Ile Lys Glu
                405                 410                 415
```

Thr Leu Arg Leu His Pro Ala Val Pro Leu Ile Pro Arg Glu Cys Arg
420 425 430

Glu Lys Thr Lys Val Asn Gly Tyr Asp Ile Leu Pro Lys Thr Lys Ala
435 440 445

Leu Val Asn Ile Trp Ala Ile Ser Arg Asp Pro Lys Ile Trp Pro Glu
450 455 460

Ala Asp Lys Phe Ile Pro Glu Arg Phe Glu Asn Ser Ser Ile Asp Phe
465 470 475 480

Lys Gly Asn Asn Leu Glu Phe Ala Pro Phe Gly Ser Gly Lys Arg Ile
485 490 495

Cys Pro Gly Met Ala Leu Gly Ile Thr Asn Leu Glu Leu Phe Leu Ala
500 505 510

Gln Leu Leu Tyr His Phe Asp Trp Lys Leu Ala Asp Gly Lys Asp Gly
515 520 525

Arg Asp Leu Asp Met Gly Glu Val Val Gly Gly Ala Ile Lys Arg Lys
530 535 540

Val Asp Leu Asn Leu Ile Pro Ile Pro Phe His Thr Ser Pro Ala Asn
545 550 555 560

<210> SEQ ID NO 31
<211> LENGTH: 558
<212> TYPE: PRT
<213> ORGANISM: euphorbia fischeriana

<400> SEQUENCE: 31

Met Ser Thr Leu Gln Pro Phe Leu Gln Ala Asn Phe Gln Lys Gln Asn
1 5 10 15

Ser His Pro Leu Leu Ser Lys Pro Leu Gly Thr Thr Asn His Pro Ser
20 25 30

Phe Ile Ser Ser Ser Lys Ser Thr Lys Arg Ser Thr Ile Gln Ala Cys
35 40 45

Leu Ser Ser Asn Ser Gln Pro Gly Gly Val Cys Pro Met Ala Asn Arg
50 55 60

Phe Ala Ser Ser Ser Thr Thr Asn Gln Ser Val Thr Gln Ser Ser Ser
65 70 75 80

Asn Pro Asp Glu Lys Asp Gly Asn Ser Gln Val Gln Leu Pro Pro Gly
85 90 95

Pro Trp Lys Leu Pro Phe Ile Gly Asn Ile Leu Gln Leu Val Gly Asp
100 105 110

Leu Pro His Arg Arg Leu Arg Asp Leu Ala Thr Val Tyr Gly Pro Val
115 120 125

Met Ser Val Gln Leu Gly Glu Val Tyr Ala Val Ile Ile Ser Ser Val
130 135 140

Glu Ala Ala Lys Glu Val Leu Arg Thr Gln Asp Val Asn Phe Ala Asp
145 150 155 160

Arg Pro Pro Val Leu Val Ser Glu Ile Val Leu Tyr Asn Arg Gln Asp
165 170 175

Ile Val Phe Gly Ser Tyr Gly Asp His Trp Arg Gln Met Arg Arg Ile
180 185 190

Cys Thr Met Glu Leu Leu Ser Ile Lys Arg Val Gln Ser Phe Lys Ser
195 200 205

Val Arg Glu Glu Glu Val Ser Asn Phe Ile Lys Leu Leu Tyr Ser Glu
210 215 220

Ala Gly Gln Pro Val Asn Leu Thr Glu Lys Leu Phe Ala Leu Thr Asn

-continued

```
225                 230                 235                 240

Ser Ile Met Leu Arg Thr Ser Ile Gly Lys Lys Cys Lys Asp Gln Glu
                245                 250                 255

Thr Leu Leu Arg Val Ile Glu Gly Val Val Ala Ala Gly Gly Gly Phe
            260                 265                 270

Ser Val Ala Asp Val Phe Pro Ser Ala Val Phe Leu His Asp Ile Thr
        275                 280                 285

Gly Asp Lys Ser Gly Leu Glu Ser Leu Arg Arg Asp Ala Asp Leu Val
    290                 295                 300

Leu Asp Glu Ile Ile Gly Glu His Arg Ala Asn Arg Ser Gly Asn Gly
305                 310                 315                 320

Gly Asp Glu Gly Glu Ala Glu Asn Leu Leu Asp Val Leu Leu Asp Leu
                325                 330                 335

Gln Glu Asn Gly Asn Leu Glu Val Pro Leu Asn Asp Asp Ser Ile Lys
            340                 345                 350

Ala Thr Ile Leu Asp Met Phe Gly Ala Gly Ser Asp Thr Ser Ser Lys
        355                 360                 365

Ser Thr Glu Trp Ala Leu Ser Glu Leu Leu Arg His Pro Val Ala Met
    370                 375                 380

Lys Lys Ala Gln Asp Glu Val Arg Lys Val Phe Ser Glu Asn Gly Asn
385                 390                 395                 400

Val Glu Glu Glu Gly Leu Asn Gln Leu Lys Tyr Leu Lys Leu Val Ile
                405                 410                 415

Lys Glu Thr Leu Arg Leu His Pro Ala Ile Pro Leu Ile Pro Arg Glu
            420                 425                 430

Cys Arg Glu Lys Thr Lys Val Asn Gly Tyr Asp Ile Leu Pro Lys Thr
        435                 440                 445

Lys Ala Leu Val Asn Ile Trp Ala Ile Ser Arg Asp Pro Thr Ile Trp
    450                 455                 460

Pro Glu Ala Asp Lys Phe Ile Pro Glu Arg Phe Glu Asn Ser Ser Met
465                 470                 475                 480

Asp Phe Lys Gly Asn His Cys Glu Phe Ala Pro Phe Gly Ser Gly Lys
                485                 490                 495

Arg Ile Cys Pro Gly Met Ala Leu Gly Ile Thr Asn Leu Glu Leu Phe
            500                 505                 510

Leu Ala Gln Leu Leu Tyr His Phe Asp Trp Lys Leu Thr Asp Gly Lys
        515                 520                 525

Asp Pro Arg Asn Leu Asp Met Ser Glu Val Val Gly Gly Ala Ile Lys
    530                 535                 540

Arg Lys Ile Asp Leu Asn Leu Ile Pro Ile Pro Phe His Pro
545                 550                 555


<210> SEQ ID NO 32
<211> LENGTH: 629
<212> TYPE: PRT
<213> ORGANISM: Jatropha curcas

<400> SEQUENCE: 32

Met Ser Leu Gln Pro Ala Ile Leu Gln Gly Asn Thr Cys Lys Gln Tyr
1               5                   10                  15

Phe His Pro Leu Ser Ser Ile Ser Ser Thr Arg Trp Val Gly Asn Cys
            20                  25                  30

Asn Arg Phe Ala Phe Leu Ser Pro Ala Lys Pro Thr Ala Asn Arg Ala
        35                  40                  45
```

-continued

```
Pro Gln Ala Ser Leu Ser Ser Lys Leu Gln Pro Val Val Arg Leu Leu
    50                  55                  60

Thr Lys Phe Pro Ala Ser Gly Phe Leu Ala Met Asn Gln Ser Val Asp
65                  70                  75                  80

Gln Phe Ala Ser Thr Thr Thr Ser Leu Thr Lys Ile Phe Asn Lys Ile
                85                  90                  95

Gly Lys Pro Ile Gln Ser Ser Pro Phe Leu Val Ser Val Leu Leu Leu
            100                 105                 110

Met Phe Met Ala Ser Lys Ile Gln Asn Gln Gln Glu Glu Asp Asp Asn
        115                 120                 125

Ser Ile Asn Leu Pro Pro Gly Pro Trp Arg Leu Pro Phe Ile Gly Asn
    130                 135                 140

Ile His Gln Leu Ala Gly Pro Gly Leu Pro His His Arg Leu Thr Asp
145                 150                 155                 160

Leu Ala Lys Thr Tyr Gly Pro Val Met Gly Val His Leu Gly Glu Val
                165                 170                 175

Tyr Ala Val Val Val Ser Ser Ala Glu Thr Ser Lys Glu Val Leu Arg
            180                 185                 190

Thr Gln Asp Thr Asn Phe Ala Glu Arg Pro Leu Val Asn Ala Ala Lys
        195                 200                 205

Met Val Leu Tyr Asn Arg Asn Asp Ile Val Phe Gly Ser Phe Gly Asp
    210                 215                 220

Gln Trp Arg Gln Met Arg Lys Ile Cys Thr Leu Glu Leu Leu Ser Val
225                 230                 235                 240

Lys Arg Val Gln Ser Phe Lys Ser Val Arg Glu Glu Glu Met Ser Ser
                245                 250                 255

Phe Ile Lys Phe Leu Ser Ser Lys Ser Gly Ser Pro Val Asn Leu Thr
            260                 265                 270

His His Leu Phe Val Leu Thr Asn Tyr Ile Ile Ala Arg Thr Ser Ile
        275                 280                 285

Gly Lys Lys Cys Lys Asn Gln Glu Ala Leu Leu Arg Ile Ile Asp Asp
    290                 295                 300

Val Val Glu Ala Gly Ala Gly Phe Ser Val Thr Asp Val Phe Pro Ser
305                 310                 315                 320

Phe Glu Ala Leu His Val Ile Ser Gly Asp Lys His Lys Phe Asp Lys
                325                 330                 335

Leu His Arg Glu Thr Asp Lys Ile Leu Glu Asp Ile Ile Ser Glu His
            340                 345                 350

Lys Ala Asp Arg Ala Val Ser Ser Lys Lys Ser Asp Gly Glu Val Glu
        355                 360                 365

Asn Leu Leu Asp Val Leu Leu Asp Leu Gln Glu Asn Gly Asn Leu Gln
    370                 375                 380

Phe Pro Leu Thr Asn Asp Ala Ile Lys Gly Ala Ile Leu Asp Thr Phe
385                 390                 395                 400

Gly Ala Gly Ser Asp Thr Ser Ser Lys Thr Ala Glu Trp Thr Leu Ser
                405                 410                 415

Glu Leu Ile Arg Asn Pro Glu Ala Met Arg Lys Ala Gln Ala Glu Ile
            420                 425                 430

Arg Arg Val Phe Asp Glu Thr Gly Tyr Val Asp Glu Asp Lys Phe Glu
        435                 440                 445

Glu Leu Lys Tyr Leu Lys Leu Val Val Lys Glu Thr Leu Arg Leu His
    450                 455                 460

Pro Ala Val Pro Leu Ile Pro Arg Glu Cys Arg Gly Lys Thr Lys Ile
```

-continued 465 470 475 480

Asn Gly Tyr Asp Ile Phe Pro Lys Thr Lys Val Leu Val Asn Val Trp
485 490 495

Ala Ile Ser Arg Asp Pro Ala Ile Trp Pro Glu Pro Glu Lys Phe Asn
500 505 510

Pro Glu Arg Phe Ile Asp Asn Pro Ile Asp Tyr Lys Ser Ile Asn Cys
515 520 525

Glu Leu Thr Pro Phe Gly Ala Gly Lys Arg Ile Cys Pro Gly Met Thr
530 535 540

Leu Gly Ile Thr Asn Leu Glu Leu Phe Leu Ala Asn Leu Leu Tyr His
545 550 555 560

Phe Asp Trp Lys Leu Pro Asp Gly Lys Met Pro Glu Asp Leu Asp Met
565 570 575

Ser Glu Ser Phe Gly Gly Ala Ile Lys Arg Lys Thr Asp Leu Lys Leu
580 585 590

Ile Pro Val Leu Ala Arg Pro Leu Thr Pro Arg Asn Ala Asn Ser Gly
595 600 605

Asn Thr Phe Thr Thr Thr Asp Ala Asp Ser Pro Ala Ser Met Cys Pro
610 615 620

His Leu Lys Ala Leu
625

<210> SEQ ID NO 33
<211> LENGTH: 629
<212> TYPE: PRT
<213> ORGANISM: Jatropha gossypifolia

<400> SEQUENCE: 33

Met Ser Leu Gln Pro Ala Val Leu Gln Ala Asn Thr Cys Lys Gln Tyr
1 5 10 15

Phe His Pro Leu Ser Ser Ile Ser Ser Thr Arg Trp Val Gly Asn Cys
20 25 30

Asn Arg Phe Ala Phe Leu Ser Pro Ala Lys Pro Thr Ala Asn Arg Ala
35 40 45

Pro Gln Ala Ser Leu Ser Ser Lys Leu Gln Pro Val Val Arg Leu Leu
50 55 60

Thr Arg Phe Pro Ala Ser Gly Phe Leu Ala Met Asn Gln Ser Val Asn
65 70 75 80

Gln Phe Ala Ser Thr Thr Thr Ser Leu Ala Lys Ile Phe Asp Lys Ile
85 90 95

Gly Lys Pro Ile Gln Ser Ser Pro Phe Leu Leu Ser Val Leu Leu Leu
100 105 110

Met Phe Met Ala Ser Lys Ile Gln Asn Gln Gln Glu Glu Asp Asn Asn
115 120 125

Ser Ile Asn Leu Pro Pro Gly Pro Trp Arg Leu Pro Phe Ile Gly Asn
130 135 140

Ile His Gln Leu Ala Gly Pro Gly Leu Pro His His Arg Leu Thr Asp
145 150 155 160

Leu Ala Lys Thr Tyr Gly Pro Val Met Gly Val His Leu Gly Glu Val
165 170 175

Tyr Ala Val Val Val Ser Ser Ala Glu Thr Ser Lys Glu Val Leu Arg
180 185 190

Thr Gln Asp Thr Asn Phe Ala Glu Arg Pro Leu Val Asn Ala Ala Lys
195 200 205

-continued

```
Met Val Leu Tyr Asn Arg Asn Asp Ile Val Phe Gly Ser Tyr Gly Asp
    210                 215                 220

Gln Trp Arg Gln Met Arg Lys Ile Cys Thr Leu Glu Leu Leu Ser Leu
225                 230                 235                 240

Lys Arg Val Gln Ser Phe Lys Ser Val Arg Glu Glu Glu Met Ser Ser
                245                 250                 255

Phe Ile Lys Phe Leu Cys Ser Lys Ser Gly Ser Pro Val Asn Leu Thr
            260                 265                 270

His His Leu Phe Val Leu Thr Asn Tyr Ile Ile Ala Arg Thr Ser Ile
        275                 280                 285

Gly Lys Lys Cys Lys Asn Gln Glu Ala Leu Leu Arg Val Ile Asp Asp
    290                 295                 300

Val Val Glu Ala Gly Ala Gly Phe Ser Val Thr Asp Val Phe Pro Ser
305                 310                 315                 320

Phe Glu Ala Leu His Val Ile Ser Gly Asp Lys His Lys Phe Asp Lys
                325                 330                 335

Leu His Arg Glu Thr Asp Lys Ile Leu Glu Asp Ile Ile Ser Glu His
            340                 345                 350

Lys Ala Asp Arg Ala Val Ser Ser Lys Lys Ser Asp Gly Glu Ala Glu
        355                 360                 365

Asn Leu Leu Asp Val Leu Leu Asp Leu Gln Glu Asn Gly Asn Leu Gln
    370                 375                 380

Phe Pro Leu Thr Asn Asp Ala Ile Lys Gly Ala Ile Leu Asp Thr Phe
385                 390                 395                 400

Gly Ala Gly Ser Asp Thr Ser Ser Lys Thr Ala Glu Trp Thr Leu Ser
                405                 410                 415

Glu Leu Ile Arg Asn Pro Gly Ala Met Arg Lys Ala Gln Glu Glu Ile
            420                 425                 430

Arg Arg Val Phe Asp Glu Thr Gly Tyr Val Asp Glu Asp Lys Phe Glu
        435                 440                 445

Glu Leu Lys Tyr Leu Lys Leu Val Val Lys Glu Thr Leu Arg Leu His
    450                 455                 460

Pro Ala Val Pro Leu Ile Pro Arg Glu Cys Arg Gly Lys Thr Lys Ile
465                 470                 475                 480

Asn Gly Tyr Asp Ile Phe Pro Lys Thr Lys Val Leu Val Asn Val Trp
                485                 490                 495

Ala Ile Ser Arg Asp Pro Ala Ile Trp Pro Glu Pro Glu Lys Phe Asn
            500                 505                 510

Pro Glu Arg Phe Ile Asp Asn Pro Ile Asp Tyr Lys Ser Ile Asn Cys
        515                 520                 525

Glu Leu Thr Pro Phe Gly Ala Gly Lys Arg Val Cys Pro Gly Met Thr
    530                 535                 540

Leu Gly Ile Thr Asn Leu Glu Leu Phe Leu Ala Asn Leu Leu Tyr His
545                 550                 555                 560

Phe Asp Trp Lys Leu Pro Asp Gly Lys Met Pro Glu Asp Leu Asp Met
                565                 570                 575

Ser Glu Ser Phe Gly Gly Ala Ile Lys Arg Lys Thr Asp Leu Lys Leu
            580                 585                 590

Ile Pro Val Leu Ala Arg Pro Phe Asn Pro Thr Asn Ala Asn Asn Gly
        595                 600                 605

Asn Thr Phe Thr Thr Thr Asp Ala Asn Ser Pro Ser Ser Met Cys Pro
    610                 615                 620

His Leu Lys Ala Leu
```

625

<210> SEQ ID NO 34
<211> LENGTH: 500
<212> TYPE: PRT
<213> ORGANISM: Euphorbia peplus

<400> SEQUENCE: 34

```
Met Glu Leu Gln Phe Gln Ile Pro Ser Tyr Pro Val Leu Phe Ser Phe
1               5                   10                  15

Phe Ile Phe Ile Phe Ile Leu Ile Lys Ile Val Lys Lys Gln Thr Gln
            20                  25                  30

Asn Ser Ile Ser Pro Pro Gly Pro Trp Lys Tyr Pro Ile Leu Gly Asn
        35                  40                  45

Ile Pro Gln Leu Ala Ala Gly Gly Lys Leu Pro His His Arg Leu Arg
    50                  55                  60

Asp Leu Ala Lys Ile His Gly Pro Val Met Asn Ile Gln Leu Gly Gln
65                  70                  75                  80

Val Lys Ser Ile Val Ile Ser Ser Pro Glu Thr Ala Lys Glu Val Leu
                85                  90                  95

Lys Thr Gln Asp Ile Gln Phe Ala Asn Arg Pro Leu Leu Leu Ala Gly
            100                 105                 110

Glu Met Val Leu Tyr Asn Arg Lys Asp Ile Leu Tyr Gly Leu Tyr Gly
        115                 120                 125

Asp Gln Trp Arg Gln Met Arg Lys Ile Cys Thr Leu Glu Leu Leu Ser
    130                 135                 140

Ala Lys Arg Ile Gln Ser Phe Lys Ser Val Arg Glu Gln Glu Val Glu
145                 150                 155                 160

Ser Phe Ile Arg Leu Leu Arg Ser Lys Ala Gly Ser Pro Val Asn Leu
                165                 170                 175

Thr Thr Ala Val Phe Glu Leu Thr Asn Thr Ile Met Met Ile Thr Thr
            180                 185                 190

Ile Gly Glu Lys Cys Lys Asn Gln Glu Ala Val Met Ser Val Ile Asp
        195                 200                 205

Arg Val Ser Glu Ala Ala Ala Gly Phe Ser Val Ala Asp Val Phe Pro
    210                 215                 220

Ser Leu Lys Phe Leu His Tyr Leu Ser Gly Glu Lys Gly Lys Leu Gln
225                 230                 235                 240

Lys Leu His Lys Glu Thr Asp Glu Ile Leu Glu Glu Ile Ile Ser Glu
                245                 250                 255

His Lys Ala Asn Ala Lys Ile Gly Ser Gln Ala Asp Asn Leu Leu Asp
            260                 265                 270

Val Leu Leu Asp Leu Gln Lys Asn Gly Asn Leu Gln Val Pro Leu Thr
        275                 280                 285

Asn Asp Asn Ile Lys Ala Ala Thr Leu Glu Met Phe Gly Ala Gly Ser
    290                 295                 300

Asp Thr Ser Ser Lys Thr Thr Asp Trp Ala Met Ala Gln Leu Met Arg
305                 310                 315                 320

Lys Pro Ser Ala Met Lys Lys Ala Gln Glu Glu Val Arg Arg Val Phe
                325                 330                 335

Ser Asp Thr Gly Lys Val Glu Glu Ser Arg Ile Gln Glu Leu Lys Tyr
            340                 345                 350

Leu Lys Leu Ile Val Lys Glu Thr Leu Arg Leu His Pro Ala Val Ala
        355                 360                 365
```

-continued

```
Leu Ile Pro Arg Glu Cys Arg Glu Lys Thr Lys Ile Glu Gly Phe Asp
    370                 375                 380

Val Tyr Pro Lys Thr Lys Ile Leu Val Asn Pro Trp Ala Ile Gly Arg
385                 390                 395                 400

Asp Pro Lys Val Trp Ser Asp Pro Glu Ser Phe Asn Pro Glu Arg Phe
                405                 410                 415

Glu Asp Ser Ser Ile Asp Tyr Lys Gly Thr Asn Phe Glu Leu Ile Pro
            420                 425                 430

Phe Gly Ala Gly Lys Arg Ile Cys Pro Gly Met Thr Leu Gly Ile Val
        435                 440                 445

Asn Leu Glu Leu Phe Leu Ala Asn Leu Leu Tyr His Phe Asp Trp Lys
    450                 455                 460

Phe Pro Asn Gly Val Thr Ala Glu Asn Leu Asp Met Thr Glu Ala Ile
465                 470                 475                 480

Gly Gly Ala Ile Lys Arg Lys Leu Asp Leu Glu Leu Ile Pro Ile Pro
                485                 490                 495

Tyr Thr Leu Ser
            500


<210> SEQ ID NO 35
<211> LENGTH: 534
<212> TYPE: PRT
<213> ORGANISM: Ricinus communis

<400> SEQUENCE: 35

Met Ser Leu Gln Pro Ala Pro Val Ser Gln Ser Asn Phe Leu Tyr Lys
1               5                   10                  15

Lys Val Pro Pro Ile Leu Arg Ala Pro Thr Thr Lys Ser Ser Gly Ser
            20                  25                  30

Ser Arg Ser Ser Phe Phe Ser Ser Ser Val Lys Leu Ala Ala Arg Pro
        35                  40                  45

Pro Gln Pro Gln Ala Cys Leu Ser Leu Asn Lys Asn Asp Asp Ser Asn
    50                  55                  60

Thr Ser Ala Ser Ser Leu Pro Pro Gly Pro Trp Lys Leu Pro Leu Leu
65                  70                  75                  80

Gly Asn Ile His Gln Leu Val Gly Ala Leu Pro His His Arg Leu Arg
                85                  90                  95

Asp Leu Ala Lys Ala Tyr Gly Pro Val Met Ser Val Lys Leu Gly Glu
            100                 105                 110

Val Ser Ala Val Val Ile Ser Ser Val Asp Ala Ala Lys Glu Val Leu
        115                 120                 125

Arg Thr Gln Asp Val Asn Phe Ala Asp Arg Pro Leu Val Leu Ala Ala
    130                 135                 140

Glu Ile Val Leu Tyr Asn Arg Gln Asp Ile Val Phe Gly Ser Tyr Gly
145                 150                 155                 160

Glu Gln Trp Arg Gln Met Arg Lys Ile Cys Thr Leu Glu Leu Leu Ser
                165                 170                 175

Ile Lys Arg Val Gln Ser Phe Lys Ser Val Arg Glu Glu Glu Leu Ser
            180                 185                 190

Asn Phe Ile Arg Tyr Leu His Ser Lys Ala Gly Thr Pro Val Asn Leu
        195                 200                 205

Thr His His Leu Phe Ser Leu Thr Asn Ser Ile Met Phe Arg Ile Ser
    210                 215                 220

Ile Gly Lys Lys Tyr Lys Asn Gln Asp Ala Leu Leu Arg Val Ile Asp
225                 230                 235                 240
```

```
Gly Val Ile Glu Ala Gly Gly Gly Phe Ser Thr Ala Asp Val Phe Pro
                245                 250                 255

Ser Phe Lys Phe Leu His His Ile Ser Gly Glu Lys Ser Ser Leu Glu
            260                 265                 270

Asp Leu His Arg Glu Ala Asp Tyr Ile Leu Glu Asp Ile Ile Asn Glu
        275                 280                 285

Arg Arg Ala Ser Lys Ile Asn Gly Asp Asp Arg Asn Gln Ala Asp Asn
    290                 295                 300

Leu Leu Asp Val Leu Leu Asp Leu Gln Glu Asn Gly Asn Leu Glu Ile
305                 310                 315                 320

Ala Leu Thr Asn Asp Ser Ile Lys Ala Ala Ile Leu Glu Met Phe Gly
                325                 330                 335

Ala Gly Ser Asp Thr Ser Ser Lys Thr Ala Glu Trp Ala Leu Ser Glu
            340                 345                 350

Leu Met Arg His Pro Glu Glu Met Glu Lys Ala Gln Thr Glu Val Arg
        355                 360                 365

Gln Val Phe Gly Lys Asp Gly Asn Leu Asp Glu Thr Arg Leu His Glu
    370                 375                 380

Leu Lys Phe Leu Lys Leu Val Ile Lys Glu Thr Leu Arg Leu His Pro
385                 390                 395                 400

Pro Val Ala Leu Ile Pro Arg Glu Cys Arg Gln Arg Thr Lys Val Asn
                405                 410                 415

Gly Tyr Asp Ile Asp Pro Lys Thr Lys Val Leu Val Asn Val Trp Ala
            420                 425                 430

Ile Ser Arg Asp Pro Asn Ile Trp Thr Glu Ala Glu Lys Phe Tyr Pro
        435                 440                 445

Glu Arg Phe Leu His Ser Ser Ile Asp Tyr Lys Gly Asn His Cys Glu
    450                 455                 460

Phe Ala Pro Phe Gly Ser Gly Lys Arg Ile Cys Pro Gly Met Asn Leu
465                 470                 475                 480

Gly Leu Thr Asn Leu Glu Leu Phe Leu Ala Gln Leu Leu Tyr His Phe
                485                 490                 495

Asn Trp Glu Phe Pro Asp Gly Ile Thr Pro Lys Thr Leu Asp Met Thr
            500                 505                 510

Glu Ser Val Gly Ala Ala Ile Lys Arg Lys Ile Asp Leu Lys Leu Ile
        515                 520                 525

Pro Val Leu Phe His Pro
    530
```

<210> SEQ ID NO 36
<211> LENGTH: 523
<212> TYPE: PRT
<213> ORGANISM: Ricinus communis

<400> SEQUENCE: 36

```
Met Glu Ser Ala Ala His Gln Ser Tyr Phe His Met Phe Leu Ala Met
1               5                   10                  15

Glu Gln Gln Ile Leu Ser Phe Pro Val Leu Leu Ser Phe Leu Leu Phe
            20                  25                  30

Ile Phe Met Val Leu Lys Val Trp Lys Lys Asn Lys Asp Asn Pro Asn
        35                  40                  45

Ser Pro Pro Gly Pro Arg Lys Leu Pro Ile Ile Gly Asn Met His Gln
    50                  55                  60

Leu Ala Gly Ser Asp Leu Pro His His Pro Val Thr Glu Leu Ser Lys
```

-continued

```
65                  70                  75                  80

Thr Tyr Gly Pro Ile Met Ser Ile Gln Leu Gly Gln Ile Ser Ala Ile
                85                  90                  95

Val Ile Ser Ser Val Glu Gly Ala Lys Glu Val Leu Lys Thr Gln Gly
            100                 105                 110

Glu Leu Phe Ala Glu Arg Pro Leu Leu Leu Ala Ala Glu Ala Val Leu
        115                 120                 125

Tyr Asn Arg Met Asp Ile Ile Phe Gly Ala Tyr Gly Asp His Trp Arg
    130                 135                 140

Gln Leu Arg Lys Leu Cys Thr Leu Glu Val Leu Ser Ala Lys Arg Ile
145                 150                 155                 160

Gln Ser Phe Ser Ser Leu Arg Gln Glu Glu Leu Ser His Phe Val Arg
                165                 170                 175

Phe Val His Ser Lys Ala Gly Ser Pro Ile Asn Leu Ser Lys Val Leu
            180                 185                 190

Phe Ala Leu Thr Asn Ser Ile Ile Ala Arg Ile Ala Thr Gly Lys Lys
        195                 200                 205

Cys Lys Asn Gln Asp Ala Leu Leu Asp Leu Ile Glu Asp Val Ile Glu
    210                 215                 220

Val Ser Gly Gly Phe Ser Ile Ala Asp Leu Phe Pro Ser Leu Lys Phe
225                 230                 235                 240

Ile His Val Ile Thr Gly Met Lys Ser Arg Leu Glu Lys Leu His Arg
                245                 250                 255

Ile Thr Asp Gln Val Leu Glu Asp Ile Val Asn Glu His Lys Ala Thr
            260                 265                 270

Arg Ala Ala Ser Lys Asn Gly Gly Gly Asp Asp Asp Lys Lys Glu Ala
        275                 280                 285

Lys Asn Leu Leu Asp Val Leu Leu Asp Leu Gln Glu Asp Gly Ser Leu
    290                 295                 300

Leu Gln Val Pro Leu Thr Asp Asp Ser Ile Lys Ala Ala Ile Leu Glu
305                 310                 315                 320

Met Leu Gly Gly Gly Ser Asp Thr Ser Ala Lys Thr Thr Glu Trp Ala
                325                 330                 335

Met Ser Glu Met Met Arg Tyr Pro Glu Thr Met Lys Lys Ala Gln Glu
            340                 345                 350

Glu Val Arg Gln Ala Phe Gly Asn Ala Gly Lys Ile Asp Glu Ala Arg
        355                 360                 365

Ile His Glu Leu Lys Tyr Leu Arg Ala Val Phe Lys Glu Thr Leu Arg
    370                 375                 380

Leu His Pro Pro Leu Ala Met Ile Pro Arg Glu Cys Arg Gln Lys Thr
385                 390                 395                 400

Lys Ile Asn Gly Tyr Asp Ile Tyr Pro Lys Thr Lys Thr Leu Ile Asn
                405                 410                 415

Val Tyr Ala Ile Gly Arg Asp Pro Asn Val Trp Ser Glu Pro Glu Lys
            420                 425                 430

Phe Tyr Pro Glu Arg His Leu Asp Ser Pro Ile Asp Phe Arg Gly Ser
        435                 440                 445

Asn Phe Glu Leu Ile Pro Phe Gly Ala Gly Lys Arg Ile Cys Pro Gly
    450                 455                 460

Met Thr Leu Ala Ile Thr Thr Val Glu Leu Phe Leu Ala His Leu Leu
465                 470                 475                 480

Tyr Tyr Phe Asp Trp Lys Phe Val Asp Gly Met Thr Ala Asp Thr Leu
                485                 490                 495
```

```
Asp Met Thr Glu Ser Phe Gly Ala Ser Ile Lys Arg Lys Ile Asp Leu
            500                 505                 510

Ala Leu Val Pro Ile Pro Val Ser Pro Leu Pro
        515                 520


<210> SEQ ID NO 37
<211> LENGTH: 506
<212> TYPE: PRT
<213> ORGANISM: Ricinus communis

<400> SEQUENCE: 37

Met Asp Lys Gln Ile Leu Ser Tyr Pro Val Leu Leu Leu Ser Phe Leu
1               5                   10                  15

Leu Phe Ile Leu Met Val Leu Arg Ile Trp Lys Lys Ser Lys Gly Ser
            20                  25                  30

Phe Asn Ser Pro Pro Gly Pro Trp Lys Leu Pro Leu Ile Gly Asn Met
        35                  40                  45

His Gln Leu Ile Thr Pro Leu Pro His His Arg Leu Arg Glu Leu Ala
    50                  55                  60

Lys Thr His Gly Pro Val Met Ser Ile Gln Leu Gly Gln Val Ser Ala
65                  70                  75                  80

Val Val Ile Ser Ser Val Glu Ala Ala Lys Gln Val Leu Lys Thr Gln
                85                  90                  95

Gly Glu Leu Phe Ala Glu Arg Pro Ser Ile Leu Ala Ser Lys Ile Val
            100                 105                 110

Leu Tyr Asn Gly Met Asp Ile Ile Phe Gly Ser Tyr Gly Asp His Trp
        115                 120                 125

Arg Gln Met Arg Lys Ile Cys Thr Phe Glu Leu Leu Ser Pro Lys Arg
    130                 135                 140

Val Gln Ser Phe Ser Ser Val Arg Gln Glu Glu Leu Ser Asn Tyr Val
145                 150                 155                 160

Arg Phe Leu His Ser Asn Ala Gly Ser Pro Val Asn Leu Ser Lys Thr
                165                 170                 175

Leu Phe Ala Leu Thr Asn Ser Val Ile Ala Lys Ile Ala Val Gly Lys
            180                 185                 190

Glu Cys Lys Asn Gln Glu Ala Leu Leu Asn Leu Ile Glu Glu Val Leu
        195                 200                 205

Val Ala Ala Gly Gly Phe Thr Val Ala Asp Ser Phe Pro Ser Tyr Asn
    210                 215                 220

Phe Leu His Val Ile Thr Gly Met Lys Ser Asn Leu Glu Arg Leu His
225                 230                 235                 240

Arg Ile Thr Asp Lys Ile Leu Glu Asp Ile Ile Thr Glu His Lys Ala
                245                 250                 255

Pro Arg Ala Leu Phe Lys Arg Gly Gly Asp Glu Asp Lys Lys Glu Ala
            260                 265                 270

Glu Asn Leu Leu Asp Val Leu Leu Gly Leu Gln Glu His Gly Asn Leu
        275                 280                 285

Lys Val Pro Leu Thr Asn Glu Ser Val Lys Ser Ala Ile Leu Glu Met
    290                 295                 300

Leu Ser Gly Gly Ser Asp Thr Ser Ala Lys Thr Ile Glu Trp Ala Met
305                 310                 315                 320

Ser Glu Leu Met Arg Ser Pro Glu Ala Met Glu Lys Ala Gln Glu Glu
                325                 330                 335

Val Arg Arg Val Phe Gly Glu Leu Gly Lys Ile Glu Glu Ser Arg Leu
```

-continued

```
            340                 345                 350

His Glu Leu Lys Tyr Leu Lys Leu Val Ile Lys Glu Thr Leu Arg Leu
        355                 360                 365

His Pro Ala Leu Ala Leu Ile Pro Arg Glu Cys Met Lys Arg Thr Lys
    370                 375                 380

Ile Asp Gly Tyr Asp Ile Ser Pro Lys Thr Lys Ala Leu Val Asn Val
385                 390                 395                 400

Trp Ala Ile Gly Arg Asp Pro Ser Val Trp Asn Glu Pro Glu Lys Phe
                405                 410                 415

Phe Pro Glu Arg Phe Val Asp Ser Ser Ile Asp Phe Arg Gly Asn Asn
            420                 425                 430

Phe Glu Leu Leu Pro Phe Gly Ser Gly Lys Arg Ile Cys Pro Gly Met
        435                 440                 445

Thr Leu Gly Leu Ala Thr Val Glu Leu Phe Leu Ser Tyr Leu Leu Tyr
    450                 455                 460

Tyr Phe Asp Trp Lys Leu Val Gly Gly Val Pro Leu Asp Met Thr Glu
465                 470                 475                 480

Ala Phe Ala Ala Ser Leu Lys Arg Lys Ile Asp Leu Val Leu Ile Pro
                485                 490                 495

Ile Ser Val Gly Pro Ser Pro Thr Thr Asp
            500                 505


<210> SEQ ID NO 38
<211> LENGTH: 500
<212> TYPE: PRT
<213> ORGANISM: Ricinus communis

<400> SEQUENCE: 38

Met Glu Leu Gln Ile Phe Ser Phe Pro Val Leu Leu Ser Phe Phe Leu
1               5                   10                  15

Phe Ile Phe Met Val Leu Arg Ile Trp Lys Asn Ser Asn Lys Lys Leu
            20                  25                  30

Asn Pro Pro Pro Gly Pro Trp Lys Leu Pro Leu Leu Gly Asn Ile His
        35                  40                  45

Gln Leu Ala Thr Pro Leu Pro His Gln Arg Leu Arg Asp Leu Ala Lys
    50                  55                  60

Ser Phe Gly Pro Val Met Ser Ile Lys Leu Gly Glu Ile Ser Ala Val
65                  70                  75                  80

Ile Ile Ser Ser Ala Glu Ala Ala Gln Glu Val Leu Lys Ser Gln Asp
                85                  90                  95

Val Thr Phe Ala Glu Arg Pro Ala Ser Leu Ala Ser Lys Leu Val Leu
            100                 105                 110

Tyr Asn Arg Asn Asp Ile Val Phe Gly Ala Tyr Gly Pro Gln Trp Arg
        115                 120                 125

Gln Thr Arg Lys Leu Cys Val Leu Glu Leu Leu Ser Ala Lys Arg Ile
    130                 135                 140

Gln Ser Phe Lys Ser Val Arg Glu Glu Glu Val Asp Glu Phe Ala Lys
145                 150                 155                 160

Phe Val Tyr Ser Lys Gly Gly Thr Pro Val Asn Leu Thr Asp Lys Leu
                165                 170                 175

Phe Ala Leu Thr Asn Thr Ile Met Ala Arg Thr Thr Ile Gly Lys Lys
            180                 185                 190

Cys Arg Ser Glu Lys Asp Leu Leu Arg Cys Ile Asp Gly Ile Phe Glu
        195                 200                 205
```

```
Glu Ala Gly Val Phe Asn Leu Ala Asp Ala Phe Pro Ser Phe Thr Leu
    210                 215                 220

Leu Pro Val Ile Thr Gly Ala Lys Phe Arg Leu Glu Lys Leu His Arg
225                 230                 235                 240

Glu Thr Asp Lys Ile Leu Glu Asp Ile Leu Arg Glu His Ile Ala Ser
                245                 250                 255

Lys Ala Ala Ser Asp Lys Asp Thr Arg Asn Leu Leu His Val Leu Leu
            260                 265                 270

Asp Leu Gln Glu Ser Gly Asn Leu Glu Val Pro Ile Thr Asn Asp Ser
        275                 280                 285

Ile Lys Ala Thr Ile Leu Asp Ile Phe Ile Ala Gly Ser Asp Thr Ser
    290                 295                 300

Ala Lys Thr Val Glu Trp Ala Met Ser Glu Leu Met Arg Asn Pro Lys
305                 310                 315                 320

Leu Met Lys Arg Ala Gln Glu Glu Val Arg Gln Val Phe Gly Glu Lys
                325                 330                 335

Gly Phe Val Asp Glu Ala Gly Leu Gln Asp Leu Lys Phe Met Lys Leu
            340                 345                 350

Ile Val Lys Glu Thr Leu Arg Leu His Pro Val Phe Ala Met Phe Pro
        355                 360                 365

Arg Glu Cys Arg Glu Lys Thr Lys Val Asn Gly Tyr Asp Ile Ser Pro
    370                 375                 380

Lys Thr Thr Met Leu Ile Asn Val Trp Ala Ile Gly Arg Asp Pro Asn
385                 390                 395                 400

Val Trp Pro Asp Ala Glu Lys Phe Asn Pro Glu Arg Phe Leu Asp Ser
                405                 410                 415

Ser Ile Asp Tyr Lys Gly Asn Asn Ala Glu Met Ile Pro Phe Gly Ala
            420                 425                 430

Gly Lys Arg Ile Cys Leu Gly Met Thr Leu Gly Thr Leu Ile Leu Glu
        435                 440                 445

His Phe Leu Ala Lys Leu Leu Tyr His Phe Asp Trp Lys Phe Pro Asp
    450                 455                 460

Gly Val Thr Pro Glu Asn Phe Asp Met Thr Glu His Tyr Ser Ala Ser
465                 470                 475                 480

Met Arg Arg Glu Thr Asp Leu Ile Leu Ile Pro Ile Pro Val His Pro
                485                 490                 495

Leu Pro Thr His
            500


<210> SEQ ID NO 39
<211> LENGTH: 500
<212> TYPE: PRT
<213> ORGANISM: Ricinus communis

<400> SEQUENCE: 39

Met Glu Gln Gln Ile Leu Ser Phe Ser Val Leu Ser Cys Leu Ile Leu
1               5                   10                  15

Phe Leu Leu Met Val Ile Asn Ile Leu Lys Asn Tyr Ser Lys Asp Phe
            20                  25                  30

Thr Pro Pro Pro Gly Pro Trp Lys Leu Pro Phe Leu Gly Asn Ile His
        35                  40                  45

Gln Leu Ala Thr Ala Leu Pro His Arg Arg Leu Arg Asp Leu Ala Lys
    50                  55                  60

Thr Tyr Gly Pro Val Met Ser Ile Lys Leu Gly Glu Ile Ser Ser Ile
65                  70                  75                  80
```

```
Val Ile Ser Ser Ala Glu Ala Ala Gln Glu Val Leu Lys Thr Gln Asp
                85                  90                  95

Val Ile Phe Ala Glu Arg Pro Ile Ala Leu Ala Ala Lys Met Val Leu
            100                 105                 110

Tyr Asn Arg Asp Gly Ile Val Phe Gly Ser Tyr Gly Glu Gln Leu Arg
        115                 120                 125

Gln Ser Arg Lys Ile Cys Ile Leu Glu Leu Leu Ser Ala Lys Arg Ile
    130                 135                 140

Gln Ser Phe Lys Ser Val Arg Glu Glu Glu Val Ser Asn Phe Ile Ser
145                 150                 155                 160

Phe Leu Asn Ser Lys Ala Gly Thr Pro Val Asn Leu Thr Asp Lys Leu
                165                 170                 175

Phe Ala Leu Thr Asn Ser Ile Met Ala Arg Thr Ser Ile Gly Lys Lys
            180                 185                 190

Cys Lys Asn Gln Glu Asp Leu Leu Arg Cys Ile Asp Asn Ile Phe Glu
        195                 200                 205

Glu Ala Thr Val Phe Ser Pro Ala Asp Ala Phe Pro Ser Phe Thr Leu
    210                 215                 220

Leu His Val Ile Thr Gly Val Lys Ser Arg Leu Glu Arg Leu His Gln
225                 230                 235                 240

Gln Thr Asp Lys Ile Leu Glu Asp Ile Val Ser Glu His Lys Ala Thr
                245                 250                 255

Met Ala Ala Thr Glu Asn Gly Asp Arg Asn Leu Leu His Val Leu Leu
            260                 265                 270

Asp Leu Gln Lys Asn Gly Asn Leu Gln Val Pro Leu Thr Asn Asn Ile
        275                 280                 285

Ile Lys Ala Ile Ile Leu Thr Ile Phe Ile Gly Gly Ser Asp Thr Ser
    290                 295                 300

Ala Lys Thr Val Glu Trp Val Met Ser Glu Leu Met His Asn Pro Glu
305                 310                 315                 320

Leu Met Lys Lys Ala Gln Glu Glu Val Arg Gln Val Phe Gly Glu Lys
                325                 330                 335

Gly Phe Val Asp Glu Thr Gly Leu His Glu Leu Lys Phe Leu Lys Ser
            340                 345                 350

Val Val Lys Glu Thr Leu Arg Leu His Pro Val Phe Pro Leu Val Pro
        355                 360                 365

Arg Glu Cys Arg Glu Val Thr Lys Val Asn Gly Tyr Asp Ile Tyr Pro
    370                 375                 380

Lys Thr Lys Val Leu Ile Asn Val Trp Ala Ile Gly Arg Asp Pro Asp
385                 390                 395                 400

Ile Trp Ser Asp Ala Glu Lys Phe Asn Pro Glu Arg Phe Leu Glu Ser
                405                 410                 415

Ser Ile Asp Tyr Lys Asp Thr Ser Ser Glu Met Ile Pro Phe Gly Ala
            420                 425                 430

Gly Lys Arg Val Cys Pro Gly Met Ser Leu Gly Leu Leu Ile Leu Glu
        435                 440                 445

Leu Phe Leu Ala Gln Leu Leu Tyr His Phe Asp Trp Lys Leu Pro Asp
    450                 455                 460

Arg Val Thr Pro Glu Asn Phe Asp Met Ser Glu Tyr Tyr Ser Ser Ser
465                 470                 475                 480

Leu Arg Arg Lys His Asp Leu Ile Leu Ile Pro Ile Pro Val Leu Pro
                485                 490                 495
```

```
Leu Pro Ile Glu
            500


<210> SEQ ID NO 40
<211> LENGTH: 504
<212> TYPE: PRT
<213> ORGANISM: Ricinus communis

<400> SEQUENCE: 40

Met Glu Gln Gln Ile Leu Ser Phe Pro Val Leu Leu Ser Phe Phe Leu
1               5                   10                  15

Phe Ile Phe Met Val Leu Lys Ile Arg Lys Lys Tyr Asn Lys Asn Ile
            20                  25                  30

Ser Pro Pro Pro Gly Pro Trp Lys Leu Pro Ile Leu Gly Asn Ile His
        35                  40                  45

Gln Leu Ile Ser Pro Leu Pro His His Arg Leu Arg Asp Leu Ala Lys
    50                  55                  60

Ile Tyr Gly Pro Val Met Ser Ile Lys Leu Gly Glu Val Ser Ala Val
65                  70                  75                  80

Val Ile Ser Ser Ala Glu Ala Ala Lys Glu Val Leu Arg Thr Gln Asp
                85                  90                  95

Val Ser Phe Ala Asp Arg Pro Leu Gly Leu Ser Ala Lys Met Val Leu
            100                 105                 110

Tyr Asn Gly Asn Asp Val Val Phe Gly Ser Tyr Gly Glu Gln Trp Arg
        115                 120                 125

Gln Leu Arg Lys Ile Cys Ile Leu Glu Leu Leu Ser Ala Lys Arg Val
    130                 135                 140

Gln Ser Phe Lys Ser Leu Arg Glu Ala Glu Val Ser Asn Phe Ile Arg
145                 150                 155                 160

Phe Leu Tyr Ser Lys Ala Gly Lys Pro Val Asn Leu Thr Arg Lys Leu
                165                 170                 175

Phe Ala Leu Thr Asn Thr Ile Met Ala Arg Thr Ser Val Gly Lys Gln
            180                 185                 190

Cys Glu Asn Gln Glu Val Leu Leu Thr Val Ile Asp Arg Ile Phe Glu
        195                 200                 205

Val Ser Gly Gly Phe Thr Val Ala Asp Val Phe Pro Ser Phe Thr Leu
    210                 215                 220

Leu His Leu Ile Thr Gly Ile Lys Ser Arg Leu Glu Arg Leu His Gln
225                 230                 235                 240

Asp Thr Asp Gln Ile Leu Glu Asp Ile Ile Asn Glu His Arg Ala Cys
                245                 250                 255

Lys Ala Val Ser Lys Asn Gly Asp Gln Asn Glu Ala Asp Asn Leu Leu
            260                 265                 270

Asp Val Leu Leu Asp Leu Gln Glu Asp Gly Asn Leu Arg Val Pro Leu
        275                 280                 285

Thr Asn Asp Ser Ile Lys Gly Thr Ile Leu Asp Met Phe Ala Gly Gly
    290                 295                 300

Ser Asp Thr Thr Ser Lys Thr Ala Glu Trp Ala Val Ser Glu Leu Met
305                 310                 315                 320

Phe Asn Pro Lys Ala Met Lys Lys Ala Gln Glu Glu Val Arg Arg Val
                325                 330                 335

Phe Gly Gln Lys Gly Ile Val Asp Glu Ser Gly Phe His Glu Leu Lys
            340                 345                 350

Phe Leu Lys Leu Val Ile Lys Glu Thr Leu Arg Leu His Pro Ala Leu
        355                 360                 365
```

```
Pro Leu Ile Pro Arg Glu Cys Met Asn Lys Ser Lys Ile Asn Gly Tyr
    370                 375                 380

Asn Ile Asp Pro Lys Thr Lys Val Leu Ile Asn Val Trp Ala Ile Gly
385                 390                 395                 400

Arg Asp Ser Asn Ile Trp Pro Glu Ala Glu Lys Phe Tyr Pro Glu Arg
                405                 410                 415

Phe Leu Asp Ser Ser Ile Asp Tyr Lys Gly Thr Ser Tyr Glu Phe Ile
            420                 425                 430

Pro Phe Gly Ala Gly Lys Arg Ile Cys Pro Gly Met Met Leu Gly Thr
        435                 440                 445

Thr Asn Leu Glu Leu Phe Leu Ala Gln Leu Leu Tyr His Phe Asp Trp
    450                 455                 460

Gln Phe Pro Asp Gly Val Thr Pro Glu Thr Phe Asp Met Thr Glu Ala
465                 470                 475                 480

Phe Ser Gly Ser Ile Asn Arg Lys Tyr Asp Leu Asn Leu Ile Pro Ile
                485                 490                 495

Pro Phe His Pro Leu Arg Val Glu
            500


<210> SEQ ID NO 41
<211> LENGTH: 494
<212> TYPE: PRT
<213> ORGANISM: Euphorbia peplus

<400> SEQUENCE: 41

Met Asp Leu Glu Met Pro Ser Phe Leu Ile Leu Phe Ser Phe Leu Ile
1               5                   10                  15

Leu Thr Trp Ile Ile Trp Lys Lys Met Asn Ser Asn Ser Val Pro Pro
            20                  25                  30

Pro Gly Pro Trp Lys Leu Pro Leu Leu Gly Asn Ile Leu Gln Leu Arg
        35                  40                  45

Gly Gly Pro Ala Asn His Arg Leu Cys Asp Leu Ala Lys Val Tyr Gly
    50                  55                  60

Pro Val Met Ser Ile Gln Leu Gly Gln Asn Pro Ala Val Val Leu Ser
65                  70                  75                  80

Ser Pro Glu Ala Ala Glu Gln Val Phe Lys Ile Gln Gly Asp Leu Phe
                85                  90                  95

Asn Asn Arg Pro Pro Ala Leu Ser Gly Lys Ile Leu Phe Tyr Asn Asn
            100                 105                 110

Ser Asp Met Thr Phe Thr Pro Tyr Gly Asp His Trp Arg Gln Ile Arg
        115                 120                 125

Lys Ile Thr Val Met Glu Phe Leu Ser Pro Lys Arg Val Leu Ser Phe
    130                 135                 140

Arg Ser Ile Arg Glu Glu Gln Val Ser Asn Phe Ile Lys Phe Leu Arg
145                 150                 155                 160

Thr Lys Gly Gly Ser Ala Ile Asn Phe Pro Lys Ala Leu Ser Glu Leu
                165                 170                 175

Thr Ser Arg Ile Met Leu Ile Thr Leu Leu Gly Asn Lys Asp Glu Asn
            180                 185                 190

Glu Glu Ile Val Leu Pro Ala Ile Glu Arg Val Ile Glu Thr Ala Asn
        195                 200                 205

Lys Gly Ala Ala Ser Asp Thr Phe Pro Thr Leu Lys Phe Phe Leu Asp
    210                 215                 220

Phe Leu Thr Gly Asp Lys Ser Arg Met Glu Lys Val Leu Gln Glu Thr
```

225 230 235 240

Asp Ile Ile Leu Glu Ala Ile Ile Asn Glu His Lys Lys Lys Gly Thr
245 250 255

Ser Glu His Asn Tyr Leu Asp Phe Leu Leu Asp Lys Gln Lys Lys Gly
260 265 270

Asp Leu Gln Leu Pro Leu Thr Asn Glu Ala Ile Lys Ala Asn Leu Met
275 280 285

Ala Met Tyr Ala Gly Gly Ser Glu Thr Ser Ser Lys Leu Ile Glu Trp
290 295 300

Thr Phe Ala Glu Met Met Lys Asn Pro Glu Thr Met Arg Lys Ala Gln
305 310 315 320

Glu Glu Val Arg Arg Val Phe Gly Asp Lys Gly Lys Val Glu Glu Ser
325 330 335

Arg Ile Gln Glu Leu Lys Tyr Leu Lys Leu Val Leu Lys Glu Ser Phe
340 345 350

Arg Ile His Pro Pro Ser Thr Leu Ile Thr Arg Val Cys Gln Glu Arg
355 360 365

Thr Lys Ile Asn Gly Tyr Asp Ile His Pro Lys Thr Thr Ile Leu Ile
370 375 380

Asn Val Trp Thr Met Gly Arg Asp Pro Asn Leu Trp Lys Glu Pro Glu
385 390 395 400

Lys Phe His Pro Glu Arg Phe Glu Asp Ser Lys Ile Asp Phe Arg Gly
405 410 415

Ala Asn Met Glu Leu Thr Pro Phe Gly Val Gly Lys Arg Met Cys Pro
420 425 430

Gly Ile Thr Leu Ser Thr Thr Tyr Val Glu Phe Leu Leu Ala Asn Leu
435 440 445

Leu Tyr His Phe Asp Trp Lys Leu Pro Asp Gly Val Thr Pro Ala Thr
450 455 460

Leu Asp Met Thr Glu Thr Leu Arg Gly Thr Leu Lys Lys Val Gln Asp
465 470 475 480

Leu Ile Leu Ile Pro Ile Pro Phe Ser Pro His Gln Ile Ala
485 490

<210> SEQ ID NO 42
<211> LENGTH: 503
<212> TYPE: PRT
<213> ORGANISM: Euphorbia peplus

<400> SEQUENCE: 42

Met Glu Phe Thr Leu Ser Leu Lys Lys Met Glu Leu Gln Ile Leu Ser
1 5 10 15

Phe Pro Ile Leu Phe Pro Phe Leu Leu Phe Ile Leu Thr Phe Leu Thr
20 25 30

Ile Ile Arg Arg Lys Lys Gln Asn Gln Asp Cys Asn Phe Pro Pro Gly
35 40 45

Pro Trp Gln Phe Pro Ile Ile Gly Asn Ile Pro Gln Leu Leu Gly Gly
50 55 60

Leu Phe His His Arg Leu Ser Asp Leu Ala Lys Ile His Gly Pro Ile
65 70 75 80

Met Ser Ile Gln Gln Gly Gln Ile Pro Ala Val Val Ile Thr Ser Val
85 90 95

Glu Leu Ala Lys Glu Val Leu Lys Thr Gln Gly Glu Ile Phe Ala Gly
100 105 110

-continued

```
Arg Pro Gln Ala Pro Ala Gly Asp Val Leu Tyr Tyr Asp Cys Lys Asp
        115                 120                 125

Ile Val Phe Ala Pro Tyr Gly Asp His Trp Arg Gln Met Arg Lys Ile
    130                 135                 140

Cys Thr Leu Glu Phe Leu Ser Leu Lys Arg Val Gln Ser Phe Arg Ser
145                 150                 155                 160

Leu Arg Glu Glu Asn Val Ser Gly Phe Ile Lys Phe Leu Ser Thr Lys
                165                 170                 175

Ala Asn Ser Ser Val Asn Leu Thr Lys Ser Val Gly Asn Leu Thr Ser
            180                 185                 190

Ser Ile Met Leu Ile Lys Thr Tyr Gly Lys Cys Asp Glu Lys Leu Leu
        195                 200                 205

Ala Met Leu Glu Lys Val Lys Gln Ala Val Leu Glu Thr Ser Ser Gly
    210                 215                 220

Thr Asp Leu Phe Pro Ser Leu Lys Phe Ile Gln Tyr Ile Asn Gly Glu
225                 230                 235                 240

Lys Ser Arg Met Ala Arg Val Gln Lys Glu Met Asp Lys Met Leu Glu
                245                 250                 255

Gln Ile Ile Lys Glu His Lys Val Gln Tyr Lys Phe Gly Asp Asn Asn
            260                 265                 270

Leu Leu Gln Val Leu Leu Asp Gln Gln Gln Asn Gly Asp Leu Glu Leu
        275                 280                 285

Pro Leu Thr Asn Glu Ile Ile Lys Ala Asn Ile Met Glu Ile Phe Phe
    290                 295                 300

Gly Gly Ser His Thr Ser Ser Lys Thr Val Glu Trp Ala Met Ser Glu
305                 310                 315                 320

Leu Met Lys Asn Pro Glu Ser Met Thr Lys Ala Gln Ala Glu Val Arg
                325                 330                 335

Gln Val Phe Gly Glu Thr Gly Asn Val Glu Glu Ser Arg Met Gln Glu
            340                 345                 350

Val Lys Tyr Leu Lys Ser Val Ile Lys Glu Thr Leu Arg Leu His Pro
        355                 360                 365

Pro Ala Thr Phe Val Thr Arg Glu Cys Arg Gln Lys Thr Lys Val Asn
    370                 375                 380

Gly Tyr Asp Ile Tyr Pro Lys Thr Val Val His Val Asn Thr Tyr Ala
385                 390                 395                 400

Ile Cys Arg Asp Pro Asp Val Trp Val Glu Pro Glu Lys Phe Tyr Pro
                405                 410                 415

Glu Arg Phe Glu Glu Asn Gln Ile Asp Tyr Lys Gly Ala His Met Glu
            420                 425                 430

Leu Ile Pro Phe Gly Ala Gly Lys Arg Ile Cys Pro Gly Ile Ser Leu
        435                 440                 445

Ala Thr Thr Tyr Val Glu Val Leu Leu Ala Asn Leu Leu Tyr His Phe
    450                 455                 460

Asp Trp Lys Leu Pro Tyr Gly Met Thr Pro Ala Asn Leu Asp Met Thr
465                 470                 475                 480

Glu Met His Cys Gly Ala Leu Ala Arg Lys His Asp Leu Cys Leu Ile
                485                 490                 495

Pro Ile Pro Phe Ser Lys Ile
            500
```

<210> SEQ ID NO 43
<211> LENGTH: 497
<212> TYPE: PRT

<213> ORGANISM: Euphorbia peplus

<400> SEQUENCE: 43

```
Met Lys Met Leu Glu Gln Ile Pro Ser Leu Pro Ile Ile Phe Pro Leu
1               5                   10                  15

Ile Leu Phe Ile Phe Met Leu Ile Lys Leu Trp Gln Lys Lys Asn His
            20                  25                  30

Asn Ser Ile Arg Pro Pro Gly Pro Arg Lys Tyr Pro Phe Ile Gly Asn
        35                  40                  45

Leu Pro Gln Leu Leu Gly Ala Pro Val His Gln Arg Leu Ala Asp Leu
    50                  55                  60

Ala Lys Thr Tyr Gly Pro Val Met Ser Ile Gln Gln Gly Gln Ile Pro
65                  70                  75                  80

Ser Val Val Leu Ser Ser Val Glu Thr Ala Lys Glu Val Leu Lys Ile
                85                  90                  95

Gln Gly Glu Glu Phe Ala Gly Arg Pro Ser Thr Met Ala Leu Asp Ile
            100                 105                 110

Thr Phe Tyr Asp Ala Gln Asp Ile Ala Tyr Thr Glu Tyr Gly Asp Tyr
        115                 120                 125

Trp Arg Gln Met Lys Lys Ile Ser Thr Leu Glu Phe Leu Ser Ala Lys
    130                 135                 140

Arg Val His Ser Phe Lys Pro Val Arg Glu Glu Arg Ile Ser Ile Phe
145                 150                 155                 160

Leu Asp Ser Leu Arg Ser Lys Gly Arg Ser Pro Val Asn Leu Thr Arg
                165                 170                 175

Thr Ile Tyr Gly Leu Thr Asn Ser Ile Ile Gln Ile Thr Ala Phe Gly
            180                 185                 190

Lys Asn Cys Lys Thr Arg Glu Lys Leu Asn Leu Asp Lys Ile Arg Glu
        195                 200                 205

Ala Val Val Asp Gly Thr Ile Ala Asp Leu Phe Pro Arg Phe Lys Phe
    210                 215                 220

Ile Ala Ser Leu Ser Gly Ala Lys Ser Arg Met Met Arg Ala His Lys
225                 230                 235                 240

Glu Ile Asp Val Val Leu Asp Glu Ile Leu Glu Glu His Lys Ala Asn
                245                 250                 255

Lys Ser Thr Ile Gly Asn Asn Leu Met Gln Val Leu Leu Asp Phe Gln
            260                 265                 270

Lys Asn Gly Gly Leu Gln Val Pro Leu Thr Thr Asp Gln Ile Lys Ala
        275                 280                 285

Asn Met Leu Glu Met Phe Leu Ser Gly Ser His Thr Ser Ser Lys Ile
    290                 295                 300

Thr Glu Trp Thr Met Ala Glu Leu Met Arg Ala Pro Glu Thr Met Arg
305                 310                 315                 320

Lys Ala Gln Glu Glu Val Arg Arg Val Phe Ser Glu Ile Gly Arg Val
                325                 330                 335

Asp Glu Ser Arg Ile His Glu Cys Lys Tyr Val Lys Asn Val Leu Lys
            340                 345                 350

Glu Ala Phe Arg Leu His Pro Pro Gly Pro Met Val Val Arg Gln Cys
        355                 360                 365

Arg Glu Ile Thr Lys Val Asn Gly Tyr Glu Ile Leu Pro Gly Thr Thr
    370                 375                 380

Val Phe Ile Asn Val Trp Ala Ile Gly Arg Asp Pro Glu Val Trp Thr
385                 390                 395                 400
```

```
Glu Pro Glu Lys Phe Asn Pro Asp Arg Phe Glu Asp Ser Glu Ile Asp
                405                 410                 415

Tyr Arg Gly Ala His Met Glu Leu Ile Pro Phe Gly Ala Gly Lys Arg
            420                 425                 430

Ile Cys Pro Gly Leu Thr Leu Ala Val Val Tyr Val Glu Leu Leu Leu
        435                 440                 445

Ala Asn Leu Leu Tyr His Phe Asp Trp Glu Phe Pro Asp Gly Val Thr
    450                 455                 460

Gln Lys Thr Leu Asp Met Thr Glu Phe Phe Arg Gly Thr Leu Asn Arg
465                 470                 475                 480

Lys Glu Asp Leu Tyr Leu Ile Pro Val Pro Ser Ser Ser Leu Pro Lys
                485                 490                 495

Asn


<210> SEQ ID NO 44
<211> LENGTH: 503
<212> TYPE: PRT
<213> ORGANISM: Jatropha curcas

<400> SEQUENCE: 44

Met Glu His Gln Ile Leu Ser Phe Pro Val Leu Phe Ser Leu Leu Leu
1               5                   10                  15

Phe Ile Leu Val Leu Leu Lys Val Ser Lys Lys Leu Tyr Lys His Asp
            20                  25                  30

Ser Lys Pro Pro Pro Gly Pro Trp Lys Leu Pro Phe Ile Gly Asn Leu
        35                  40                  45

Ile Gln Leu Val Gly Asp Thr Pro His Arg Arg Leu Thr Ala Leu Ala
    50                  55                  60

Lys Thr Tyr Gly Pro Val Met Gly Val Gln Leu Gly Gln Val Pro Phe
65                  70                  75                  80

Leu Val Val Ser Ser Pro Glu Thr Ala Lys Glu Val Met Lys Ile Gln
                85                  90                  95

Asp Pro Val Phe Ala Glu Arg Pro Leu Val Leu Ala Gly Glu Ile Val
            100                 105                 110

Leu Tyr Asn Arg Asn Asp Ile Val Phe Gly Ser Tyr Gly Asp Gln Trp
        115                 120                 125

Arg Gln Met Arg Lys Phe Cys Thr Leu Glu Leu Leu Ser Thr Lys Arg
    130                 135                 140

Val Gln Ser Phe Arg Pro Val Arg Glu Glu Glu Val Ala Ser Phe Val
145                 150                 155                 160

Lys Leu Met Arg Thr Lys Lys Gly Thr Pro Val Asn Leu Thr His Ala
                165                 170                 175

Leu Phe Ala Leu Thr Asn Ser Ile Val Ala Arg Asn Ala Val Gly His
            180                 185                 190

Lys Ser Lys Asn Gln Glu Ala Leu Leu Glu Val Ile Asp Asp Ile Val
        195                 200                 205

Val Ser Gly Gly Gly Val Ser Ile Val Asp Ile Phe Pro Ser Leu Gln
    210                 215                 220

Trp Leu Pro Thr Ala Lys Arg Glu Arg Ser Arg Ile Trp Lys Leu His
225                 230                 235                 240

Gln Asn Thr Asp Glu Ile Leu Glu Asp Ile Leu Gln Glu His Arg Ala
                245                 250                 255

Lys Arg Gln Ala Thr Ala Ser Lys Asn Trp Asp Arg Ser Glu Ala Asp
            260                 265                 270
```

```
Asn Leu Leu Asp Val Leu Leu Asp Leu Gln Gln Ser Gly Asn Leu Asp
        275                 280                 285

Val Pro Leu Thr Asp Val Ala Ile Lys Ala Ala Ile Ile Asp Met Phe
    290                 295                 300

Gly Ala Gly Ser Asp Thr Ser Ser Lys Thr Ala Glu Trp Ala Met Ala
305                 310                 315                 320

Glu Leu Met Arg Asn Pro Glu Val Met Lys Lys Ala Gln Glu Glu Leu
                325                 330                 335

Arg Asn Phe Phe Gly Glu Asn Gly Lys Val Glu Glu Ala Lys Leu His
            340                 345                 350

Glu Leu Lys Trp Ile Lys Leu Ile Ile Lys Glu Thr Leu Arg Leu His
        355                 360                 365

Pro Ala Val Ala Val Ile Pro Arg Val Cys Arg Glu Lys Thr Lys Val
    370                 375                 380

Tyr Gly Tyr Asp Val Glu Pro Gly Thr Arg Val Phe Ile Asn Val Trp
385                 390                 395                 400

Ser Ile Gly Arg Asp Pro Lys Val Trp Ser Glu Ala Glu Arg Phe Lys
                405                 410                 415

Pro Glu Arg Phe Ile Asp Ser Ala Ile Asp Tyr Arg Gly Leu Asn Phe
            420                 425                 430

Glu Leu Ile Pro Phe Gly Ala Gly Lys Arg Ile Cys Pro Gly Met Thr
        435                 440                 445

Leu Gly Met Ala Asn Leu Glu Ile Phe Leu Ala Asn Leu Leu Tyr His
    450                 455                 460

Phe Asp Trp Lys Phe Pro Lys Gly Val Thr Ala Glu Asn Leu Asp Met
465                 470                 475                 480

Asn Glu Ala Phe Gly Gly Ala Val Lys Arg Lys Val Asp Leu Glu Leu
                485                 490                 495

Ile Pro Ile Pro Phe Arg Pro
            500


<210> SEQ ID NO 45
<211> LENGTH: 503
<212> TYPE: PRT
<213> ORGANISM: Jatropha curcas

<400> SEQUENCE: 45

Met Glu Gln Gln Ile Leu Ser Phe Pro Val Leu Phe Ser Phe Leu Leu
1               5                   10                  15

Phe Leu Leu Val Leu Leu Lys Val Ser Lys Lys Leu Ser Lys His Asp
            20                  25                  30

Ser Asn Ser Pro Pro Gly Pro Trp Lys Leu Pro Phe Leu Gly Asn Ile
        35                  40                  45

Leu Gln Leu Ala Gly Asp Leu Pro His Arg Arg Ile Thr Glu Leu Ala
    50                  55                  60

Lys Lys Tyr Gly Pro Val Met Ser Ile Lys Leu Gly Gln His Pro Tyr
65                  70                  75                  80

Leu Val Val Ser Ser Pro Glu Thr Ala Lys Glu Val Met Arg Thr Gln
                85                  90                  95

Asp Pro Ile Phe Ala Asp Arg Pro Leu Val Leu Ala Gly Glu Leu Val
            100                 105                 110

Leu Tyr Asn Arg Asn Asp Ile Gly Phe Gly Leu Tyr Gly Asp Gln Trp
        115                 120                 125

Arg Gln Met Arg Lys Phe Cys Ala Leu Glu Leu Leu Ser Thr Lys Arg
    130                 135                 140
```

```
Val Gln Ser Phe Arg Ser Val Arg Glu Glu Glu Ile Ala Glu Phe Val
145                 150                 155                 160

Lys Ser Leu Arg Ser Lys Glu Gly Ser Ser Val Asn Leu Ser His Thr
                165                 170                 175

Leu Phe Ala Leu Thr Asn Ser Ile Ile Ala Arg Asn Thr Val Gly His
            180                 185                 190

Lys Ser Lys Asn Gln Glu Ala Leu Leu Lys Ile Ile Asp Asp Ile Val
        195                 200                 205

Glu Ser Leu Gly Gly Leu Ser Thr Val Asp Ile Phe Pro Ser Leu Lys
    210                 215                 220

Trp Leu Pro Ser Val Lys Arg Glu Arg Ser Arg Ile Trp Lys Leu His
225                 230                 235                 240

Cys Glu Thr Asp Glu Ile Leu Glu Gly Ile Leu Glu Glu His Lys Ala
                245                 250                 255

Asn Arg Gln Ala Ala Ala Phe Lys Asn Asp Asp Gly Ser Gln Ala Asp
            260                 265                 270

Asn Leu Leu Asp Val Leu Leu Asp Leu Gln Gln Asn Gly Asn Leu Glu
        275                 280                 285

Val Pro Leu Thr Asp Val Asn Ile Lys Ala Val Ile Leu Gly Met Phe
    290                 295                 300

Gly Ala Gly Ser Asp Thr Ser Ser Lys Thr Thr Glu Trp Ala Met Ala
305                 310                 315                 320

Glu Leu Met Lys Asn Pro Glu Ile Met Lys Lys Ala Gln Glu Glu Leu
                325                 330                 335

Arg Ser Leu Phe Gly Glu Ser Gly Tyr Val Asp Glu Ala Lys Leu His
            340                 345                 350

Glu Ile Lys Trp Leu Lys Leu Ile Ile Asn Glu Thr Leu Arg Leu His
        355                 360                 365

Pro Ala Val Thr Leu Ile Pro Arg Leu Cys Arg Glu Lys Thr Lys Val
    370                 375                 380

Ser Gly Tyr Asp Val Tyr Pro Asn Thr Arg Val Phe Ile Asn Thr Trp
385                 390                 395                 400

Ala Ile Gly Arg Asp Pro Thr Ile Trp Ser Glu Pro Glu Lys Phe Val
                405                 410                 415

Pro Glu Arg Phe Ile Asp Ser Ser Ile Asp Tyr Arg Gly Asn His Phe
            420                 425                 430

Glu Tyr Thr Pro Phe Gly Ala Gly Arg Arg Ile Cys Pro Gly Met Ala
        435                 440                 445

Phe Gly Met Val Asn Leu Glu Ile Phe Leu Ala Asn Leu Leu Tyr His
    450                 455                 460

Phe Asp Trp Lys Leu Pro Lys Gly Ile Thr Ser Glu Asn Leu Asp Met
465                 470                 475                 480

Thr Glu Asn Phe Gly Gly Val Ile Lys Arg Lys Gln Asp Leu Glu Leu
                485                 490                 495

Ile Pro Ala Pro Phe Arg Pro
            500
```

<210> SEQ ID NO 46
<211> LENGTH: 502
<212> TYPE: PRT
<213> ORGANISM: Jatropha curcas

<400> SEQUENCE: 46

```
Met Glu Gln Gln Ile Leu Ser Val Ser Val Leu Ser Ser Phe Val Leu
```

-continued

```
1               5                   10                  15

Phe Leu Phe Val Leu Leu Lys Val Ser Lys Lys Leu Tyr Lys His Asp
            20                  25                  30

Ser Asn Pro Pro Pro Gly Pro Trp Lys Leu Pro Phe Leu Gly Asn Ile
        35                  40                  45

Leu Gln Leu Ala Gly Asp Ala Pro His His Arg Phe Ala Glu Leu Ala
    50                  55                  60

Arg Thr Tyr Gly Pro Val Met Gly Ile Lys Leu Gly Glu Ile Pro Phe
65                  70                  75                  80

Leu Val Val Ser Ser Pro Glu Ala Ala Lys Glu Val Met Lys Ile Gln
                85                  90                  95

Asp Pro Ile Phe Ala Glu Arg Ala Leu Val Phe Ala Asn Asp Val Leu
            100                 105                 110

Asn Tyr Asn Arg Asn Val Met Val Phe Gly Ser Tyr Gly Tyr Gln Trp
        115                 120                 125

Arg Gln Leu Arg Lys Phe Cys Thr Leu Ala Leu Leu Ser Ala Lys Arg
    130                 135                 140

Val Gln Ser Phe Gln Ser Val Arg Lys Glu Glu Met Ala Asp Phe Val
145                 150                 155                 160

Asn Phe Leu Arg Ser Lys Glu Gly Ser Ser Val Asn Leu Thr His Thr
                165                 170                 175

Ile Phe Ala Phe Thr Asn Ser Ile Ile Ala Arg Asn Ala Val Gly His
            180                 185                 190

Lys Thr Lys Asn Gln Glu Thr Leu Leu Thr Cys Ile Asp Gly Ile Ile
        195                 200                 205

Tyr Thr Gly Gly Val Asn Ile Ala Asp Val Phe Pro Ser Leu Lys Trp
    210                 215                 220

Leu Pro Ser Val Lys Arg Glu Lys Ser Arg Val Met Lys Leu His Tyr
225                 230                 235                 240

Glu Thr Asp Lys Ile Leu Glu Asp Ile Leu Gln Glu His Lys Ala Asn
                245                 250                 255

Lys Gln Ala Trp Val Ser Glu Asp Gly Asp Gly Arg Lys Ala Gly Asn
            260                 265                 270

Phe Val Asp Val Leu Leu Asp Leu Gln Gln Ser Gly Asn Leu Asp Phe
        275                 280                 285

Pro Leu Thr Asp Val Thr Ile Lys Ala Ser Thr Ile Asp Ala Phe Val
    290                 295                 300

Gly Gly Ser Asp Thr Ser Ser Lys Thr Thr Glu Trp Ala Met Ala Glu
305                 310                 315                 320

Leu Met Arg Lys Pro Glu Ile Met Lys Lys Ala Gln Glu Glu Leu Arg
                325                 330                 335

Ser Val Phe Gly Glu Lys Gly Tyr Ile Glu Glu Ala Lys Leu Gln Glu
            340                 345                 350

Leu Lys Trp Leu Lys Leu Ile Ile Lys Glu Thr Met Arg Leu His Pro
        355                 360                 365

Val Leu Ser Leu Leu Pro Arg Val Cys Lys Gln Lys Thr Lys Val Ser
    370                 375                 380

Gly Tyr Asp Val Tyr Pro Gly Thr Gln Val Leu Val Asn Val Trp Ala
385                 390                 395                 400

Leu Gly Arg Asp Pro Lys His Trp Ser Glu Pro Glu Lys Phe Asn Pro
                405                 410                 415

Glu Arg Phe Ile Asp Ser Ser Ile Asp Tyr Leu Gly Asn His Phe Glu
            420                 425                 430
```

```
Tyr Leu Pro Phe Gly Ala Gly Lys Arg Val Cys Pro Gly Ile Ala Leu
        435                 440                 445

Gly Met Val His Met Glu Asn Phe Leu Ala Asn Leu Leu Phe His Phe
    450                 455                 460

Asp Trp Lys Phe Pro Lys Gly Ile Thr Ala Glu Asn Leu Asp Met Thr
465                 470                 475                 480

Asp Ala Phe Gly Gly Val Met Lys Arg Lys Val Asp Leu Glu Leu Ile
                485                 490                 495

Pro Ile Pro Tyr His Pro
            500


<210> SEQ ID NO 47
<211> LENGTH: 503
<212> TYPE: PRT
<213> ORGANISM: Jatropha curcas

<400> SEQUENCE: 47

Met Glu His Gln Ile Leu Ser Phe Pro Ala Leu Phe Ser Phe Leu Leu
1               5                   10                  15

Phe Leu Leu Val Leu Leu Lys Val Ser Lys Lys Leu Tyr Lys His Asp
            20                  25                  30

Ser Asn Pro Pro Pro Gly Pro Trp Lys Leu Pro Phe Leu Gly Asn Ile
        35                  40                  45

Leu Gln Leu Ala Gly Asp Thr Phe His Arg Arg Leu Thr Glu Leu Ala
    50                  55                  60

Lys Thr His Gly Pro Val Met Ser Ile Asn Val Gly Gln Ile Pro Tyr
65                  70                  75                  80

Val Val Val Ser Ser Pro Glu Thr Ala Lys Glu Val Met Lys Ile Gln
                85                  90                  95

Asp Pro Val Phe Ala Asp His Pro Val Val Leu Ala Ala Glu Val Ile
            100                 105                 110

Leu Tyr Ser Pro Tyr Asp Ile Phe Phe Ala Pro Tyr Gly Asp His Leu
        115                 120                 125

Lys Gln Met Arg Lys Phe Cys Thr Val Glu Leu Leu Ser Thr Lys Arg
    130                 135                 140

Val Gln Ser Phe Arg Ser Val Arg Glu Glu Glu Val Ala Asp Phe Val
145                 150                 155                 160

Lys Phe Leu Arg Ser Lys Glu Gly Ser Ser Val Asn Leu Thr His Thr
                165                 170                 175

Leu Phe Ala Leu Thr Asn Ser Ile Val Ala Arg Thr Ala Val Gly His
            180                 185                 190

Arg Ser Lys Asn Gln Glu Gly Leu Leu Lys Val Ile Asp Glu Ala Val
        195                 200                 205

Leu Ala Ser Ser Gly Val Asn Ile Ala Asp Ile Phe Pro Ser Leu Gln
    210                 215                 220

Trp Leu Pro Ser Val Lys Arg Glu Arg Ser Arg Ile Trp Lys Thr His
225                 230                 235                 240

Arg Glu Thr Asp Lys Ile Leu Glu Asp Val Leu Gln Glu His Arg Ala
                245                 250                 255

Asn Arg Lys Ala Ala Val Pro Lys Asn Gly Asp Gln Ser Gln Ala Asp
            260                 265                 270

Asn Leu Leu Asp Val Leu Leu Asp Leu Gln Glu Ser Gly Asn Leu Asp
        275                 280                 285

Val Pro Leu Pro Asp Ala Ala Ile Lys Gly Thr Ile Met Glu Met Phe
```

```
    290                 295                 300

Gly Ala Gly Ser Asp Thr Ser Ser Lys Thr Val Glu Trp Ala Met Ala
305                 310                 315                 320

Glu Leu Met Arg Asn Pro Glu Val Met Arg Lys Ala Gln Glu Glu Leu
                325                 330                 335

Arg Ser Phe Phe Gly Glu Asn Gly Glu Val Glu Asp Ala Lys Ile Gln
            340                 345                 350

Glu Leu Lys Cys Leu Lys Leu Ile Ile Lys Glu Thr Leu Arg Leu His
        355                 360                 365

Pro Pro Gly Ala Val Ile Pro Arg Leu Cys Arg Glu Arg Thr Lys Val
    370                 375                 380

Ala Gly Tyr Asp Ile Tyr Pro Asn Thr Lys Ile Phe Val Asn Thr Trp
385                 390                 395                 400

Ala Ile Gly Arg Asp Pro Glu Ile Trp Ser Glu Ala Glu Lys Phe Asn
                405                 410                 415

Pro Asp Arg Phe Ile Asp Ser Ser Ile Asp Tyr Lys Gly Asn Asn Phe
            420                 425                 430

Glu Leu Ile Pro Phe Gly Ala Gly Arg Arg Ile Cys Pro Gly Ile Thr
        435                 440                 445

Leu Ala Ser Ala Asn Met Glu Leu Phe Leu Ala Asn Leu Leu Tyr His
    450                 455                 460

Phe Asp Trp Lys Phe Pro Gln Gly Ile Thr Ala Glu Asn Leu Asp Met
465                 470                 475                 480

Asn Glu Cys Phe Gly Gly Ala Val Lys Arg Lys Val Asp Leu Glu Leu
                485                 490                 495

Ile Pro Ile Pro Phe Arg Thr
            500


<210> SEQ ID NO 48
<211> LENGTH: 499
<212> TYPE: PRT
<213> ORGANISM: Jatropha curcas

<400> SEQUENCE: 48

Met Leu Ser Phe Pro Val Ile Phe Ser Phe Leu Leu Phe Leu Leu Val
1               5                   10                  15

Leu Leu Lys Val Ser Lys Lys Leu Cys Lys Asp Asn Ser Ile Pro Pro
            20                  25                  30

Pro Gly Pro Trp Gln Leu Pro Phe Leu Gly Asn Ile Phe Gln Leu Ala
        35                  40                  45

Gly Tyr Gln Phe His Ile Arg Leu Ser Glu Leu Gly Gln Thr Tyr Gly
    50                  55                  60

Pro Val Met Gly Ile Lys Val Gly Gln Val Pro Phe Leu Ile Val Ser
65                  70                  75                  80

Ser Pro Glu Met Ala Lys Glu Val Leu Lys Val Gln Asp Pro Thr Phe
                85                  90                  95

Val Asp Arg Pro Val Val Leu Ala Ala Glu Leu Val Met Tyr Gly Gly
            100                 105                 110

His Asp Ile Val Tyr Ala Pro Tyr Gly Asp Gln Trp Arg Gln Met Arg
        115                 120                 125

Lys Phe Cys Thr Leu Glu Leu Leu Ser Thr Lys Arg Val Gln Ser Phe
    130                 135                 140

Arg Ser Val Arg Glu Glu Glu Ala Gly Glu Phe Val Lys Phe Leu Leu
145                 150                 155                 160
```

-continued

```
Ser Lys Glu Gly Ser Ser Val Asn Leu Thr His Ala Leu Tyr Ala Leu
                165                 170                 175

Ser Asn Ser Met Val Ala Arg Ser Thr Val Gly His Lys Thr Lys Asn
            180                 185                 190

Gln Glu Ala Leu Leu Asn Val Ile Asp Asp Thr Val Ser Thr Ala Ala
        195                 200                 205

Gly Thr Asn Ile Ala Asp Ile Phe Pro Ser Leu Lys Trp Leu Pro Thr
    210                 215                 220

Val Lys Arg Gln Met Ser Arg Ile Trp Lys Ser His Cys Gln Thr Asp
225                 230                 235                 240

Glu Ile Leu Glu Gly Ile Leu Arg Glu His Arg Ala Lys Arg Gln Thr
                245                 250                 255

Ala Ala Ser Lys Asn Gly Asp Arg Ala Glu Ala Asp Asn Leu Leu Asp
            260                 265                 270

Val Leu Leu Asp Leu Gln Gln Arg Gly Asp Leu Asp Val Pro Leu Thr
        275                 280                 285

Asp Ile Asn Ile Lys Gly Ala Ile Leu Glu Met Phe Gly Ala Gly Ser
    290                 295                 300

Asp Thr Ser Thr Lys Thr Leu Glu Trp Ala Met Ser Glu Leu Met Arg
305                 310                 315                 320

Asn Pro Lys Met Met Lys Lys Val Gln Gln Glu Leu Arg Ser Phe Phe
                325                 330                 335

Gly Glu Asn Gly Lys Val Glu Glu Ala Lys Leu Gln Glu Leu Lys Trp
            340                 345                 350

Leu Lys Leu Ile Ile Lys Glu Thr Leu Arg Leu His Pro Pro Ile Ala
        355                 360                 365

Val Ile Pro Arg Leu Cys Arg Glu Arg Thr Lys Val Cys Gly Tyr Asp
    370                 375                 380

Val Tyr Pro Asn Thr Arg Val Phe Val Asn Val Trp Ala Met Gly Arg
385                 390                 395                 400

Asp Pro Lys Ile Trp Asn Glu Ala Glu Lys Phe Asn Pro Glu Arg Phe
                405                 410                 415

Ile Asp Ser Ser Ile Asp Tyr Arg Gly Asn Asn Phe Glu Leu Ile Pro
            420                 425                 430

Phe Gly Ala Gly Lys Arg Ile Cys Pro Gly Ile Thr Leu Ala Ile Val
        435                 440                 445

His Val Glu Thr Val Leu Ala Asn Leu Leu Tyr His Phe Asp Trp Lys
    450                 455                 460

Phe Pro Glu Gly Val Thr Ala Glu Asn Phe Asp Met Asn Glu Thr Phe
465                 470                 475                 480

Ala Gly Ile Ile Arg Arg Lys Val Asp Leu Glu Leu Ile Pro Val Ala
                485                 490                 495

Phe Arg Pro
```

<210> SEQ ID NO 49
<211> LENGTH: 495
<212> TYPE: PRT
<213> ORGANISM: Jatropha curcas

<400> SEQUENCE: 49

```
Met Asp His Arg Ile Leu Ser Phe Pro Phe Leu Met Leu Ser Leu Leu
1               5                   10                  15

Leu Pro Phe Val Phe Glu Leu Leu Lys Ile Trp Lys Lys Ser Asn Asn
            20                  25                  30
```

-continued

```
Asn Pro Pro Pro Gly Pro Trp Arg Leu Pro Leu Ile Gly Asn Ile His
        35                  40                  45

Gln Leu Gly Gly Arg His Gln Pro His Leu Arg Leu Thr Asp Leu Ala
    50                  55                  60

Arg Thr Tyr Gly Pro Val Met Arg Leu Gln Leu Gly Gln Ile Glu Ala
65                  70                  75                  80

Val Val Ile Ser Ser Ala Glu Thr Ala Lys Gln Val Met Lys Thr Gln
                85                  90                  95

Glu Ser Gln Phe Leu Gly Arg Pro Ser Leu Leu Ala Ala Asp Ile Met
            100                 105                 110

Leu Tyr Asn Arg Thr Asp Ile Ser Phe Ala Pro Tyr Gly Asp Tyr Trp
        115                 120                 125

Arg Gln Met Lys Lys Ile Ala Val Val Glu Leu Leu Ser Ala Lys Arg
    130                 135                 140

Val Gln Ala Tyr Lys Ser Val Met Asp Glu Glu Val Ser Asn Phe Ile
145                 150                 155                 160

Asn Phe Leu Tyr Ser Lys Ala Gly Ser Pro Val Asn Leu Thr Lys Thr
                165                 170                 175

Phe Tyr Ser Leu Gly Asn Gly Ile Ile Ala Lys Thr Ser Ile Gly Lys
            180                 185                 190

Lys Phe Lys Lys Gln Glu Thr Phe Leu Lys Val Val Asp Lys Ala Ile
        195                 200                 205

Arg Val Ala Gly Gly Phe Ser Val Gly Asp Ala Phe Pro Ser Phe Lys
    210                 215                 220

Leu Ile His Leu Ile Thr Gly Ile Ser Ser Thr Leu His Thr Ala His
225                 230                 235                 240

Gln Glu Ala Asp Glu Ile Leu Glu Glu Ile Ile Ser Glu His Arg Ala
                245                 250                 255

Ser Lys Thr Ala Asp Gly Asp Asp Tyr Glu Ala Asp Asn Ile Leu Gly
            260                 265                 270

Val Leu Leu Asp Ile Gln Glu Arg Gly Asn Leu Gln Val Pro Leu Thr
        275                 280                 285

Thr Asp Asn Ile Lys Ala Ile Ile Leu Asp Met Phe Ala Gly Ala Ser
    290                 295                 300

Asp Thr Ser Leu Thr Thr Ala Glu Trp Ala Met Ala Glu Met Val Lys
305                 310                 315                 320

His Pro Arg Ile Met Lys Lys Ala Gln Asp Glu Val Arg Arg Thr Leu
                325                 330                 335

Asn Gln Glu Gly Asn Val Ala Asn Leu Leu Pro Glu Leu Lys Tyr Leu
            340                 345                 350

Lys Leu Val Ile Lys Glu Thr Leu Arg Leu His Pro Pro Val Ala Leu
        355                 360                 365

Ile Pro Arg Glu Cys Asp Gly Arg Cys Glu Leu Asn Gly Tyr Asp Val
    370                 375                 380

Asn Pro Lys Thr Lys Ile Leu Val Asn Ala Trp Ala Ile Gly Arg Asp
385                 390                 395                 400

His Asn Leu Trp Asn Asp Pro Glu Arg Phe Asp Pro Glu Arg Phe Leu
                405                 410                 415

Asp Asn Ser Ser Asp Phe Arg Gly Thr Asp Phe Lys Phe Ile Pro Phe
            420                 425                 430

Gly Ala Gly Lys Arg Ile Cys Pro Gly Ile Thr Met Ala Ile Thr Ile
        435                 440                 445

Ile Glu Val Leu Leu Ala Gln Leu Leu Tyr His Phe Asp Trp Lys Leu
```

```
    450                 455                 460

Pro Asp Gly Ala Lys Pro Glu Ser Leu Asp Met Ser Asp Thr Phe Gly
465                 470                 475                 480

Leu Val Val Lys Arg Arg Ile Asp Leu Asn Leu Ile Pro Ile Pro
                485                 490                 495


<210> SEQ ID NO 50
<211> LENGTH: 498
<212> TYPE: PRT
<213> ORGANISM: Jatropha curcas

<400> SEQUENCE: 50

Met Glu Tyr Gln Ile Leu Ser Ser Pro Thr Leu Ile Ala Leu Leu Val
1               5                   10                  15

Phe Val Ala Thr Val Val Ile Lys Leu Trp Lys Arg Pro Thr Ile Ala
            20                  25                  30

Asn Asn Asn Pro Pro Pro Gly Pro Trp Lys Leu Pro Leu Ile Gly Asn
        35                  40                  45

Leu His Asn Leu Phe Gly Arg Asp Gln Pro His His Arg Leu Arg Asp
    50                  55                  60

Leu Ala Gly Lys Tyr Gly Ala Val Met Gly Phe Gln Leu Gly Gln Val
65                  70                  75                  80

Pro Thr Val Val Ile Ser Ser Ala Glu Ile Ala Lys Gln Val Leu Lys
                85                  90                  95

Thr His Glu Phe Gln Phe Ile Asp Arg Pro Ser Leu Leu Ala Ala Asp
            100                 105                 110

Ile Val Leu Tyr Asn Arg Ser Asp Ile Ile Phe Ala Pro Tyr Gly Asp
        115                 120                 125

Tyr Trp Arg Gln Ile Lys Lys Ile Ala Ile Leu Glu Leu Leu Ser Ser
    130                 135                 140

Lys Arg Val Gln Ser Phe Lys Ser Val Arg Glu Glu Glu Val Ser Ser
145                 150                 155                 160

Phe Phe Lys Phe Leu Tyr Ser Lys Ala Gly Ser Pro Val Asn Leu Ser
                165                 170                 175

Arg Thr Leu Leu Ser Leu Thr Asn Gly Ile Ile Ala Lys Thr Ser Ile
            180                 185                 190

Gly Lys Lys Cys Lys Arg Gln Glu Glu Ile Ile Ala Val Ile Thr Asp
        195                 200                 205

Ala Ile Lys Ala Thr Gly Gly Phe Ser Val Ala Asp Val Phe Pro Ser
    210                 215                 220

Phe Lys Phe Leu His Ile Ile Thr Gly Ile Ser Ser Thr Ile Arg Arg
225                 230                 235                 240

Ile His Arg Glu Ala Asp Thr Ile Leu Glu Glu Ile Met Asp Glu His
                245                 250                 255

Lys Ala Asn Asn Glu Ser Lys Asn Glu Pro Asp Asn Ile Leu Asp Val
            260                 265                 270

Leu Leu Asp Ile Gln Gln Arg Gly Asn Leu Glu Phe Pro Leu Thr Ala
        275                 280                 285

Asp Asn Ile Lys Ala Ile Ile Leu Glu Met Phe Gly Ala Ala Ser Asp
    290                 295                 300

Thr Ser Ser Val Thr Ile Glu Trp Ala Met Ser Glu Met Met Lys Asn
305                 310                 315                 320

Pro Trp Thr Met Lys Lys Ala Gln Glu Glu Val Arg Glu Val Phe Asn
                325                 330                 335
```

```
Gly Thr Gly Asp Val Ser Glu Ala Ser Leu Gln Glu Leu Gln Tyr Leu
            340                 345                 350

Lys Leu Val Ile Lys Glu Thr Leu Arg Leu His Pro Pro Leu Thr Leu
        355                 360                 365

Ile Pro Arg Glu Cys Asn Gln Lys Cys Gln Ile Asn Glu Tyr Asp Ile
    370                 375                 380

Tyr Pro Lys Thr Arg Val Leu Val Asn Ala Trp Ala Ile Gly Arg Asp
385                 390                 395                 400

Pro Asn Trp Trp Thr Asp Pro Glu Arg Phe Asp Pro Glu Arg Phe Arg
                405                 410                 415

Cys Gly Ser Val Asp Phe Lys Gly Thr Asp Phe Glu Phe Ile Pro Phe
            420                 425                 430

Gly Ala Gly Lys Arg Met Cys Pro Gly Ile Thr Met Ala Met Ala Asn
        435                 440                 445

Ile Glu Leu Ile Leu Ala Gln Leu Leu Tyr His Phe Asn Trp Glu Leu
    450                 455                 460

Pro Gly Lys Ala Lys Pro Glu Thr Leu Asp Met Ser Glu Ser Phe Gly
465                 470                 475                 480

Leu Ala Val Lys Arg Lys Val Glu Leu Asn Leu Ile Pro Thr Ala Phe
                485                 490                 495

Asn Pro


<210> SEQ ID NO 51
<211> LENGTH: 503
<212> TYPE: PRT
<213> ORGANISM: Jathropha curcas

<400> SEQUENCE: 51

Met Glu Gln Gln Ile Leu Ser Phe Pro Val Ile Phe Asn Phe Leu Leu
1               5                   10                  15

Phe Leu Leu Val Leu Leu Lys Val Ser Lys Lys Leu Ser Lys His Asp
            20                  25                  30

Ser Asn Ser Pro Pro Gly Pro Trp Lys Leu Pro Phe Leu Gly Asn Phe
        35                  40                  45

Leu Gln Leu Ala Gly Asp Leu Pro His Arg Arg Ile Thr Glu Leu Ala
    50                  55                  60

Lys Lys Tyr Gly Pro Val Met Ser Ile Lys Leu Gly Gln His Pro Tyr
65                  70                  75                  80

Leu Val Val Ser Ser Pro Glu Thr Ala Lys Glu Val Met Arg Thr Gln
                85                  90                  95

Asp Pro Ile Phe Ala Asp Arg Pro Leu Val Leu Ala Gly Glu Leu Val
            100                 105                 110

Leu Tyr Asn Arg Asn Asp Ile Gly Phe Gly Leu Tyr Gly Asp Gln Trp
        115                 120                 125

Arg Gln Met Arg Lys Phe Cys Ala Leu Glu Leu Leu Ser Thr Lys Arg
    130                 135                 140

Ile Gln Ser Phe Arg Ser Val Arg Glu Glu Glu Ile Ala Val Phe Val
145                 150                 155                 160

Lys Ser Leu Arg Ser Lys Glu Gly Ser Ser Val Asn Leu Ser His Thr
                165                 170                 175

Leu Phe Ala Leu Thr Asn Ser Ile Ile Ala Arg Asn Thr Val Gly His
            180                 185                 190

Lys Ser Lys Asn Gln Glu Ala Leu Leu Lys Ile Ile Asp Asp Ile Val
        195                 200                 205
```

```
Glu Ser Leu Gly Gly Leu Ser Thr Val Asp Ile Phe Pro Ser Leu Lys
    210                 215                 220

Trp Leu Pro Ser Val Lys Arg Glu Arg Ser Arg Ile Trp Lys Leu His
225                 230                 235                 240

Cys Glu Thr Asp Glu Ile Leu Glu Gly Ile Leu Glu Glu His Lys Ala
                245                 250                 255

Asn Arg Gln Ala Ala Ala Phe Lys Asn Asp Asp Gly Ser Gln Ala Asp
            260                 265                 270

Asn Leu Leu Asp Val Leu Leu Asp Leu Gln Gln Asn Gly Asn Leu Gln
        275                 280                 285

Val Pro Leu Thr Asp Val Asn Ile Lys Ala Val Ile Leu Gly Met Phe
    290                 295                 300

Gly Ala Gly Ser Asp Thr Ser Ser Lys Thr Thr Glu Trp Ala Met Ala
305                 310                 315                 320

Glu Leu Met Lys Asn Pro Glu Ile Met Lys Asn Ala Gln Glu Glu Leu
                325                 330                 335

Arg Ser Leu Phe Gly Glu Ser Gly Asn Val Asp Glu Ala Lys Leu His
            340                 345                 350

Glu Ile Lys Trp Leu Lys Leu Ile Ile Asn Glu Thr Leu Arg Leu His
        355                 360                 365

Pro Ala Val Thr Leu Ile Pro Arg Leu Cys Arg Glu Lys Thr Lys Ile
    370                 375                 380

Ser Gly Tyr Asp Val Tyr Pro Asn Thr Arg Val Phe Ile Asn Thr Trp
385                 390                 395                 400

Ala Ile Gly Arg Asp Pro Ile Ile Trp Thr Glu Pro Glu Lys Phe Val
                405                 410                 415

Pro Glu Arg Phe Ile Asp Ser Ser Ile Asp Tyr Arg Gly Asn His Phe
            420                 425                 430

Glu Tyr Thr Pro Phe Gly Ala Gly Arg Arg Ile Cys Pro Gly Met Thr
        435                 440                 445

Phe Gly Met Val Asn Leu Glu Ile Phe Leu Ala Asn Leu Leu Tyr His
    450                 455                 460

Phe Asp Trp Lys Leu Pro Lys Gly Ile Thr Ser Glu Asn Leu Asp Met
465                 470                 475                 480

Thr Glu Asn Phe Gly Gly Val Ile Lys Arg Lys Gln Asp Leu Glu Leu
                485                 490                 495

Ile Pro Val Pro Phe Arg Pro
            500


<210> SEQ ID NO 52
<211> LENGTH: 503
<212> TYPE: PRT
<213> ORGANISM: Jatropha curcas

<400> SEQUENCE: 52

Met Glu Asp Gln Ile Leu Ser Phe Gln Val Leu Phe Ser Phe Leu Leu
1               5                   10                  15

Phe Leu Phe Val Leu Phe Lys Val Ser Lys Lys Leu Tyr Lys His Gly
            20                  25                  30

Ser Asn Pro Pro Pro Gly Pro Leu Lys Leu Pro Phe Leu Gly Asn Ile
        35                  40                  45

Leu Gln Leu Ala Gly Asp Val Pro His Arg Arg Leu Thr Ala Leu Ala
    50                  55                  60

Lys Thr Tyr Gly Pro Val Met Gly Ile Lys Leu Gly Gln Ile Pro Phe
65                  70                  75                  80
```

```
Leu Val Val Ser Ser Pro Glu Thr Ala Lys Glu Val Met Lys Ile Gln
                85                  90                  95

Asp Pro Val Phe Ala Glu Arg Ala Pro Leu Leu Ala Gly Glu Ile Val
            100                 105                 110

Leu Tyr Asn Arg Asn Asp Ile Ile Phe Gly Leu Tyr Gly Asp Gln Trp
        115                 120                 125

Arg Gln Met Arg Lys Ile Cys Thr Leu Glu Leu Leu Ser Ala Lys Arg
    130                 135                 140

Val Gln Ser Phe Arg Ser Val Arg Glu Glu Glu Val Ala Asp Leu Val
145                 150                 155                 160

Lys Phe Leu Gly Ser Lys Glu Gly Ser Pro Val Asn Leu Thr His Thr
                165                 170                 175

Leu Phe Ala Leu Ala Asn Ser Ile Ile Ala Arg Asn Thr Val Gly Gln
            180                 185                 190

Lys Ser Lys Asn Gln Glu Ala Leu Leu Arg Leu Ile Asp Asp Ile Ile
        195                 200                 205

Glu Leu Thr Gly Ser Val Ser Ile Ala Asp Ile Phe Pro Ser Leu Lys
    210                 215                 220

Trp Leu Pro Ser Val Gln Arg Asp Arg Ser Arg Ile Arg Lys Leu His
225                 230                 235                 240

Tyr Glu Thr Asp Glu Ile Leu Glu Asp Ile Leu Gln Glu His Arg Ala
                245                 250                 255

Asn Arg Gln Ala Ala Ala Ser Arg Lys Gly Asp Arg Arg Gly Ala Asp
            260                 265                 270

Asn Leu Leu Asp Val Leu Leu Tyr Leu Gln Glu Thr Gly Asn Leu Asp
        275                 280                 285

Val Pro Leu Thr Asp Val Ala Ile Lys Ala Ala Ile Ile Asp Met Phe
    290                 295                 300

Gly Ala Gly Ser Asp Thr Ser Ser Lys Thr Val Glu Trp Ala Met Ala
305                 310                 315                 320

Glu Leu Met Arg Asn Pro Glu Ile Met Lys Lys Ala Gln Glu Glu Leu
                325                 330                 335

Arg Asn Phe Phe Gly Glu Asn Gly Lys Val Asp Glu Ala Lys Leu Gln
            340                 345                 350

Glu Leu Lys Trp Leu Asn Leu Ile Asn Lys Glu Thr Leu Arg Leu His
        355                 360                 365

Pro Ala Ala Ala Val Val Pro Arg Val Cys Arg Glu Arg Thr Lys Val
    370                 375                 380

Ser Gly Tyr Asp Val Tyr Pro Gly Thr Arg Val Phe Ile Asn Ala Trp
385                 390                 395                 400

Ala Ile Gly Arg Asp Pro Lys Val Trp Ser Glu Ala Glu Lys Phe Lys
                405                 410                 415

Pro Glu Arg Phe Ile Asp Ser Ala Ile Asp Tyr Arg Gly Thr Asn Phe
            420                 425                 430

Glu Leu Ile Pro Phe Gly Ala Gly Lys Arg Ile Cys Pro Gly Met Thr
        435                 440                 445

Leu Gly Met Ala Asn Leu Glu Ile Phe Leu Ala Asn Leu Leu Tyr His
    450                 455                 460

Phe Asp Trp Lys Phe Pro Lys Gly Val Thr Ala Glu Asn Leu Asp Met
465                 470                 475                 480

Asn Glu Ala Phe Gly Ala Ala Val Lys Arg Lys Val Asp Leu Glu Leu
                485                 490                 495
```

-continued

```
Val Pro Ile Pro Phe Arg Pro
            500


<210> SEQ ID NO 53
<211> LENGTH: 26
<212> TYPE: DNA
<213> ORGANISM: artificial sequence
<220> FEATURE:
<223> OTHER INFORMATION: primer

<400> SEQUENCE: 53

atggacaagc aaatcctatc atatcc                                          26


<210> SEQ ID NO 54
<211> LENGTH: 22
<212> TYPE: DNA
<213> ORGANISM: artificial sequence
<220> FEATURE:
<223> OTHER INFORMATION: primer

<400> SEQUENCE: 54

tcagtccgtt gttggtgaag gg                                              22


<210> SEQ ID NO 55
<211> LENGTH: 21
<212> TYPE: DNA
<213> ORGANISM: artificial sequence
<220> FEATURE:
<223> OTHER INFORMATION: primer

<400> SEQUENCE: 55

atggagcagc aattgctatc g                                               21


<210> SEQ ID NO 56
<211> LENGTH: 26
<212> TYPE: DNA
<213> ORGANISM: artificial sequence
<220> FEATURE:
<223> OTHER INFORMATION: primer

<400> SEQUENCE: 56

ctatggcaaa gtagtgaatg gaatgg                                          26


<210> SEQ ID NO 57
<211> LENGTH: 24
<212> TYPE: DNA
<213> ORGANISM: artificial sequence
<220> FEATURE:
<223> OTHER INFORMATION: primer

<400> SEQUENCE: 57

atggcactgc aatcactact attc                                            24


<210> SEQ ID NO 58
<211> LENGTH: 27
<212> TYPE: DNA
<213> ORGANISM: artificial sequence
<220> FEATURE:
<223> OTHER INFORMATION: primer

<400> SEQUENCE: 58

ttacacatgt tttgttttgg tttctcc                                         27


<210> SEQ ID NO 59
<211> LENGTH: 22
<212> TYPE: DNA
```

<213> ORGANISM: artificial sequence
<220> FEATURE:
<223> OTHER INFORMATION: primer

<400> SEQUENCE: 59
atgtcattgc aacctgcacc tg 22

<210> SEQ ID NO 60
<211> LENGTH: 25
<212> TYPE: DNA
<213> ORGANISM: artificial sequence
<220> FEATURE:
<223> OTHER INFORMATION: primer

<400> SEQUENCE: 60
ttaaggatga aatagaacag gaatc 25

<210> SEQ ID NO 61
<211> LENGTH: 23
<212> TYPE: DNA
<213> ORGANISM: artificial sequence
<220> FEATURE:
<223> OTHER INFORMATION: primer

<400> SEQUENCE: 61
atggaaagtg ctgctcacca atc 23

<210> SEQ ID NO 62
<211> LENGTH: 26
<212> TYPE: DNA
<213> ORGANISM: artificial sequence
<220> FEATURE:
<223> OTHER INFORMATION: primer

<400> SEQUENCE: 62
ttatggtaaa ggactgacgg gaatgg 26

<210> SEQ ID NO 63
<211> LENGTH: 28
<212> TYPE: DNA
<213> ORGANISM: artificial sequence
<220> FEATURE:
<223> OTHER INFORMATION: primer

<400> SEQUENCE: 63
atggagaaac aaatcctatc atttccag 28

<210> SEQ ID NO 64
<211> LENGTH: 25
<212> TYPE: DNA
<213> ORGANISM: artificial sequence
<220> FEATURE:
<223> OTHER INFORMATION: primer

<400> SEQUENCE: 64
ctaaggagta aatggaatgg gaatc 25

<210> SEQ ID NO 65
<211> LENGTH: 25
<212> TYPE: DNA
<213> ORGANISM: artificial sequence
<220> FEATURE:
<223> OTHER INFORMATION: primer

<400> SEQUENCE: 65
atgtcatcac aaccagcagt tttac 25

<210> SEQ ID NO 66
<211> LENGTH: 24
<212> TYPE: DNA
<213> ORGANISM: artificial sequence
<220> FEATURE:
<223> OTHER INFORMATION: primer

<400> SEQUENCE: 66
tcaatgtgta ggatatagaa cagg 24

<210> SEQ ID NO 67
<211> LENGTH: 22
<212> TYPE: DNA
<213> ORGANISM: artificial sequence
<220> FEATURE:
<223> OTHER INFORMATION: primer

<400> SEQUENCE: 67
ttcatatttg ttgctaatcc tc 22

<210> SEQ ID NO 68
<211> LENGTH: 25
<212> TYPE: DNA
<213> ORGANISM: artificial sequence
<220> FEATURE:
<223> OTHER INFORMATION: primer

<400> SEQUENCE: 68
caaggtacag gatttatgca aatcc 25

<210> SEQ ID NO 69
<211> LENGTH: 36
<212> TYPE: DNA
<213> ORGANISM: artificial sequence
<220> FEATURE:
<223> OTHER INFORMATION: primer

<400> SEQUENCE: 69
aaaaggcgcg ccaaaaatgg acaagcaaat cctatc 36

<210> SEQ ID NO 70
<211> LENGTH: 32
<212> TYPE: DNA
<213> ORGANISM: artificial sequence
<220> FEATURE:
<223> OTHER INFORMATION: primer

<400> SEQUENCE: 70
aaaattaatt aatcagtccg ttgttggtga ag 32

<210> SEQ ID NO 71
<211> LENGTH: 37
<212> TYPE: DNA
<213> ORGANISM: artificial sequence
<220> FEATURE:
<223> OTHER INFORMATION: primer

<400> SEQUENCE: 71
aaaaggcgcg ccaaaaatgg agcagcaatt gctatcg 37

<210> SEQ ID NO 72
<211> LENGTH: 32
<212> TYPE: DNA
<213> ORGANISM: artificial sequence
<220> FEATURE:

<223> OTHER INFORMATION: primer

<400> SEQUENCE: 72
aaaattaatt aactatggca aagtagtgaa tg 32

<210> SEQ ID NO 73
<211> LENGTH: 40
<212> TYPE: DNA
<213> ORGANISM: artificial sequence
<220> FEATURE:
<223> OTHER INFORMATION: primer

<400> SEQUENCE: 73
aaaaggcgcg ccaaaaatgg cactgcaatc actactattc 40

<210> SEQ ID NO 74
<211> LENGTH: 38
<212> TYPE: DNA
<213> ORGANISM: artificial sequence
<220> FEATURE:
<223> OTHER INFORMATION: primer

<400> SEQUENCE: 74
aaaattaatt aattacacat gttttgtttt ggtttctc 38

<210> SEQ ID NO 75
<211> LENGTH: 38
<212> TYPE: DNA
<213> ORGANISM: artificial sequence
<220> FEATURE:
<223> OTHER INFORMATION: primer

<400> SEQUENCE: 75
aaaaggcgcg ccaaaaatgt cattgcaacc tgcacctg 38

<210> SEQ ID NO 76
<211> LENGTH: 32
<212> TYPE: DNA
<213> ORGANISM: artificial sequence
<220> FEATURE:
<223> OTHER INFORMATION: primer

<400> SEQUENCE: 76
aaaattaatt aattaaggat gaaatagaac ag 32

<210> SEQ ID NO 77
<211> LENGTH: 39
<212> TYPE: DNA
<213> ORGANISM: artificial sequence
<220> FEATURE:
<223> OTHER INFORMATION: primer

<400> SEQUENCE: 77
aaaaggcgcg ccaaaaatgg aaagtgctgc tcaccaatc 39

<210> SEQ ID NO 78
<211> LENGTH: 31
<212> TYPE: DNA
<213> ORGANISM: artificial sequence
<220> FEATURE:
<223> OTHER INFORMATION: primer

<400> SEQUENCE: 78
aaaattaatt aattatggta aaggactgac g 31

-continued

<210> SEQ ID NO 79
<211> LENGTH: 41
<212> TYPE: DNA
<213> ORGANISM: artificial sequence
<220> FEATURE:
<223> OTHER INFORMATION: primer

<400> SEQUENCE: 79
aaaaggcgcg ccaaaaatgg agaaacaaat cctatcattt c 41

<210> SEQ ID NO 80
<211> LENGTH: 31
<212> TYPE: DNA
<213> ORGANISM: artificial sequence
<220> FEATURE:
<223> OTHER INFORMATION: primer

<400> SEQUENCE: 80
aaaattaatt aactaaggag taaatggaat g 31

<210> SEQ ID NO 81
<211> LENGTH: 41
<212> TYPE: DNA
<213> ORGANISM: artificial sequence
<220> FEATURE:
<223> OTHER INFORMATION: primer

<400> SEQUENCE: 81
aaaaggcgcg ccaaaaatgt catcacaacc agcagtttta c 41

<210> SEQ ID NO 82
<211> LENGTH: 33
<212> TYPE: DNA
<213> ORGANISM: artificial sequence
<220> FEATURE:
<223> OTHER INFORMATION: primer

<400> SEQUENCE: 82
aaaattaatt aatcaatgtg taggatatag aac 33

<210> SEQ ID NO 83
<211> LENGTH: 38
<212> TYPE: DNA
<213> ORGANISM: artificial sequence
<220> FEATURE:
<223> OTHER INFORMATION: primer

<400> SEQUENCE: 83
aaaaggcgcg ccaaaaatgg caatgcaacc tgcaattg 38

<210> SEQ ID NO 84
<211> LENGTH: 37
<212> TYPE: DNA
<213> ORGANISM: artificial sequence
<220> FEATURE:
<223> OTHER INFORMATION: primer

<400> SEQUENCE: 84
aaaattaatt aatcaagtgg caataggttc aatgaac 37

<210> SEQ ID NO 85
<211> LENGTH: 1845
<212> TYPE: DNA
<213> ORGANISM: Ricinus communis

<400> SEQUENCE: 85

-continued

```
atggcactgc aatcactact attcttacag gcaaactctc aaaatcgaaa tttttgtcaa      60
ttcttaagca tgccctcaat caggtgctgt agctgtcgag tcccttttc ttcatggtct      120
gctaaatcag tgactaataa gtcacctcaa gcctgtttat caacaaaatc ccagcaagaa     180
ttccgtccac tggcaaactt tcctcccact gtatggggca gtcactttgc ttctccaacc     240
tttagtgaat cggaatttgg gacttatgat agacaagcaa acgtcctgca gaaaaagatc     300
cgagaactct taacgtcgtc cagaagtgat tcggtggaga aaattgcttt tatcgactta     360
ctgtgtcgtc ttggtgtctc gtatcatttt gagaatgaca ttgaagagca actgagtcaa     420
attttcagtt gccaacctgg tctccttgat gaaaaacaat acgatctcta tactgttgca     480
cttgtatttc gagttttcag acagcatggt ttcaaaatgt cttctaatgt gttccacaaa     540
ttcacggaca gccatggtaa attcaaggct tccctgctaa gcgatgccaa aggtatgctc     600
agcctttttg aagctagcca tttaagcatg catggagaag acattcttga tgaagccttt     660
gctttcacca aggattactt ggagtcctct gcagttgacc agtacttatg ccctaatctt     720
caaaagcata taactaacgc cctggagcag cctttccaca aaggcatacc aagactagag     780
gccaggaaat acattgacct atacgaaggc gacgaatgcc gaaatgaaac agtactcgag     840
tttgcaaagt tggactataa tagagtacaa ttattacacc aacaagagct aagccagttc     900
tcaacgtggt ggaaagacct caatcttgct tcggagattc cttatgcaag agacagaatg     960
gcagaaattt tcttttgggc tgttgcaatg tattttgagc ctaagtatgc acaagctcga    1020
atgattattg ctaaagttgt attgctcata tcacttgtag atgatacatt tgatgcatat    1080
gccactattg aagaaaccca tcttcttgca gaagcattcg aaaggtggga taagagctgc    1140
ctggatcagc tgccagatta catgaaagtt atctataaac tattgctaaa caccttttct    1200
gaatttgaga atgatttggc aaaggaggga aagtcctata gtgtcagata tgggagggaa    1260
gcgtttcaag aactagttag aggctactac ctggaggcta tgtggcgtga tgagggaaaa    1320
ataccatcat tcgatgagta catacgcaat ggatcattgt caagcggatt acctcttgtc    1380
gtgacagcat ctttcatggg agtcaaagaa attacaggga tcagagaatt tcagtggcta    1440
aggactaaac ccaaattaaa tcatttttct ggtgcagtag gaaggattat gaatgacata    1500
atgtctcatg tgagcgagca aaatagagga catgttgcat cttgcataga ttgctacatg    1560
aaacaatatg aagtttccaa ggaggaagca attaaagaga tgcagaaaat ggctagcgat    1620
gcttggaagg atataaacga aggatatatg aggccagcac aagtatcagt tagtgaacta    1680
atgagagtgg tcaaccttgc acgactaaca gatgtgagct ataaatatgg cgatggttat    1740
actgatccac aacacttgaa acagtttgtt aaaggattgt tcatagatcc ggttcctctt    1800
ccaaatcaaa ttcgtaaagg agaaaccaaa acaaaacatg tgtaa                    1845
```

<210> SEQ ID NO 86
<211> LENGTH: 211
<212> TYPE: DNA
<213> ORGANISM: Jatropha curcas

<400> SEQUENCE: 86

```
atggcaatgc aacctgcaat tgttcaagca aactcccaaa aacaaatcct tactactccg      60
ttcttattaa gcacacctag tactaagctt aacgacagtc gttttgcttc cttttccttg     120
gctaagccaa caactttag aaaacttaaa gcatgtgcat caacaaaatc tgagacagaa      180
gctcgtccct tagcctactt tcctcctact g                                    211
```